(12) United States Patent
Kubota et al.

(10) Patent No.: US 11,730,363 B2
(45) Date of Patent: Aug. 22, 2023

(54) OPTICAL COHERENCE TOMOGRAPHY PATIENT ALIGNMENT SYSTEM FOR HOME BASED OPHTHALMIC APPLICATIONS

(71) Applicant: ACUCELA INC., Seattle, WA (US)

(72) Inventors: Ryo Kubota, Seattle, WA (US); Philip M. Buscemi, Mount Pleasant, SC (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 17/757,748

(22) PCT Filed: Sep. 2, 2020

(86) PCT No.: PCT/US2020/070486
§ 371 (c)(1),
(2) Date: Jun. 20, 2022

(87) PCT Pub. No.: WO2021/134087
PCT Pub. Date: Jul. 1, 2021

(65) Prior Publication Data
US 2023/0020468 A1    Jan. 19, 2023

Related U.S. Application Data

(60) Provisional application No. 62/953,827, filed on Dec. 26, 2019.

(51) Int. Cl.
*A61B 3/10* (2006.01)
*A61B 3/00* (2006.01)
*A61B 3/12* (2006.01)

(52) U.S. Cl.
CPC ............ *A61B 3/102* (2013.01); *A61B 3/0075* (2013.01); *A61B 3/0091* (2013.01); *A61B 3/1005* (2013.01); *A61B 3/12* (2013.01)

(58) Field of Classification Search
CPC ..... A61B 3/102; A61B 3/0075; A61B 3/0091; A61B 3/1005; A61B 3/12
(Continued)

(56) References Cited

U.S. PATENT DOCUMENTS 5,255,274 A   10/1993  Wysocki
5,396,325 A    3/1995  Carome
(Continued)

FOREIGN PATENT DOCUMENTS

CA          3111012      1/2021
CN        105188540     12/2015
(Continued)

OTHER PUBLICATIONS

Bengio, Yoshua, et al., "Curriculum Learning," 8 pages, retrieved from http://machinelearning.org/archive/icml2009/papers/119.pdf on Jun. 14, 2021.
(Continued)

*Primary Examiner* — Mohammed A Hasan
(74) *Attorney, Agent, or Firm* — FisherBroyles LLP; John Shimmick

(57) ABSTRACT

Improved optical coherence tomography systems and methods to measure retinal data are presented. The systems may be compact, provide in-home monitoring, and have automation to allow the patient to measure himself or herself.

17 Claims, 29 Drawing Sheets

(58) Field of Classification Search
USPC ........................................................ 351/221
See application file for complete search history.

(56) References Cited

U.S. PATENT DOCUMENTS

| | | | |
|---|---|---|---|
| 6,053,613 A | 4/2000 | Wei |
| 6,325,512 B1 | 12/2001 | Wei |
| 6,362,919 B1 | 3/2002 | Flanders |
| 6,409,395 B1 | 6/2002 | Wang |
| 6,419,360 B1 | 7/2002 | Hauger |
| 6,445,944 B1 | 9/2002 | Ostrovsky |
| 6,552,796 B2 | 4/2003 | Magnin |
| 6,726,325 B2 | 4/2004 | Jing-Gang |
| 6,736,508 B2 | 5/2004 | Jing-Gang |
| 6,769,769 B2 | 8/2004 | Podoleanu |
| 6,778,307 B2 | 8/2004 | Clark |
| 7,113,818 B2 | 9/2006 | Podoleanu |
| 7,126,693 B2 | 10/2006 | Everett |
| 7,140,730 B2 | 11/2006 | Wei |
| 7,301,644 B2 | 11/2007 | Knighton |
| 7,324,569 B2 | 1/2008 | Flanders |
| 7,347,548 B2 | 3/2008 | Huang |
| 7,375,818 B2 | 5/2008 | Kawahara |
| 7,391,520 B2 | 6/2008 | Zhou |
| 7,452,077 B2 | 11/2008 | Meyer |
| 7,482,589 B2 | 1/2009 | Flanders |
| 7,542,145 B2 | 6/2009 | Toida |
| 7,594,730 B2 | 9/2009 | Podoleanu |
| 7,602,500 B2 | 10/2009 | Izatt |
| 7,633,623 B2 | 12/2009 | Hatori |
| 7,633,627 B2 | 12/2009 | Choma |
| 7,701,585 B2 | 4/2010 | Hatori |
| 7,761,139 B2 | 7/2010 | Tearney |
| 7,783,337 B2 | 8/2010 | Feldman |
| 7,864,335 B2 | 1/2011 | Terakawa |
| 7,872,759 B2 | 1/2011 | Tearney |
| 7,929,148 B2 | 4/2011 | Kemp |
| 7,954,947 B2 | 6/2011 | Sugita |
| 7,971,999 B2 | 7/2011 | Zinser |
| 7,980,694 B2 | 7/2011 | Keating |
| 7,980,696 B1 | 7/2011 | Taki |
| 7,997,728 B2 | 8/2011 | Huang |
| 7,997,729 B2 | 8/2011 | McLean |
| 3,025,403 A1 | 9/2011 | Peter |
| 3,049,900 A1 | 11/2011 | Kemp |
| 3,055,107 A1 | 11/2011 | Tadashi |
| 3,079,711 A1 | 12/2011 | Stetson |
| 8,123,354 B2 | 2/2012 | Olivier |
| 8,139,226 B2 | 3/2012 | Johnson |
| 8,192,024 B2 | 6/2012 | Yumikake |
| 8,205,991 B2 | 6/2012 | Wei |
| 8,220,924 B2 | 7/2012 | Hanebuchi |
| 8,251,510 B2 | 8/2012 | Kobayashi |
| 8,251,511 B2 | 8/2012 | Stetson |
| 8,282,211 B2 | 10/2012 | Campbell |
| 8,289,522 B2 | 10/2012 | Tearney |
| 8,348,427 B2 | 1/2013 | Buckland |
| 8,348,429 B2 | 1/2013 | Walsh |
| 8,351,665 B2 | 1/2013 | Tearney |
| 8,363,783 B2 | 1/2013 | Gertner |
| 8,403,481 B2 | 3/2013 | Izatt |
| 8,405,834 B2 | 3/2013 | Srinivasan |
| 8,421,855 B2 | 4/2013 | Buckland |
| 8,425,037 B2 | 4/2013 | Uhlhorn |
| 8,442,284 B2 | 5/2013 | Rogers |
| 8,446,593 B1 | 5/2013 | Ellerbee |
| 8,457,440 B1 | 6/2013 | Johnson |
| 8,467,051 B2 | 6/2013 | Flanders |
| 8,474,978 B2 | 7/2013 | Huang |
| 8,500,279 B2 | 8/2013 | Everett |
| 8,526,006 B2 | 9/2013 | Nebosis |
| 8,529,062 B2 | 9/2013 | Buckland |
| 8,594,757 B2 | 11/2013 | Boppart |
| 8,608,314 B2 | 12/2013 | Yoon |
| 8,630,697 B2 | 1/2014 | Meyer |
| 8,665,450 B2 | 3/2014 | Johnson |
| 8,711,366 B2 | 4/2014 | Everett |
| 8,721,078 B2 | 5/2014 | Torii |
| 8,724,870 B2 | 5/2014 | Sekine |
| 8,757,803 B2 | 6/2014 | Everett |
| 8,781,287 B2 | 7/2014 | Flanders |
| 8,794,763 B2 | 8/2014 | Stetson |
| 8,801,184 B2 | 8/2014 | Hacker |
| 8,820,931 B2 | 9/2014 | Walsh |
| 8,836,953 B2 | 9/2014 | Johnson |
| 8,870,376 B2 | 10/2014 | Hogan |
| 8,894,207 B2 | 11/2014 | Hee |
| 8,913,248 B2 | 12/2014 | Sharma |
| 8,922,782 B2 | 12/2014 | Flanders |
| 8,926,097 B2 | 1/2015 | Sakagawa |
| 8,939,582 B1 | 1/2015 | Spaide |
| 8,947,648 B2 | 2/2015 | Swanson |
| 8,953,167 B2 | 2/2015 | Johnson |
| 8,971,360 B2 | 3/2015 | Lewandowski |
| 8,992,018 B2 | 3/2015 | Makihira |
| 8,994,753 B2 | 3/2015 | Nakano |
| 8,998,412 B2 | 4/2015 | Makihira |
| 9,016,862 B2 | 4/2015 | Carnevale |
| 9,025,160 B2 | 5/2015 | Moore |
| 9,025,847 B2 | 5/2015 | Kitamura |
| 9,033,504 B2 | 5/2015 | Everett |
| 9,033,510 B2 | 5/2015 | Narasimha-Iyer |
| 9,044,164 B2 | 6/2015 | Hacker |
| 9,055,891 B2 | 6/2015 | Suehira |
| 9,055,892 B2 | 6/2015 | Narasimha-Iyer |
| 9,060,689 B2 | 6/2015 | Tearney |
| 9,084,562 B2 | 7/2015 | Kakuma |
| 9,095,281 B2 | 8/2015 | Sharma |
| 9,119,562 B2 | 9/2015 | Naba |
| 9,138,141 B2 | 9/2015 | Makihira |
| 9,144,378 B2 | 9/2015 | Suehira |
| 9,149,182 B2 | 10/2015 | Walsh |
| 9,161,690 B2 | 10/2015 | Tomatsu |
| 9,163,929 B2 | 10/2015 | Lim |
| 9,163,930 B2 | 10/2015 | Buckland |
| 9,167,964 B2 | 10/2015 | Everett |
| 9,171,367 B2 | 10/2015 | Iwase |
| 9,176,319 B2 | 11/2015 | Bouma |
| 9,178,330 B2 | 11/2015 | Oh |
| 9,192,294 B2 | 11/2015 | Sharma |
| 9,200,888 B2 | 12/2015 | Jaillon |
| 9,217,707 B2 | 12/2015 | Bajraszewski |
| 9,226,653 B2 | 1/2016 | Torii |
| 9,226,660 B2 | 1/2016 | De Boer |
| 9,241,626 B2 | 1/2016 | Narasimha-Iyer |
| 9,243,885 B2 | 1/2016 | Johnson |
| 9,259,151 B2 | 2/2016 | Murase |
| 9,267,783 B1 | 2/2016 | Sharma |
| 9,273,950 B2 | 3/2016 | Yazdanfar |
| 9,291,446 B2 | 3/2016 | Schneider |
| 9,310,182 B2 | 4/2016 | Goldberg |
| 9,339,186 B2 | 5/2016 | Somani |
| 9,354,038 B2 | 5/2016 | Yasuno |
| 9,373,933 B2 | 6/2016 | Njegovec |
| 9,375,158 B2 | 6/2016 | Vakoc |
| 9,377,293 B2 | 6/2016 | Hauger |
| 9,380,935 B2 | 7/2016 | Iwase |
| 9,408,532 B2 | 8/2016 | Makihira |
| 9,427,147 B2 | 8/2016 | Lujan |
| 9,427,150 B2 | 8/2016 | Muto |
| 9,433,353 B2 | 9/2016 | Hanebuchi |
| 9,468,374 B2 | 10/2016 | Makihira |
| 9,492,077 B2 | 11/2016 | Ebersbach |
| 9,492,079 B2 | 11/2016 | Walsh |
| 9,526,412 B2 | 12/2016 | Yang |
| 9,526,415 B2 | 12/2016 | Fukuma |
| 9,526,425 B2 | 12/2016 | Feldman |
| 9,532,713 B2 | 1/2017 | Levecq |
| 9,545,199 B2 | 1/2017 | Wang |
| 9,584,098 B2 | 2/2017 | Yamanari |
| 9,612,105 B2 | 4/2017 | Kemp |
| 9,615,736 B2 | 4/2017 | Yamashita |
| 9,633,424 B2 | 4/2017 | Nebosis |
| 9,649,024 B2 | 5/2017 | Hacker |

(56) References Cited

U.S. PATENT DOCUMENTS

| | | | |
|---|---|---|---|
| 9,649,025 B2 | 5/2017 | Jeglorz |
| 9,671,620 B2 | 6/2017 | Gupta |
| 9,696,132 B2 | 7/2017 | Jayaraman |
| 9,702,686 B2 | 7/2017 | Hattersley |
| 9,778,018 B2 | 10/2017 | Schmoll |
| 9,778,020 B2 | 10/2017 | Tumlinson |
| 9,784,559 B2 | 10/2017 | Huber |
| 9,812,846 B2 | 11/2017 | Yun |
| 9,869,542 B2 | 1/2018 | Goldberg |
| 9,897,538 B2 | 2/2018 | Tearney |
| 9,915,520 B2 | 3/2018 | Cable |
| 9,939,659 B2 | 4/2018 | Gupta |
| 9,948,061 B2 | 4/2018 | Njegovec |
| 9,977,184 B1 | 5/2018 | Wong |
| 9,978,159 B2 | 5/2018 | Kraus |
| 9,993,153 B2 | 6/2018 | Chong |
| 10,045,692 B2 | 8/2018 | Tumlinson |
| 10,049,470 B2 | 8/2018 | Pintal |
| 10,098,537 B2 | 10/2018 | Iwase |
| 10,114,232 B2 | 10/2018 | Gupta |
| 10,327,631 B2 | 6/2019 | Huang |
| 10,413,175 B2 | 9/2019 | Yun |
| 10,478,058 B2 | 11/2019 | Cheng |
| 10,568,501 B2 | 2/2020 | Boss |
| 10,595,723 B2 | 3/2020 | Meznaric |
| 10,610,096 B2 | 4/2020 | Scheibler |
| 10,912,456 B2 | 2/2021 | Brennan |
| 10,952,607 B2 | 3/2021 | Scheibler |
| 10,959,613 B1 | 3/2021 | Kubota |
| 11,357,401 B2 | 6/2022 | Oggenfuss et al. |
| 11,369,266 B2 | 6/2022 | Kubota |
| 11,393,094 B2 | 7/2022 | Wyder |
| 11,497,396 B2 | 11/2022 | Kubota |
| 11,576,572 B2 | 2/2023 | Oggenfuss |
| 2005/0018133 A1 | 1/2005 | Huang |
| 2005/0140981 A1 | 6/2005 | Waelti |
| 2006/0131488 A1 | 6/2006 | Thingbo |
| 2006/0152106 A1 | 7/2006 | Yan |
| 2006/0244339 A1 | 11/2006 | Mazz |
| 2007/0076217 A1 | 4/2007 | Baker |
| 2007/0183643 A1 | 8/2007 | Jayaraman |
| 2007/0230856 A1 | 10/2007 | Yamazaki |
| 2007/0263171 A1* | 11/2007 | Ferguson ............ G01B 9/02044 |
| | | 351/206 |
| 2008/0100612 A1 | 5/2008 | Dastmalchi |
| 2008/0117427 A1 | 5/2008 | Teramura |
| 2008/0181263 A1 | 7/2008 | Bouma |
| 2008/0296480 A1 | 12/2008 | Haber |
| 2009/0123044 A1 | 5/2009 | Huang |
| 2009/0141237 A1 | 6/2009 | Izatt |
| 2009/0244485 A1* | 10/2009 | Walsh .................... A61B 3/111 |
| | | 351/221 |
| 2010/0110376 A1 | 5/2010 | Everett |
| 2010/0110377 A1 | 5/2010 | Maloca |
| 2011/0043757 A1 | 2/2011 | Everett |
| 2011/0080561 A1 | 4/2011 | Hayashi |
| 2011/0164633 A1 | 7/2011 | Moench |
| 2011/0299034 A1 | 12/2011 | Walsh |
| 2012/0033227 A1 | 2/2012 | Bower |
| 2012/0092616 A1 | 4/2012 | Peyman |
| 2012/0300216 A1 | 11/2012 | Johnson |
| 2012/0327365 A1 | 12/2012 | Makihira |
| 2013/0010259 A1 | 1/2013 | Carnevale |
| 2013/0010302 A1 | 1/2013 | Sharma |
| 2013/0016360 A1 | 1/2013 | Ensher |
| 2013/0103014 A1 | 4/2013 | Gooding |
| 2013/0158392 A1 | 6/2013 | Papac |
| 2013/0235343 A1 | 9/2013 | Hee |
| 2013/0250241 A1 | 9/2013 | Everett |
| 2014/0028997 A1 | 1/2014 | Cable |
| 2014/0112562 A1 | 4/2014 | Yamakawa |
| 2014/0121508 A1 | 5/2014 | Latimer |
| 2014/0125987 A1 | 5/2014 | Flanders |
| 2014/0218745 A1 | 8/2014 | Hattersley |
| 2014/0241605 A1 | 8/2014 | Izatt |
| 2014/0268050 A1 | 9/2014 | Jayaraman |
| 2014/0268169 A1 | 9/2014 | Jayaraman |
| 2014/0269796 A1 | 9/2014 | Geske |
| 2014/0285812 A1 | 9/2014 | Levitz |
| 2014/0307078 A1 | 10/2014 | Charles |
| 2014/0307753 A1 | 10/2014 | Minneman |
| 2014/0340689 A1 | 11/2014 | Namati |
| 2014/0347632 A1 | 11/2014 | Mordaunt |
| 2015/0010031 A1 | 1/2015 | Makino |
| 2015/0018674 A1 | 1/2015 | Scott |
| 2015/0055089 A1 | 2/2015 | Aono |
| 2015/0062532 A1 | 3/2015 | Sharma |
| 2015/0085253 A1 | 3/2015 | Walsh |
| 2015/0109579 A1 | 4/2015 | Orlowski |
| 2015/0110376 A1 | 4/2015 | Gessner |
| 2015/0198431 A1 | 7/2015 | Uchida |
| 2015/0216408 A1* | 8/2015 | Brown ................. A61B 3/1015 |
| | | 351/215 |
| 2015/0216412 A1 | 8/2015 | Hillmann |
| 2015/0230705 A1 | 8/2015 | Kato |
| 2015/0327761 A1 | 11/2015 | Narasimha-Iyer |
| 2015/0327762 A1 | 11/2015 | Isogai |
| 2016/0000368 A1 | 1/2016 | Wang |
| 2016/0007857 A1 | 1/2016 | Wang |
| 2016/0025478 A1 | 1/2016 | Johnson |
| 2016/0040976 A1* | 2/2016 | Berkeley ............... A61B 3/0025 |
| | | 356/479 |
| 2016/0040977 A1 | 2/2016 | An |
| 2016/0040978 A1 | 2/2016 | Boppart |
| 2016/0081545 A1 | 3/2016 | Hauger |
| 2016/0082129 A1 | 3/2016 | Peters |
| 2016/0106310 A1 | 4/2016 | Moriguchi |
| 2016/0106312 A1 | 4/2016 | Moriguchi |
| 2016/0106314 A1 | 4/2016 | Everett |
| 2016/0128565 A1 | 5/2016 | Meznaric |
| 2016/0166143 A1 | 6/2016 | Goto |
| 2016/0206190 A1 | 7/2016 | Reisman |
| 2016/0242638 A1 | 8/2016 | Durbin |
| 2016/0252340 A1 | 9/2016 | Hollenbeck |
| 2016/0262609 A1 | 9/2016 | Cai |
| 2016/0270656 A1 | 9/2016 | Samec |
| 2016/0321828 A1 | 11/2016 | Tachikawa |
| 2016/0338589 A1 | 11/2016 | Carrasco-Zevallos |
| 2016/0367129 A1 | 12/2016 | Coelho |
| 2016/0367132 A1 | 12/2016 | Yun |
| 2017/0007182 A1 | 1/2017 | Samec |
| 2017/0020387 A1 | 1/2017 | Fingler |
| 2017/0049318 A1 | 2/2017 | Walsh |
| 2017/0055829 A1 | 3/2017 | Tan |
| 2017/0065169 A1 | 3/2017 | Taro |
| 2017/0074640 A1 | 3/2017 | Cable |
| 2017/0102223 A1 | 4/2017 | Izatt |
| 2017/0105618 A1 | 4/2017 | Schmoll |
| 2017/0140560 A1 | 5/2017 | Kraus |
| 2017/0156583 A1 | 6/2017 | Seesselberg |
| 2017/0205223 A1 | 7/2017 | Cable |
| 2017/0227350 A1 | 8/2017 | Sarunic |
| 2017/0231489 A1 | 8/2017 | Fujimori |
| 2017/0241763 A1 | 8/2017 | Wang |
| 2017/0258321 A1 | 9/2017 | Dastmalchi |
| 2017/0268987 A1 | 9/2017 | Swanson |
| 2017/0276471 A1 | 9/2017 | Jiang |
| 2017/0280993 A1 | 10/2017 | Fukuhara |
| 2017/0311795 A1 | 11/2017 | Sumiya |
| 2017/0356740 A1 | 12/2017 | Ansari |
| 2018/0012359 A1 | 1/2018 | Prentasic |
| 2018/0031363 A1 | 2/2018 | Johnson |
| 2018/0051978 A1 | 2/2018 | Flanders |
| 2018/0055358 A1 | 3/2018 | Nakajima |
| 2018/0064331 A1 | 3/2018 | Naba |
| 2018/0084994 A1 | 3/2018 | Su |
| 2018/0125354 A1 | 5/2018 | Pulaski |
| 2018/0135962 A1 | 5/2018 | Murata |
| 2018/0156598 A1 | 6/2018 | Cable |
| 2018/0157924 A1 | 6/2018 | Hogan |
| 2018/0168445 A1 | 6/2018 | Horn |
| 2018/0206716 A1 | 7/2018 | Chong |
| 2018/0271363 A1 | 9/2018 | Scheibler |
| 2018/0289256 A1 | 10/2018 | Murata |

(56) References Cited

U.S. PATENT DOCUMENTS

| | | |
|---|---|---|
| 2019/0365220 A1 | 12/2019 | Frisken |
| 2019/0380574 A1 | 12/2019 | Chen |
| 2020/0093363 A1 | 3/2020 | Saika |
| 2020/0196858 A1 | 6/2020 | Scheibler |
| 2020/0234080 A1 | 7/2020 | Ciller Ruiz |
| 2020/0342595 A1 | 10/2020 | Jia |
| 2020/0372632 A1 | 11/2020 | Chauhan |
| 2021/0127969 A1 | 5/2021 | Oggenfuss |
| 2021/0196113 A1 | 7/2021 | Copland |
| 2021/0386285 A1 | 12/2021 | Walsh |
| 2022/0265140 A1 | 8/2022 | Oggenfuss |

FOREIGN PATENT DOCUMENTS

| | | |
|---|---|---|
| CN | 105263415 | 1/2016 |
| CN | 105792728 | 7/2016 |
| DE | 102016121246 | 5/2018 |
| EP | 2725508 | 4/2014 |
| EP | 2759254 | 7/2014 |
| EP | 2892413 | 7/2015 |
| JP | 201172716 | 4/2011 |
| JP | 2011515194 | 5/2011 |
| JP | 201483266 | 5/2014 |
| JP | 2016513889 | 5/2016 |
| JP | 2016514828 | 5/2016 |
| WO | 9320743 | 10/1993 |
| WO | 2009120544 | 10/2009 |
| WO | 2010117386 | 10/2010 |
| WO | 2014144866 | 9/2014 |
| WO | 2014144998 | 9/2014 |
| WO | 2015082001 | 6/2015 |
| WO | 2015116981 | 8/2015 |
| WO | 2015120055 | 8/2015 |
| WO | 2016040534 | 3/2016 |
| WO | 2016073840 | 5/2016 |
| WO | 2016115387 | 7/2016 |
| WO | 2016125474 | 8/2016 |
| WO | 2016127140 | 8/2016 |
| WO | 2016148569 | 9/2016 |
| WO | 2016178298 | 11/2016 |
| WO | 2016179431 | 11/2016 |
| WO | 2016196463 | 12/2016 |
| WO | 2016203245 | 12/2016 |
| WO | 2017002379 | 1/2017 |
| WO | 2017025583 | 2/2017 |
| WO | 2017046225 | 3/2017 |
| WO | 2017048832 | 3/2017 |
| WO | 2017165793 | 9/2017 |
| WO | 2017176301 | 10/2017 |
| WO | 2017206929 | 12/2017 |
| WO | 2017216242 | 12/2017 |
| WO | 2018086173 | 5/2018 |
| WO | 2018089682 | 5/2018 |
| WO | 2018105549 | 6/2018 |
| WO | 2018116128 | 6/2018 |
| WO | 2018119077 | 6/2018 |
| WO | 2019210079 | 10/2019 |
| WO | 2019246412 | 12/2019 |
| WO | 2020036182 | 2/2020 |
| WO | 2020160839 | 8/2020 |
| WO | 2021134087 | 7/2021 |
| WO | 2022204622 | 9/2022 |

OTHER PUBLICATIONS

Bertera, J.H., et al., "Stabilized Retinal Mapping of Known Retinal Loci," Proceedings of the Annual Northeast Bioengineering Conference, IEEE, vol. Conf. 14, No. 1988, XP000010509 (Mar. 10, 1988).

Girish et al. Segmentation of Intra-Retinal Cysts From Optical Coherence Tomography Images Using a Fully Convolutional Neural Network Model. IEEE Journal of Biomedical and Health Informatics, vol. 23, No. 1, Jan. 2019, pp. 296-304 (Year: 2019).

Haglund, Erik, et al., "Multi-wavelength VCSEL arrays using high-contrast gratings," Proc. of SPIE vol. 10113, 7 pages (2017).

Huang, et al., "Optical coherence tomograph," Science, 254(5035):1178-1181 (Nov. 22, 1991).

Huang, Huimin, et al., "UNET 3+: A Full-Scale Connected UNET for Medical Image Segmentation," 5 pages, retrieved from https://arxiv.org/ftp/arxiv/papers/2004/2004.08790.pdf on Jun. 14, 2021.

International Search Report and Written Opinion for International Application No. PCT/US2020/070486, 21 pages (dated Nov. 20, 2020).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Khan, Zuhaib, et al., "High-brightness and high-speed vertical-cavity surface-emitting laser arrays," Optica, 7 (4):267-275 (Apr. 2020).

Kolb, Jan Philip, et al., "High-resolution retinal swept source optical coherence tomography with an ultra-wideband Fourier-domain mode-locked laser at MHz A-scan rates," Biomedical Optics Express, 9(1):120-130 (2018).

Mishra, Z., et al., "Automated Retinal Layer Segmentation Using Graph-based Algorithm Incorporating Deep-learning-derived Information," Sci Rep. 10(1):9541 (2020).

Moon, S., et al., "VCSEL-based swept source for low-cost optical coherence tomography", Biomedical Optics Express, 8(2):1110-1121 (Feb. 1, 2017).

Orr. Notal Vision—Home-Based Optical Coherence Tomograph (OCT). Slide deck (11 pgs.) (Nov. 9, 2017).

Pierro, L., et al., "Macular Thickness Interoperator and Intraoperator Reproducibility in Healthy Eyes Using 7 Optical Coherence Tomography Instruments," American Journal of Ophthalmology, 150(2): 199-204, XP027174249 (Aug. 1, 2010).

Sanghoon, Kim, et al., "Design and implementation of a low-cost, portable OCT system," 9(3):1232-1243 (Mar. 1, 2018).

WO 2020/036182 A1 machine translation from Japanese to English (132 pages).

Zara, J.M., et al., "Electrostatic micromachine scanning mirror for optical coherence tomography," Optics Letters, 28(8):628-630 (Apr. 15, 2003).

\* cited by examiner

OPTICAL COHERENCE TOMOGRAPHY PATIENT ALIGNMENT SYSTEM FOR HOME BASED OPHTHALMIC APPLICATIONS

RELATED APPLICATIONS

This application is a 371 national phase of PCT/US2020/070486, filed Sep. 2, 2020, published as WO 2021/134087 on Jul. 1, 2021, which claims the benefit under 35 U.S.C. § 119(e) of U.S. Provisional Patent Application No. 62/953,827, filed Dec. 26, 2019, and titled "OPTICAL COHERENCE TOMOGRAPHY PATIENT ALIGNMENT SYSTEM FOR HOME BASED OPHTHALMIC APPLICATIONS," which is incorporated, in its entirety, by this reference.

The subject matter of the present application is also related to PCT Patent Application No. PCT/US2019/038270, filed Jun. 20, 2019, entitled "MINIATURIZED MOBILE, LOW COST OPTICAL COHERENCE TOMOGRAPHY SYSTEM FOR HOME BASED OPHTHALMIC APPLICATIONS", published as WO 2019/246412, the entire disclosure of which is incorporated herein by reference.

BACKGROUND

The eye has a cornea and lens that refract light and form an image on the retina. The retina generates electrical signals in response to the image formed thereon, and these electrical signals are transmitted to the brain via the optic nerve. The fovea and macula of the retina have an increased density of cones in relation to other areas of the retina and provide crisp, sharp vision. Unfortunately, diseases of the retina can adversely affect vision even though other parts of the eye, such as the cornea and lens are healthy.

Retinal thickness can be used to diagnose and monitor the health of the retina. Many patients who have been diagnosed with retinal vascular diseases and other diseases or conditions have an elevated retinal thickness and take or are treated with medications. Macular edema is an example of elevated retinal thickness which is often related to other diseases such as diabetes. Macular edema can be related to other diseases such as age related macular degeneration, uveitis, blockage of retinal vasculature, and glaucoma, for example. It would be helpful to know quickly if a medication is not working or requires re-administration so that treatment can be modified accordingly and vision preserved. One approach used to measure the thickness of the retina is optical coherence tomography (OCT).

Unfortunately, many prior OCT systems are overly complex and expensive and not well-suited to monitoring retinal thickness regularly, such as on a weekly or daily basis. The prior standard of eye care involves a visit to a health care provider who measures retinal thickness, but such visits require scheduling and appointments and can become expensive, especially if conducted on a weekly or daily basis. Many of the prior OCT systems are not well-suited for in-home monitoring or mobile health care. Such prior systems typically weigh more than a person can easily carry and are not-well suited to travel with the patient. In addition, the prior OCT systems are more complex than would be ideal, and not well-suited for everyday use and hazards such as being dropped. The prior cost of an OCT system may exceed what a typical patient can afford. Furthermore, use of a prior OCT system may require a trained operator. For the above reasons, in-home monitoring of retinal thickness has not been adopted as the prior standard of care and prior care of patients with retinal disease can be less than ideal in many instances.

In light of the above, it would be helpful to have improved OCT systems and methods to measure thickness of the retina. Ideally, such systems would be compact, handheld, provide in-home monitoring, allow the patient to measure himself or herself, and be robust enough to be handled by a patient.

SUMMARY

The optical coherence tomography (OCT) system and methods disclosed herein allow in-home and mobile monitoring of retinal thickness. Although specific reference is made to measuring retinal thickness, the OCT system and methods disclosed herein will find application in many fields, such as microscopy, metrology, aerospace, astronomy, telecommunications, medicine, pharmaceuticals, dermatology, dentistry, and cardiology.

In some embodiments, the OCT system comprises an interferometer, a position sensor, a three-axis translation stage, and a processor configured with instructions to move at least a portion of the interferometer into alignment with the eye the three-axis translation stage in response to a measured position of the eye, which can facilitate alignment of the eye. In some embodiments, the OCT system comprises a fixation target coupled to a lens for the patient to view the fixation target through the lens, in which the lens comprises an optical element of the OCT interferometer and also transmits and OCT measurement beam. In some embodiments, the processor is configured with instructions to change a distance between the lens and the fixation target in order to compensate for a refractive error of the eye. The processor is configured with instructions to move the three-axis translation stage to align the lens laterally with the eye in response to a lateral position of the eye measured with the position sensor, and to position the lens at a target vertex distance from the cornea in response to the position sensor.

In some embodiments, the processor is configured with instructions to move the fixation target and the lens with the three-axis translation stage and to move the lens relative to the fixation target to compensate for the refractive error and maintain the vertex distance between the lens and the cornea. In some embodiments, the fixation target is moved toward the eye to correct for myopia while the vertex distance is maintained by moving the lens toward the fixation target. In some embodiments, the three-axis translation stage is moved with three actuators, and the lens is moved with a fourth actuator to maintain the vertex distance.

In some embodiments, the processor is configured with instructions to translate the fixation target and the lens to a plurality of positions corresponding to a plurality of refractive errors, and to measure the luminous intensity of the beam reflected from the eye at each of the plurality of locations. The processor can determine a distance between the lens and fixation target that corresponds to correction of the refractive error, in response to the luminous intensity at each of the plurality of locations. In some embodiments, the luminous intensity comprises a peak luminous intensity of the OCT beam measured at the detector without interference between a measurement arm and the reference arm. In some embodiments, the optical path difference (OPD) between a measurement arm and a reference arm of the OCT interferometer is adjusted with a fifth actuator. Alternatively, the OCT measurement beam may comprise a sufficient coherence length to perform the OCT measurement without adjusting the OPD when the lens and fixation target have been positioned for the OCT measurement with appropriate movement of the translation stage and the lens.

In some embodiments, an OCT system to measure a retina of an eye comprises an interferometer measure retinal data with an OCT measurement beam, a visual fixation target configured to move to a plurality of positions relative to the beam, and a position sensor to measure a position of the eye. A processor is operatively coupled to the interferometer, the fixation target and the position sensor, in which the processor is configured with instructions to move the fixation target to the plurality of positions and measure the position of the eye and the retinal data at each of the plurality of positions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
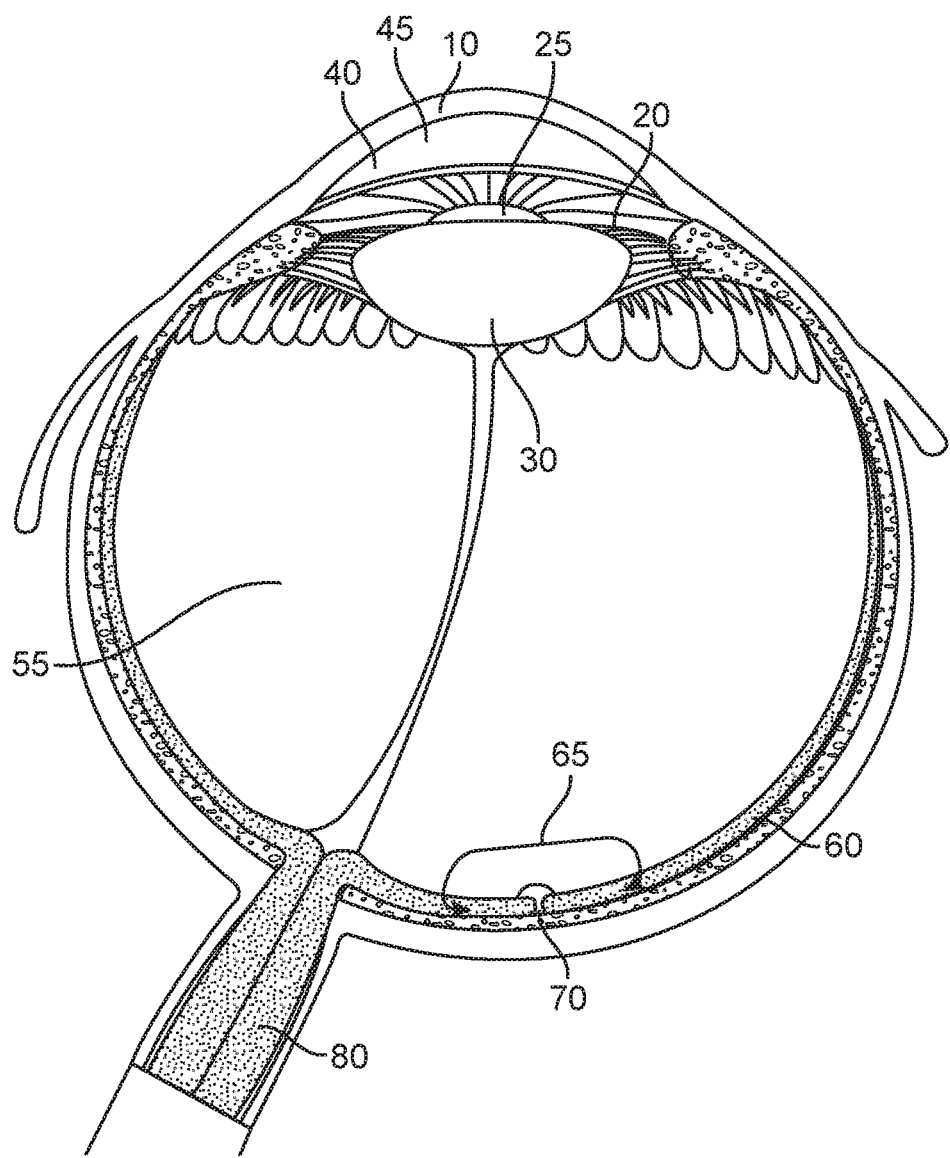
FIG. 1A shows a simplified diagram of the human eye.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. For example, although reference is made to measuring a thickness of a sample such as the retina, the methods and apparatus disclosed herein can be used to measure many types of samples, such as other tissues of the body and non-tissue material. While reference is made to generating maps of retinal thickness, the methods and apparatus disclosed herein can be used to generate images of retinal samples, such as cross sectional or tomographic images.

The presently disclosed systems and methods are well suited for incorporation with prior OCT approaches. The OCT interferometer may comprise one or more of a time domain OCT interferometer, a swept source OCT interferometer, spectral domain OCT interferometer or a multiple reflectance OCT interferometer. Although reference is made to a swept source VCSEL with a limited range of sweeping and the use of a plurality of VCSELs, the light source may comprise any suitable light source such as a MEMS tunable VCSEL capable of sweeping over a range of wavelengths from about 20 nm to about 100 nm or more. For embodiments using more than one swept light source such as a VCSEL, the plurality of swept light sources, e.g. VCSELs, may comprise any suitable number of swept light sources, such as 2, 3, 4, 5, 6, 7, 8, 9, 10, 11, 12 or more swept light sources such as VCSELs. Although reference is made to retinal thickness maps, in some embodiments, the OCT measurement systems and apparatus are configured to generate 3D tomographic images of the retina. In some embodiments, the 3D tomographic images of the retina comprise high resolution image of the retina, with a spatial resolution along the OCT measurement beam ("axial resolution") within a range from 2 to 10 micrometers, for example with resolution within a range from 5 to 10 nm.

The presently disclosed systems and methods can be configured in many ways. In some embodiments, the OCT system comprises a binocular device, in which one eye is measured and the other eye is presented with a stimulus such as a fixation stimulus. Alternatively, the OCT system may comprise a monocular device, in which one eye is measured at a time and only the measured eye is presented with a fixation stimulus, although the fellow eye may be covered with an occluder, for example.

The compact OCT system disclosed herein is well-suited for use with many prior clinical tests, such as retinal thickness measurements. In some cases, the OCT system is used by the patient, or by a health care provider. In many instances the patient can align himself with the system, although another user can align the patient with the system and take the measurement. In some embodiments, the OCT system is integrated with prior software and systems to provide additional information to healthcare providers, and can provide alerts in response to changes in retinal thickness. The alerts are optionally sent to the patient, caregiver, and health care providers when corrective action should be taken such as a change in medication, dosage, or a reminder to take medication.

As used herein, the term "retinal thickness (RT)" refers to a thickness of the retina between layers used to evaluate the thickness of a retina of a patient. The RT may correspond to a thickness of the retina between an anterior surface of the retina and external limiting membrane, for example.

As used herein, the term "retinal layer thickness (RLT)" refers to the thickness of one or more optically detectable layers of the retina. The optically detectable layers of the retina may comprise a thickness of the retina extending between the external limiting membrane and the retinal pigment epithelium, for example.

FIG. 1A shows a simplified diagram of the human eye. Light enters the eye through the cornea 10. The iris 20 controls the amount of light allowed to pass by varying the size of the pupil 25 that allows light to proceed to the lens 30. The anterior chamber 40 contains aqueous humor 45 which determines the intraocular pressure (IOP). The lens 30 focuses light for imaging. The focal properties of the lens are controlled by muscles which reshape the lens. Focused light passes through the vitreous chamber 50, which is filled with vitreous humor 55. The vitreous humor maintains the overall shape and structure of the eye. Light then falls upon the retina 60, which has photosensitive regions. In particular, the macula 65 is the area of the retina responsible for receiving light in the center of the visual plane. Within the macula, the fovea 70 is the area of the retina most sensitive to light. Light falling on the retina generates electrical signals which are passed to the optic nerve 80 and then to the brain for processing.

Several disorders give rise to reduced optical performance of the eye. In some cases, the intraocular pressure (TOP) is either too high or too low. This is caused, for instance, by too high or too low of a production rate of aqueous humor in the anterior chamber. In other cases, the retina is too thin or too thick. This arises, for instance, due to the buildup of fluid in the retina. Diseases related to an abnormal retinal thickness (RT) include glaucoma and macular edema, for example. In some cases, a healthy range of RT is from 175 µm thick to 225 µm thick. In general, abnormalities in either the TOP or the RT are indicative of the presence of many ophthalmological diseases. Additionally, the TOP or the RT vary in response to ophthalmological treatments or other procedures. Therefore, it is desirable to have a means to measure the TOP and/or RT for diagnosis of ophthalmological diseases and to assess the effectiveness of treatments for a given patient. In some cases, it is desirable to measure the thickness of one or more retinal layers, for example the thickness of a plurality of layers.

The systems and methods disclosed herein relate to the use of optical coherence tomography (OCT) to measure the RT or RLT at multiple points in time. For instance, a patient measures their RT or RLT at multiple time points to track the progression of an ophthalmological disease such as glaucoma or macular edema over time. As another example, a patient measures their RT or RLT at multiple time points to track their response to a pharmaceutical or other treatment. In some cases, the system produces an alert when one or more recent measurements of the RT or RLT deviate significantly from previous measurements. In some cases, the system alerts the patient or the patient's physician of the change. In some instances, this information is be used to schedule a follow-up appointment between the patient and physician to, for instance, attempt a treatment of an ophthalmological illness, discontinue a prescribed treatment, or conduct additional testing.

Figure 1B:
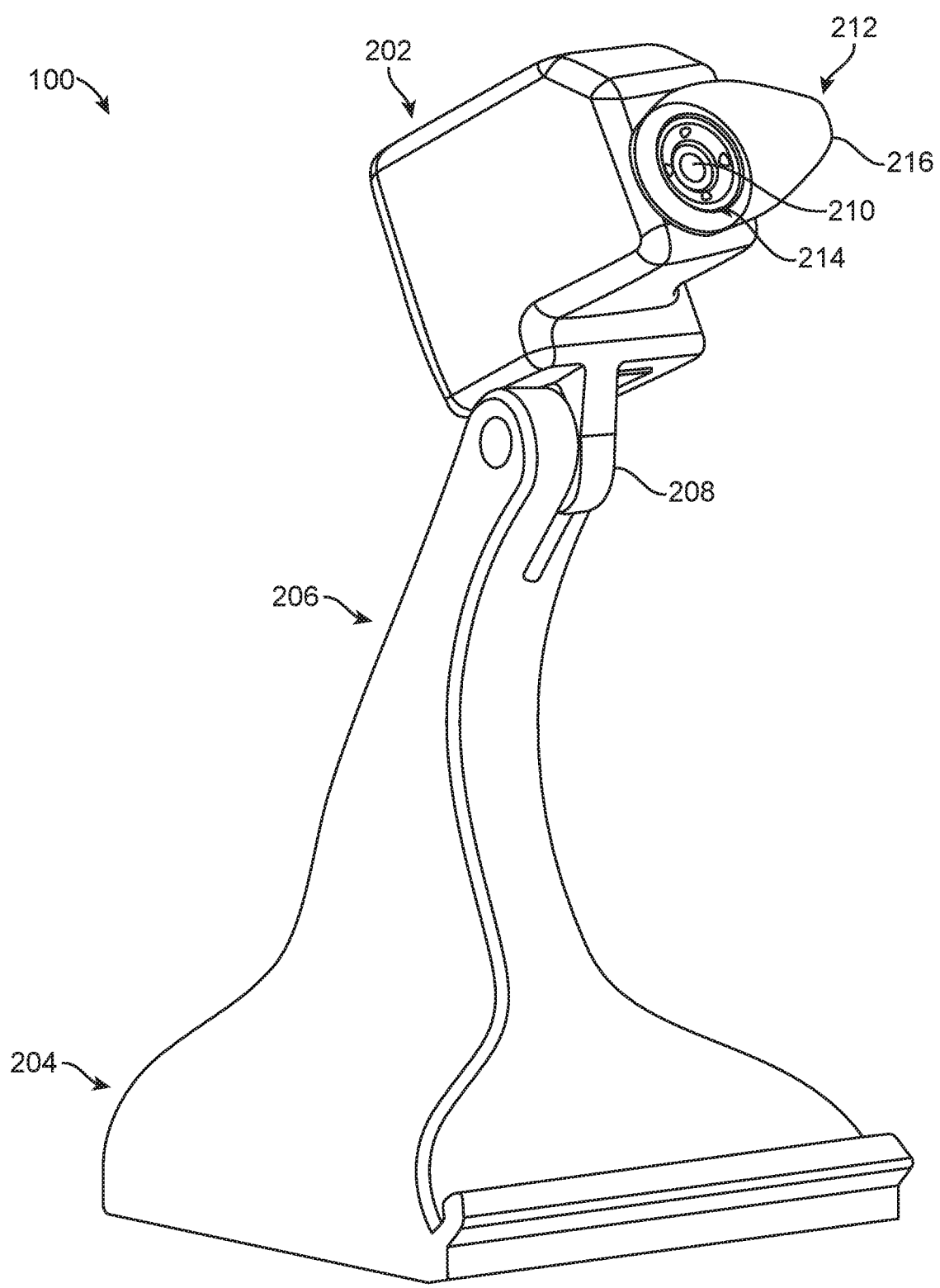
FIG. 1B shows a perspective view of a monocular optical coherence tomography (OCT) device for measuring eyes of a user, in accordance with some embodiments.

FIG. 1B shows a perspective view of a monocular optical coherence tomography (OCT) device 100 for measuring eyes of a user, in accordance with some embodiments. The OCT device 100 includes a head 202, a base 204, and a neck 206 therebetween. The head 202 is connected to the neck 206 by a coupling 208 that allows articulation of the head 202 in some embodiments. The head may be covered with a housing that encloses optical modules, scanning modules, and other related circuitry and modules to allow the OCT device 100 to measure eyes of a user, one eye at a time.

In some embodiments, the head 202 further includes a lens 210, an eyecup 212, and one or more LED lights 214. The lens 210 may be configured to direct one or more light sources from within the head 202 to focus on the retina of an eye. The eyecup 212 may be configured to locate the head of a patient, and thereby locate an eye of a patient for scanning and testing. The eyecup 212 may be rotatable, so that a protruding portion 216 may be located adjacent to an eye of a patient and extend along the side of the head (e.g., adjacent the patient's temple) when the patient's head is properly oriented to the OCT device 100. The eyecup 212 may be coupled to a sensor configured to detect the rotational orientation of the eyecup 212. In some embodiments, the OCT device 100 is configured to detect the rotational orientation of the eyecup 212 and thereby determine whether the patient has presented her right eye or left eye for scanning and measuring. More particularly, in some embodiments, the protruding portion 216 of the eyecup 212 may extend to be adjacent to either the right temple or the left temple of a patient, and thereby determine which eye of the patient is being measured. In some embodiments, eyecup 212 comprises a patient support. The patient support may comprise a headrest or a chinrest, either alternatively or in combination with the eyecup 212.

In some embodiments, a coupling 208 connects the head 202 to the neck 206 and allows a pivotal movement about the coupling. The coupling 208 may be any suitable coupling, which may be rigid, articulating, rotational, or pivotal according to embodiments. In some instances, the coupling includes a threaded fastener and a threaded nut to tighten the head against the neck in a desired orientation. The threaded nut may be operable by hand, and may comprise a knurled knob, a wing nut, a star nut, or some other type of manually operated tightening mechanism. The coupling may alternatively comprise any suitable member that allow adjustment of the angle of the head relative to the neck, and may include a cam, a lever, a detent, and may alternatively or additional include friction increasing structures, such as roughened surfaces, peaks and valleys, surface textures, and the like.

Figure 2:
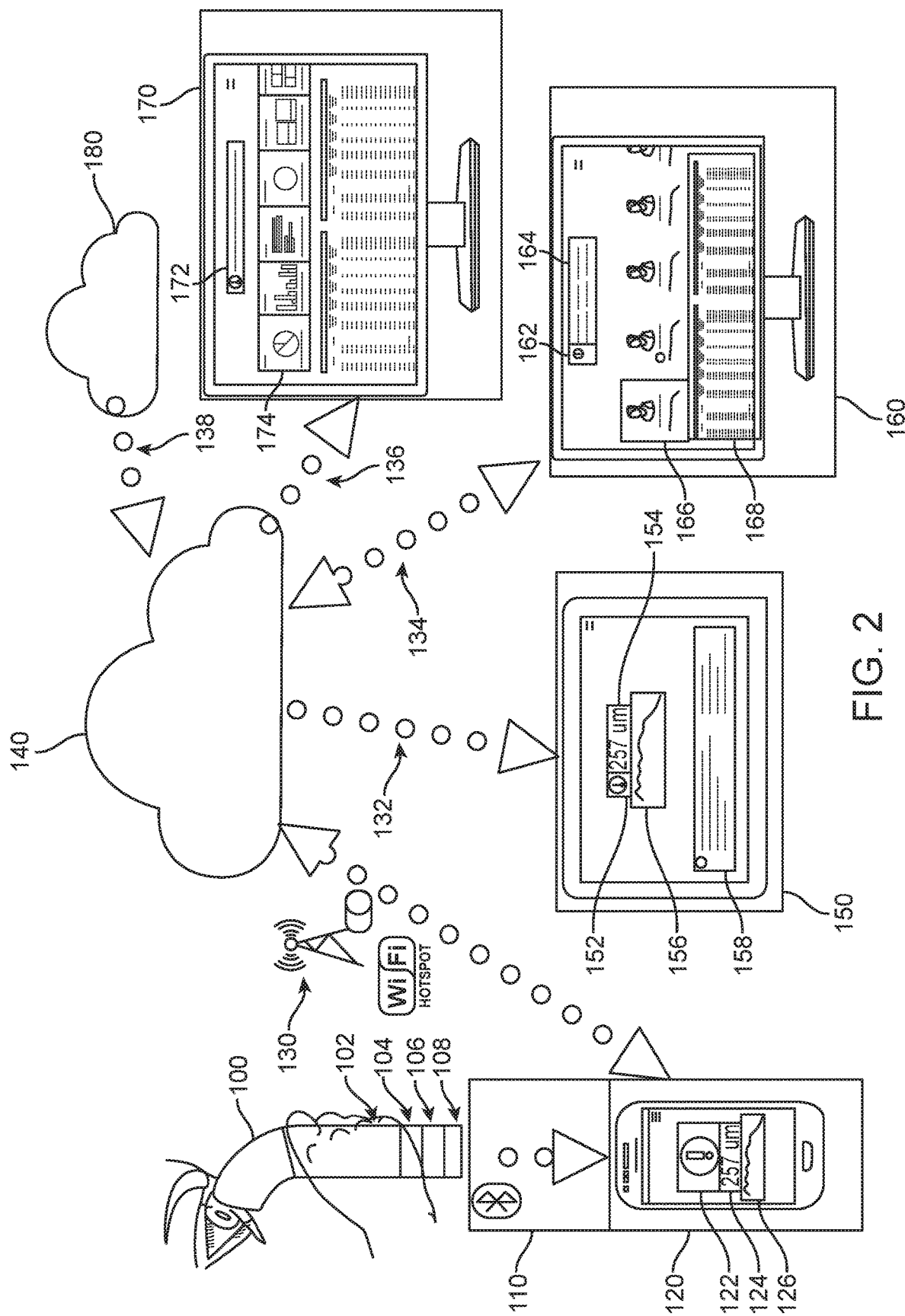
FIG. 2 shows a schematic of a system allowing a patient to measure retinal thickness (RT) at multiple time points and to communicate the results, in accordance with some embodiments.

FIG. 2 shows a schematic of a system allowing a patient to measure RT or RLT at multiple time points and to communicate the results, in accordance with some embodiments. The patient looks into a handheld OCT device 100 to obtain a measurement of the RT or RLT. In some embodiments, the handheld OCT device comprises optics 102, electronics 104 to control and communicate with the optics, a battery 106, and a transmitter 108. In some instances, the transmitter is a wired transmitter. In some cases, the transmitter is a wireless transmitter. In some cases, the handheld OCT device 100 communicates the results via a wireless communication channel 110 to a mobile patient device 120 on the patient's smartphone or other portable electronic device. In some cases, the wireless communication is via Bluetooth communication. In some embodiments, the wireless communication is via Wi-Fi communication. In other embodiments, the wireless communication is via any other wireless communication known to one having skill in the art.

In some cases, the results are fully processed measurements of the RT. In some cases, all processing of the OCT data is performed on the handheld OCT device. For instance, in some embodiments, the handheld OCT device includes hardware or software elements that allow the OCT optical waveforms to be converted into electronic representations. In some cases, the handheld OCT device further includes hardware or software elements that allow processing of the electronic representations to extract, for instance, a measurement of the RT.

In some cases, the results are electronic representations of the raw optical waveforms obtained from the OCT measurement. For instance, in some embodiments, the handheld OCT device includes hardware or software elements that allow the OCT optical waveforms to be converted into electronic representations. In some cases, these electronic representations are then passed to the mobile patient device for further processing to extract, for instance, a measurement of the RT.

In some cases, the patient receives results and analysis of the RT or RLT measurement on the patient mobile app. In some embodiments, the results include an alert 122 alerting the patient that the results of the measurement fall outside of a normal or healthy range. In some cases, the results also include a display of the measured value 124. For instance, in some cases a measurement of the RT or RLT produces a result of 257 µm. In some instances, this result falls outside of a normal or healthy range. This causes the system to produce an alert and to display the measured value of 257 µm on the patient mobile app. In some embodiments, the alert is transmitted to a healthcare provider, such as a treating physician. In some embodiments, the results also include a chart 126 showing a history of the patient's RT or RLT over multiple points in time.

In some instances, the patient mobile device communicates the results of the measurement via a communication means 130 to a cloud-based or other network-based storage and communications system 140. In some embodiments, the communication means is a wired communication means. In some embodiments, the communication means is a wireless communication means. In some cases, the wireless communication is via Wi-Fi communication. In other cases, the wireless communication is via a cellular network. In still other cases, the wireless communication is via any other wireless communication known to one having skill in the art. In specific embodiments, the wireless communication means is configured to allow transmission to or reception from the cloud-based or other network-based storage and communications system.

Once stored in the cloud, the results are then transmitted to other devices, in specific embodiments. In some cases, the results are transmitted via a first communication channel 132 to a patient device 150 on the patient's computer, tablet, or other electronic device. In some embodiments, the results are transmitted via a second communication channel 134 to a physician device 160 on the patient's physician's computer, tablet, or other electronic device. In some instances, the results are transmitted via a third communication channel 136 to an analytics device 170 on another user's computer, tablet, or other electronic device. In some embodiments, the results are transmitted via a fourth communication channel 138 to a patient administration system or hospital administration system 180. In some cases, each of the devices has appropriate software instructions to perform the associate function as described herein.

In specific embodiments, the first communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is via any other wired or wireless communication known to one having skill in the art. In some embodiments, the first communication channel is configured to allow transmission to or reception from the cloud-based or other network-based storage and communications system. In some cases, the first communication channel is configured to only allow reception from the cloud-based or other network-based storage and communications system.

In some cases, the second communication channel is a wired communication channel or a wireless communication channel. In some instances, the communication is via Ethernet. In specific embodiments, the communication is via a local area network (LAN) or wide area network (WAN). In other embodiments, the communication is via Wi-Fi. In still other embodiments, the communication is via any other wired or wireless communication known to one having skill in the art. In some cases, the second communication channel is configured to allow transmission to or reception from the cloud-based or other network-based storage and communications system. In some embodiments, the second communication channel is configured to only allow reception from the cloud-based or other network-based storage and communications system.

In specific cases, the third communication channel is a wired communication channel or a wireless communication channel. In some instances, the communication is via Ethernet. In other instances, the communication is via a local area network (LAN) or wide area network (WAN). In still other instances, the communication is via Wi-Fi. In yet other instances, the communication is via any other wired or wireless communication known to one having skill in the art. In some embodiments, the third communication channel is configured to allow transmission to or reception from the cloud-based or other network-based storage and communications system. In some cases, the third communication channel is configured to only allow reception from the cloud-based or other network-based storage and communications system.

In some embodiments, the fourth communication channel is a wired communication channel or a wireless communication channel. In some cases, the communication is via Ethernet. In other cases, the communication is via a local area network (LAN) or wide area network (WAN). In still other cases, the communication is via Wi-Fi. In yet other cases, the communication is any other wired or wireless communication known to one having skill in the art. In some instances, the fourth communication channel is configured to allow transmission to or reception from the cloud-based or other network-based storage and communications system. In other cases, the fourth communication channel is configured to only allow reception from the cloud-based or other network-based storage and communications system.

A determination of the RT or RLT can be performed at many locations. For instance, a determination of the RT or RLT is performed on the handheld OCT device. In some cases, a determination of the RT or RLT is performed at a location near to the handheld OCT device, such as by a smartphone or other portable electronic device. In some embodiments, a determination of the RT or RLT is performed on the cloud-based storage and communications system. In some instances, the handheld OCT device is configured to compress measurement data and transmit the compressed measurement data to the cloud-based storage and communications system. Alternatively or in combination, other components of the OCT system, such as a mobile device operatively coupled to the OCT device, can be configured to compress the measurement data and transmit the compressed measurement data to the cloud-based storage and communication system, for example.

In some embodiments, the patient receives results and analysis of the RT or RLT measurement on the patient device 150. In some instances, the results include an alert 152 alerting the patient that the results of the measurement fall outside of a normal or healthy range. In some cases, the results also include a display of the measured value 154. For instance, in some cases, a measurement of the RT or RLT produces a result of 257 µm. This result falls outside of a normal or healthy range. In some cases, this causes the system to produce an alert and to display the measured value of 257 µm on the patient app. In specific cases, the results also include a chart 156 showing a history of the patient's RT or RLT over multiple points in time. In some cases, the patient device also displays instructions 158 for the patient to follow. In some instances, the instructions instruct the patient to visit their physician. In some embodiments, the instructions include the patient's name, date of most recent RT or RLT measurement, and next scheduled visit to their physician. In other cases, the instructions include more information. In still other cases, the instructions include less information.

In some embodiments, the patient's physician receives the results and analysis of the RT or RLT measurement on the physician device 160. In some instances, the results include an alert 162 alerting the physician that the results of the measurement fall outside of a normal or healthy range. In some cases, the results also include an alert 164 informing the physician that the patient's measurement falls outside of a normal or healthy range. In some embodiments, the alert includes a suggestion that the physician call the patient to schedule an appointment or to provide medical assistance. In some embodiments, the results also include a display 166 showing the most recent measurements and historical measurements for each of the physician's patients. For instance, in some instances, a measurement of the RT or RLT produces a result of 257 µm. This result falls outside of a normal or healthy range. In some cases, this causes the system to produce an alert and to display the measured value of 257 µm on the physician app. In specific cases, the physician device also displays contact and historical information 168 for each of the physician's patients.

In some embodiments, the other user receives results and analysis of the RT or RLT measurement on the analytics device 170. In some instances, the other user is a researcher investigating the efficacy of a new form of treatment. In other cases, the other user is an auditor monitoring the outcomes of a particular physician or care facility. To protect the patient's privacy, in some cases the analytics device is restricted to receive only a subset of a given patient's information. For instance, the subset is restricted so as not to include any personally identifying information about a given patient. In some cases, the results include an alert 172 alerting that a large number of abnormal or unhealthy measurements have been obtained in a specific period of time. In some cases, the results include one or more graphical representations 174 of the measurements across a population of patients.

In some cases, the results and analysis on the analytics device comprise disease information such as a physician-confirmed diagnosis. In some cases, the results and analysis comprise anonymized patient data such as age, gender, genetic information, information about the patient's environment, smoking history, other diseases suffered by the patient, etc. In some cases, the results and analysis comprise anonymized treatment plans for the patient, such as a list of prescribed medications, treatment history, etc. In some cases, the results and analysis comprise measurement results, such as the results of an RT or RLT measurement, a visual function test, or the patient's compliance with a course of treatment. In some cases, the results and analysis comprise data from an electronic medical record. In some cases, the results and analysis comprise diagnostic information from visits to a patient's medical provider, such as the results of an OCT scan acquired by the patient's medical provider.

In some embodiments, the patient's clinical, hospital, or other health provider receives results and analysis of the RT or RLT measurement on the patient administration system or hospital administration system 180. In some cases, this system contains the patient's electronic medical record. In some cases, the results and analysis provide the patient's health provider with data allowing the provider to update the treatment plan for the patient. In some instances, the results and analysis allow the provider to decide to call the patient in for an early office visit. In some instances, the results and analysis allow the provider to decide to postpone an office visit.

In some embodiments, one or more of the patient device, physician device, and analytics device includes a software app comprising instructions to perform the functions of the patient device, physician device, or analytics device, respectively, as described herein.

Figure 3A:
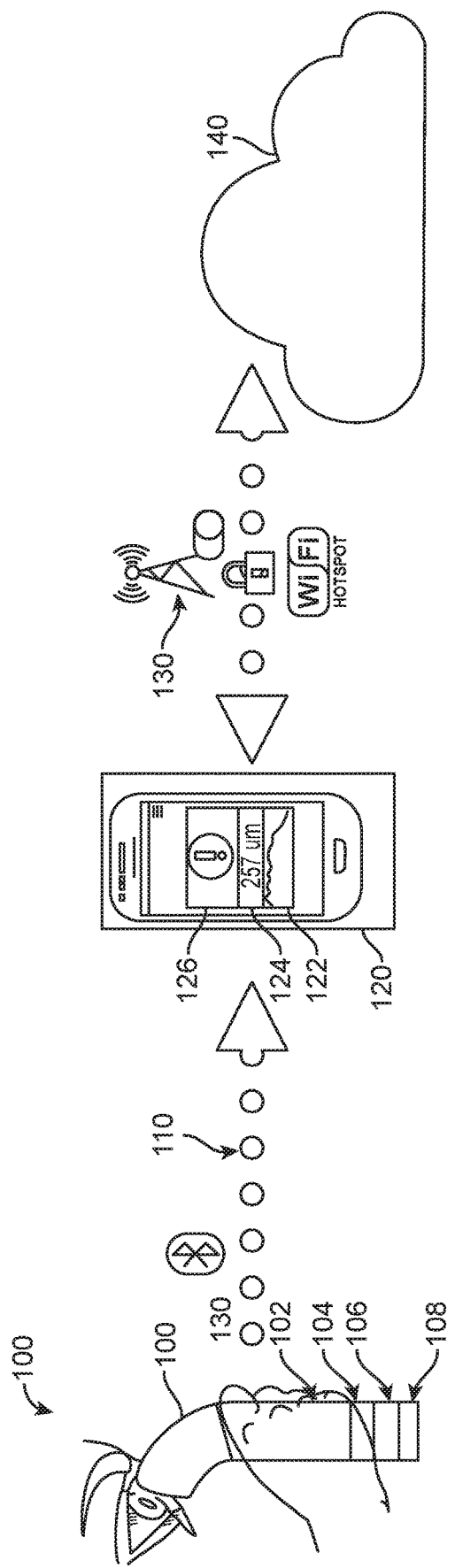
FIG. 3A shows a handheld optical coherence tomography device utilizing Bluetooth communication, in accordance with some embodiments.

FIG. 3A shows a handheld OCT device utilizing short-range wireless communication, in accordance with some embodiments. In some embodiments, the handheld OCT device 100 comprises optics 102, electronics to control and communicate with the optics 102, a battery 106, and a wireless transmitter 108. In some cases, the wireless transmitter is a Bluetooth transmitter. In some instances, the results from one or more RT or RLT measurements are stored on the handheld OCT device until an authorized user, such as the patient or another person designated by the patient, opens the patient mobile device on a smartphone or other portable electronic device. Once opened, the patient mobile device establishes wireless communication with the handheld OCT device. In some cases, the communication is via a Bluetooth wireless communication channel 110. In some instances, the handheld OCT device communicates the results via the Bluetooth channel to a mobile patient device 120 on the patient's smartphone or other portable electronic device.

In some instances, the results include an alert 122 alerting the patient that the results of the measurement fall outside of a normal or healthy range. In specific embodiments, the results also include a display of the measured value 124. For instance, a measurement of the RT or RLT produces a result of 257 μm in some cases. This result falls outside of a normal or healthy range. In some cases, this causes the system to produce an alert and to display the measured value of 257 μm on the patient mobile app. In specific embodiments, the results also include a chart 126 showing a history of the patient's RT or RLT over multiple points in time.

In some cases, the patient mobile device communicates the results of the measurement via a wireless communication means 130 to a cloud-based or other network-based storage and communications system 140. In some instances, the wireless communication is via Wi-Fi communication. In other cases, the Wi-Fi communication is via a secure Wi-Fi channel. In still other cases, the wireless communication is via a cellular network. In specific embodiments, the cellular network is a secure cellular network. In other embodiments, the transmitted information is encrypted. In some cases, the communication channel is configured to allow transmission to or reception from the cloud-based or other network-based storage and communications system. In some cases, data is stored on the smartphone or other portable electronic device until the smartphone or other portable electronic device connects to a Wi-Fi or cellular network.

In some cases, the patient mobile device has a feature which notifies the patient or another person designated by the patient when too much time has elapsed since the patient mobile device was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

Figure 3B:
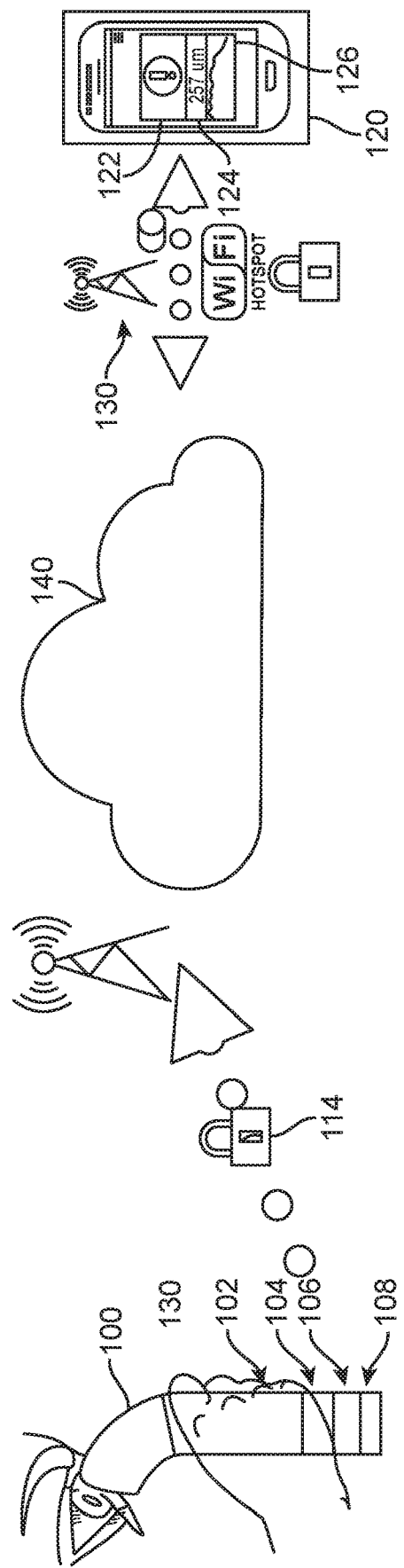
FIG. 3B shows a handheld OCT device utilizing the Global System for Mobile Communications (GSM), in accordance with some embodiments.

FIG. 3B shows a handheld OCT device capable of communicating directly with a cloud-based storage and communication system without reliance on a user device such as a smartphone, in accordance with some embodiments. In some embodiments, the handheld OCT device 100 comprises optics 102, electronics to control and communicate with the optics 102, a battery 106, and a wireless transmitter 108. In some cases, the wireless transmitter is a GSM transmitter. In some instances, the results from one or more RT or RLT measurements are stored on the handheld OCT device. In some cases, the GSM transmitter establishes wireless communication with a cloud-based or other network-based storage and communications system 140 via a wireless communication channel 114. In specific cases, the wireless communication is via a GSM wireless communication channel. In other embodiments, the system utilizes third generation (3G) or fourth generation (4G) mobile communications standards. In such cases, the wireless communication is via a 3G or 4G communication channel.

In specific embodiments, the patient mobile device 120 receives the results of the measurement via a wireless communication means 130 from the cloud-based or other network-based storage and communications system 140. In some cases, the wireless communication is via Wi-Fi communication. In some cases, the Wi-Fi communication is via a secure Wi-Fi channel. In other cases, the wireless communication is via a cellular network. In some cases, the cellular network is a secure cellular network. In specific instances, the transmitted information is encrypted. In some embodiments, the communication channel is configured to allow transmission to or reception from the cloud-based or other network-based storage and communications system.

Once obtained from the cloud-based or other network-based storage and communications system, the results of the RT or RLT measurement are viewed in the patient mobile app, in some instances. In some cases, the results include an alert 122 alerting the patient that the results of the measurement fall outside of a normal or healthy range. In some instances, the results also include a display of the measured value 124. For instance, in some cases a measurement of the RT or RLT produces a result of 257 μm. This result falls outside of a normal or healthy range. In specific embodiments, this causes the system to produce an alert and to display the measured value of 257 μm on the patient mobile app. In some embodiments, the results also include a chart 126 showing a history of the patient's RT or RLT over multiple points in time.

In some cases, the patient mobile device has a feature which notifies the patient or another person designated by the patient when too much time has elapsed since the patient mobile device was last opened. For instance, in some cases this notification occurs because the patient has not acquired measurements of the RT or RLT as recently as required by measuring schedule set by their physician or other healthcare provider. In other cases, the notification occurs because the handheld OCT device has been storing the results of too many measurements and needs to transmit the data to the patient's smartphone. In specific embodiments, the patient mobile device communicates with the cloud-based or other network-based storage and communications system to display a complete set of patient data.

In some cases, the handheld OCT device comprises both a short-range transmitter and a GSM, 3G, or 4G transmitter. In some instances, the short-range transmitter is a Bluetooth transmitter. In some cases, the handheld OCT device communicates directly with the patient mobile device on a smartphone or other portable electronic device through the Bluetooth wireless communication channel. In some embodiments, the handheld OCT also communicates with the cloud-based or other network-based storage and communications system through the GSM, 3G, or 4G wireless communication channel. In specific cases, the cloud-based system then communicates with the patient mobile device through a Wi-Fi, cellular, or other wireless communication channel. Alternatively, the Bluetooth transmitter is built into a docking station. In some instances, this allows for the use of older devices for patients who lack a smartphone. In some cases, the docking station also includes a means for charging the battery of the handheld OCT device.

In some cases, the handheld OCT device of FIGS. 3A and 3B is configured to be held in close proximity to the eye. For instance, in specific embodiments, the device is configured to be held in front of the eye with the detector at a distance of no more than 200 mm from the eye. In other embodiments, the devices are configured to be held in front of the eye with the detector at a distance of no more than 150 mm, no more than 100 mm, or no more than 50 mm from the eye. In specific instances, the handheld OCT devices further comprise housing to support the light source, optical elements, detector, and circuitry. In some cases, the housing is configured to be held in a hand of a user. In some cases, the user holds the devices in front of the eye to direct the light beam into the eye. In some instances, the devices include a sensor to measure which eye is being measured. For instance, in specific embodiments, the devices include an accelerometer or gyroscope to determine which eye is measured in response to an orientation of the housing. The devices optionally include an occlusion structure coupled to the housing and the sensor that determines which eye is measured. The occlusion structure occludes one eye while the other eye is measured. In some cases, the devices include a viewing target to align the light beams with a portion of the retina. For instance, in specific embodiments, the devices include a viewing target to align the light beams with a fovea of the eye. In some cases, the viewing target is a light beam. In some cases, the viewing target is a light emitting diode. In other cases, the viewing target is a vertical cavity surface emitting laser (VCSEL). In still further cases, the viewing target is any viewing target known to one having skill in the art.

The optical components described herein are capable of being miniaturized so as to provide the handheld OCT device with a reduced physical size and mass, as described herein, as will be appreciated by one of ordinary skill in the art.

In many embodiments, the handheld OCT devices of FIGS. 3A and 3B are small enough and light enough to be easily manipulated with one hand by a user. For instance, in many embodiments, the device has a mass within a range from about 100 grams to about 500 grams. In many embodiments, the device has a mass within a range from about 200 grams to about 400 grams. In many embodiments, the device has a mass within a range from about 250 grams to about 350 grams. In specific embodiments, the device has a maximum distance across within a range from about 80 mm to about 160 mm. In specific embodiments, the device has a maximum distance across within a range from about 100 mm to about 140 mm. In specific embodiments, the device has a width within a range from about 110 mm to about 130 mm. In some embodiments, the maximum distance across comprises a length. In some embodiments, the device has a width less than its length. In specific embodiments, the device has a width within a range from about 40 mm to about 80 mm. In specific embodiments, the device has a width within a range from about 50 mm to about 70 mm. In specific embodiments, the device has a width within a range from about 55 mm to about 65 mm.

Figure 4:
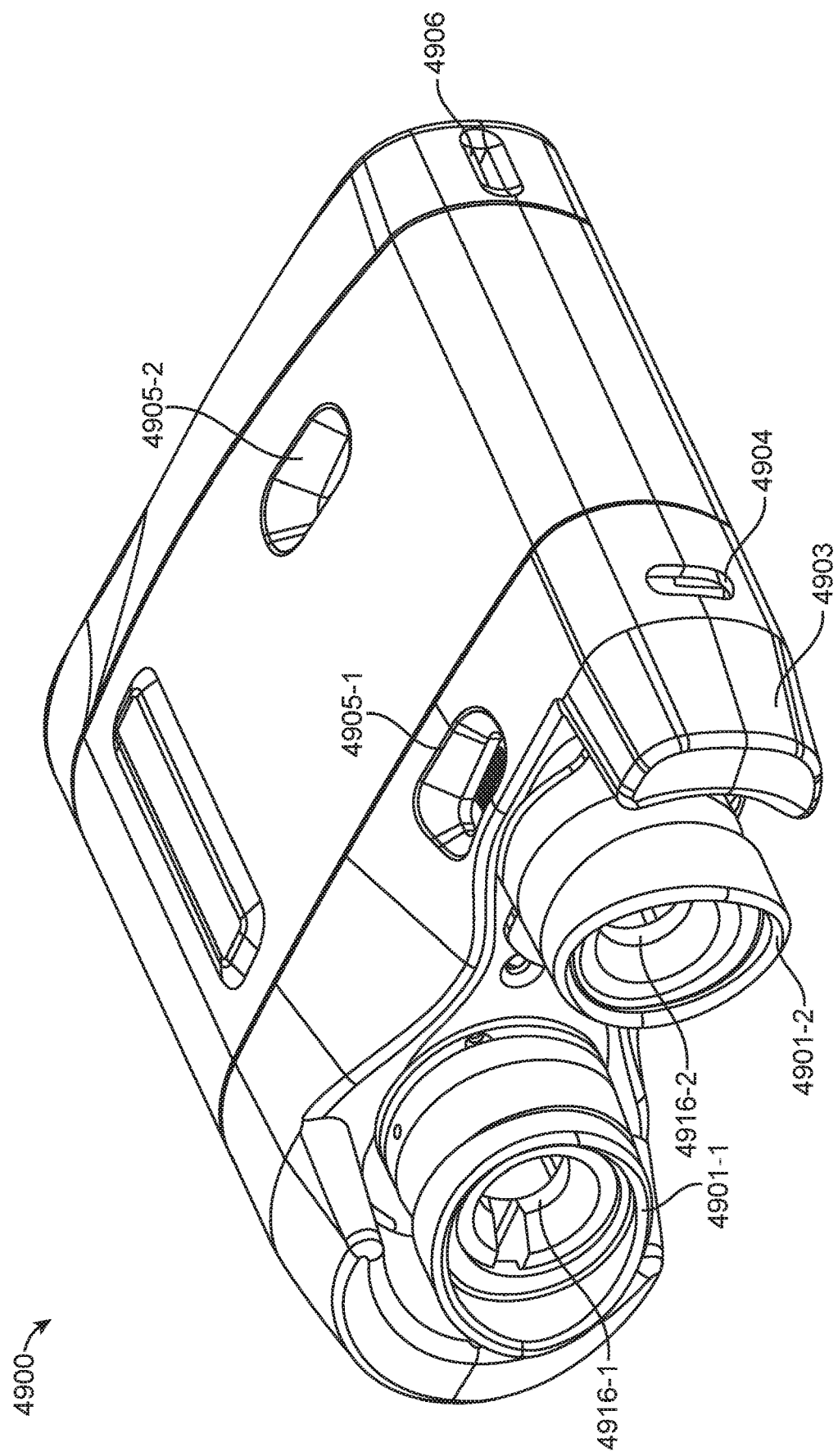
FIG. 4 shows a perspective view of a binocular OCT device for measuring eyes of a user, in accordance with some embodiments.

FIG. 4 shows a perspective view of a binocular OCT device 4900 for measuring eyes of a user, in accordance with some embodiments. The binocular OCT device 4900 comprises a first adjustable lens 4916-1 that is optically coupled to an OCT measurement system and a first fixation target configured within a handheld unit body 4903 (e.g., a housing), both of which are hidden from view in this figure. Similarly, a second adjustable lens 4916-2 may be optically coupled to the OCT measurement system and a second fixation target (hidden). The first adjustable lens 4916-1 may be part of a first free space optics that is configured to provide a fixation target and measure a retinal thickness of the user's eye, whereas the second adjustable lens 4916-2 may be part of a second free space optics that is configured to only provide a fixation target so as to reduce a number of components in the binoculars OCT device 4900. For instance, while both free space optics provide the user with a fixation target, only one of the free space optics is used to measure the retinal thickness as the binocular OCT device 4900 may be turned upside down, i.e. inverted, after the user measures a first eye such that the user may measure the other eye.

The binocular OCT device 4900, in this embodiment, comprises an interpupillary distance (IPD) adjustment mechanism 4905 that is accessible on the exterior of the handheld unit body 4903. In this embodiment, the IPD adjustment mechanism 4905 comprises two components, a first component 4905-1 that adjusts the distance between the lenses 4916-1 and 4916-2 to match the IPD of a user's pupils when the user places the binocular OCT device 4900 front of the user's eyes when the eye cups 4901-1 and 4901-2 rest on the user's face.

This IPD can be set by a healthcare professional, and locked into position for the user to measure retinal thickness at home. Alternatively, the IPD can be user adjustable. A switch 4904 may be used to adjust the lenses 4916-1 and 4916-2 to match a user's refraction, i.e. eyeglass prescription. Alternatively, a mobile device, such as a tablet can be used program the refraction of each eye of the patient. For example, the user may fixate on the first fixation target with one eye and a second fixation target with another eye, and the movable lenses adjusted to the user's refraction. The switch 4904 may selectively adjust the assemblies of the lenses 4916-1 and 4916-2 within the handheld unit body 4903 to change the positioning of the lenses 4916-1 and 4916-2. These positions can be input into the device by a health care professional, and stored in a processor along with an orientation from an orientation sensor as described herein. The device can be inverted and the process repeated. Alternatively or additionally, the prescription for each eye can be stored in the processor and the lenses adjusted to the appropriate refraction for each eye in response to the orientation of the orientation sensor.

Both of the components 4905-1 and 4905-5 may be implemented as one or more wheels that the health care professional manually rotates. Alternatively, the IPD adjustment mechanism 4905 may be motorized. In this regard, the components 4905-1 and 4905-5 may be configured as directional switches that actuate motors within the handheld unit body 4903 to rotate gears within the handheld unit body 4903 based on the direction in which the user directs the switch.

The switch 4904 can be used to adjust the focusing of the binocular OCT device 4900. For example, because the focal change effected by adjustment of the lenses 4916-1 and 4916-2 can be measured in a customary unit of refractive power (e.g., the Diopter) by adjustment of the lenses 4916-1 and 4916-2. The Diopter switch 4906 may also comprise a directional switch that actuates a motor within the handheld unit body 4903 to rotate gears within the handheld unit body 4903 based on the direction in which the healthcare professional directs the switch to adjust the refractive power of the binocular OCT device 4900. As the binocular OCT device 4900 may comprise an electronic device, the binocular OCT device 4900 may comprise a power switch to control powering of the binocular OCT device 4900.

Each of the eyecups 4901-1 and 4901-2 can be threadedly mounted and coupled to the housing to allow adjustment of the position of the eye during measurements. Work in relation to the present disclosure suggests that the eyecups can be adjusted by a healthcare professional and locked in place to allow sufficiently reproducible positioning of the eye for retinal thickness measurements as described herein. Alternatively or in combination, an eye position sensor, such as a Purkinje image sensor can be used to determine a distance from the eye to the OCT measurement system.

The binocular OCT device 4900 may comprise appropriate dimensions and weight for in home measurements and for the user to take the binocular OCT system on trips. For example, the binocular OCT system may comprise a suitable length, a suitable width and a suitable height. The length can extend along an axis corresponding to the users viewing direction. The length can be within a range from about 90 mm to about 150 mm, for example about 130 mm. The width can extend laterally to the length and can be within a range from about 90 mm to about 150 mm for example about 130 mm. The height can be within a range from about 20 mm to about 50 mm, for example. The weight of the binocular OCT system can be within a range from about 1 pound to two pounds, e.g. 0.5 kg to about 1 kg.

The binocular OCT device 4900 can be configured to be dropped. For example, the binocular OCT device can be configured to be dropped from a height of about 30 cm and still function so as to perform retinal thickness measurements accurately, e.g. with a change in measured retinal thickness of no more than the repeatability of the measurements. The binocular OCT system can be configured to be dropped from a height of about 1 meter without presenting a safety hazard, for example from glass breaking.

Figure 5:
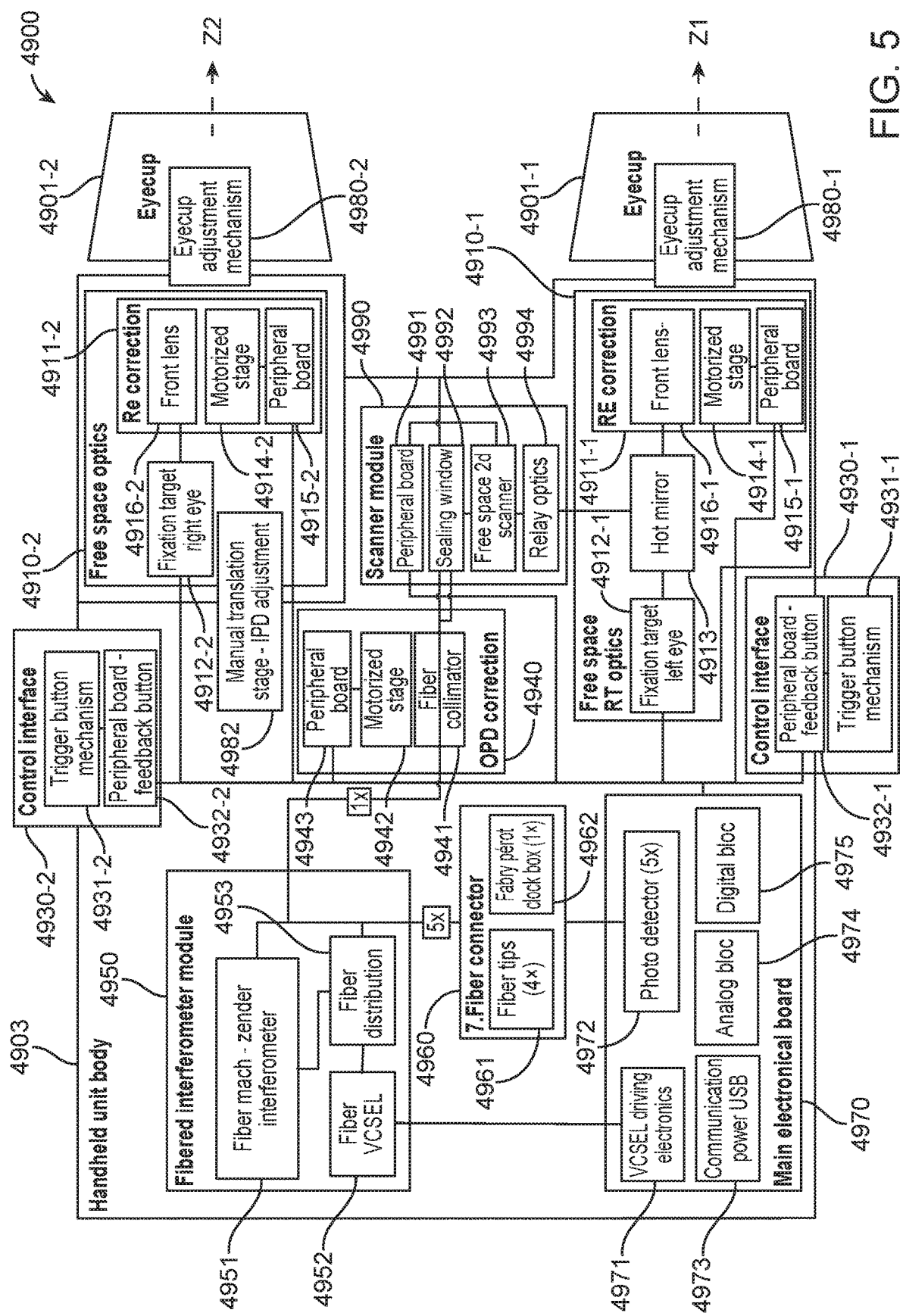
FIG. 5 shows a block diagram of the binocular OCT device illustrating various components within the handheld unit body, in accordance with some embodiments.

FIG. 5 shows a block diagram of the binocular OCT device 4900 illustrating various components within the handheld unit body 4903, in accordance with some embodiments. For instance, the binocular OCT device 4900 comprises free space optics 4910-1 and 4910-2. Each of the free space optics 4910-1 and 4910-2 comprises a fixation target 4912 for its respective eye that allows the user to fixate/gaze on the target while the user's retinal thickness is being measured, and to allow fixation with the other eye, so as to provide binocular fixation. The fixation target may comprise an aperture back illuminated with a light source such as an LED, (e.g., a circular aperture to form a disc shaped illumination target, although a cross or other suitable fixation stimulus may be used. The free space optics 4910-1 and 4910-2 may also comprise refractive error (RE) correction modules 4911-1 and 4911-2, respectively, that comprises the lenses 4916-1 and 4916-2, respectively. These lenses can be moved to preprogrammed positions corresponding to the refractive error of the appropriate eye. A peripheral board 4915-1 and 4915-2 in the free space optics modules 4910-1 and 4910-2 provides electronic control over a motorized stage 4914-1 and 4914-2, respectively to correct for the refractive error of the respective eye viewing the fixation target of the binocular OCT device 4900.

As discussed herein, the binocular OCT device 4900 may comprise eye cups 4901-1 and 4901-2 that may be used to comfortably rest the binocular OCT device 4900 on the user's face. They may also be configured to block out external light as the user gazes into the binocular OCT device 4900. The eye cups 4901 may also comprise eye cup adjustment mechanisms 4980-1 and 4980-2 that allow the health care professional and optionally the user to move the eye cups 4901-1 and 4901-2 back and forth with respect to the handheld unit body 4903 to comfortably position the eye cups on the user's face and appropriately position each eye for measurement.

In some embodiments, the binocular OCT device 4900 comprises a fibered interferometer module 4950 that comprises a single VCSEL or a plurality of VCSELs 4952. The one or more VCSELs 4952 are optically coupled to a fiber distribution module 4953, which is optically coupled to fiber Mach-Zender interferometer 4951. With embodiments comprising a plurality of VCSELs 4952, the VCSELS may each comprise a range of wavelengths different from other VCSEL 4952 in the plurality in order to extend a spectral range of light. For example, each VCSEL 4952 may pulse laser light that is swept over a range of wavelengths for some duration of time. The swept range of each VCSEL 4952 may partially overlap an adjacent swept range of another VCSEL 4952 in the plurality as described herein. Thus, the overall swept range of wavelengths of the plurality of VCSELs 4952 may be extended to a larger wavelength sweep range. Additionally, the firing of the laser light from the plurality of VCSELs 4952 may be sequential. For example, a first VCSEL of the plurality of VCSELs 4952 may sweep a laser pulse over a first wavelength for some duration. Then, a second VCSEL of the plurality of VCSELs 4952 may sweep a laser pulse over a second wavelength for some similar duration, then a third, and so on.

The laser light from the VCSELs 4952 is optically transferred to the fiber distribution module 4953, where a portion of the laser light is optically transferred to a fiber connector 4960 for analysis in a main electronic board 4970. The fiber connector 4960 may connect a plurality of optical fibers from the fiber distribution module 4953 to the fiber connector module 4960. Another portion of the laser light is optically transferred to an optical path distance correction (OPD) module 4940 and ultimately to the free space retinal thickness optics 4910-1 for delivery to a user's eye and measurement of the user's eye with a portion of the measurement arm of the Mach-Zender interferometer. For example, the OPD correction module 4940 may comprise a peripheral board 4943 that is controlled by the main electronic board 4970 to actuate a motorized stage 4942 to change the optical path distance between the user's eye, a coupler of the Mach-Zender interferometer and the one or more VCSELs 4952. The OPD correction module 4940 may also comprise a fiber collimator 4941 that collimates the laser light from the VCSELs 4952 before delivery to the user's eye, and the fiber collimator can be translated with the OPD correction module 4940.

A controller interface 4930 may be used to receive user inputs to control the binocular OCT measurement system. The controller interface may comprise a first controller interface 4930-1 and a second controller interface 4930-2. The controller interface 4930 may comprise a trigger button mechanism that allows a user to initiate a sequence of steps to align the eye and measure the retina as described herein.

Additionally, the binocular OCT device 4900 may comprise a scanner module 4990 that scans the laser light from the one or more VCSELs 4952 in a pattern (e.g., a stop and go trajectory, a star trajectory, a continuous trajectory, and/or a Lissajous trajectory, each of which is explained in greater detail below). For example, a peripheral board 4991 of the scanner module 4990 may be communicatively coupled to the main electronic board 4970 to receive control signals that direct the scanner module 4990 to scan the pulsed laser light from the VCSELs 4952 in a pattern to perform an optical coherence tomography (OCT) on the user's eye. The scanning module 4990 may comprise a sealing window 4992 that receives the laser light from the fiber collimator 4941 and optically transfers the laser light to a free space two-dimensional scanner 4993, which provides the scan pattern of the laser light. The two-dimensional scanner may comprise a scanner as described herein, such as a two-axis galvanometer, or a two axis electro-static scanner, for example. When present, the sealing window 4992 may be used to keep the internal components of the binocular OCT device 4900 free of dirt and/or moisture. The laser light is then optically transferred to relay optics 4994 such that the scanned laser light can be input to the user's eye via the free space RT optics 4910-1. In this regard, the scanned laser light may be transferred to a hot mirror 4913 such that infrared light may be reflected back towards the hot mirror, the scanning mirror and focused into an optical fiber tip coupled to the collimation lens. The hot mirror 4913 generally transmits visible light and reflects infrared light, and may comprise a dichroic short pass mirror, for example.

The scanner and associated optics can be configured to scan any suitably sized region of the retina. For example, the scanner can be configured to scan the retina over an area comprising a maximum distance across within a range from about 1.5 to 3 mm, for example. The scanning region of the retina may comprise an area larger than maps of retinal thickness in order to account for slight errors in alignment, e.g. up to 0.5 mm in the lateral positioning of the eye in relation to the OCT system, for example in order to compensate for alignment errors, e.g. by aligning the map based on the measured position of the eye. The size of the OCT measurement beam on the retina can be within a range from about 25 microns to about 75 microns. In some embodiments, the mirror is scanned with a continuous trajectory with a scan rate on the retina within a range from about 50 mm per second to about 200 mm per second. The displacement of the beam during an A-scan can be within a range from about 2 to 10 microns, for example. The beams for each of a plurality of A-scans can overlap. In embodiments where the one or more VCSELs comprises a plurality of VCSELs, the plurality of VCSELs can be sequentially scanned for each A-scan, such that the measurement beams from each of the plurality of VCSELs overlaps on the retina with a prior scan. For example, each of the sequentially generated beams from each of the plurality of VCSELs from a first A-scan can overlap with each of the sequentially generated beams from each of the plurality of VCSELs from a second A-scan along the trajectory.

As described herein, the binocular OCT device 4900 may comprise an IPD adjustment via the components 4905-1 and/or 4905-2. These components may be communicatively coupled to a manual translation stage IP adjustment module 4982 that perform the actuation of the free space optics modules 4910-1 and 4910-2, so as to change a separation distance between the free space optics modules and adjust the IPD.

The main electronic board 4970 may comprise a variety of components. For example, a photodetector 4972 may be used to receive laser light directed from the VCSELs 4952 through the fiber connector 4960 as well interfering light reflected from the user's eye. The fiber connector 4960 may comprise a module 4961 that couples a plurality of optical fibers, for example four optical fibers, to a plurality of detectors, for example five detectors. The fiber connector 4960 may also comprise an interferometer clock box 4962 (e.g. an etalon) that may be used in phase wrapping light reflected back from the user's eyes, as shown and described herein. Once received by the photodetectors 4972, the photodetectors 4972 may convert the light into electronic signals to be processed on the main electronic board 4970 and/or another processing device. The plurality of photo detectors may comprise two detectors of a balanced detector pair coupled to the fiber Mach-Zender interferometer, a clock box detector, and a pair of power measurement detectors, for example.

The main electronic board 4970 may comprise a communication power module 4973 (e.g., a Universal Serial Bus, or "USB") that can communicatively couple the binocular OCT device 4900 to another processing system, provide power to the binocular OCT device 4900, and/or charge a battery of the binoculars OCT device 4900. Of course, the binocular OCT device 4900 may comprise other modules that may be used to communicate information from the binocular OCT device 4900 to another device, including for example, Wi-Fi, Bluetooth, ethernet, FireWire, etc.

The main electronic board 4970 may also comprise VCSEL driving electronics 4971 which direct how and when the VCSELs 4952 are to be fired towards the user's eyes. Other components on the main electronic board 4970 comprise an analog block 4974 and a digital block 4975 which may be used to process and/or generate analog and digital signals, respectively, being transmitted to the binocular OCT device 4900 (e.g., from an external processing system), being received from various components within the binocular OCT device 4900, and/or being received from various components within the binocular OCT device 4900. For example, the peripheral feedback button 4932 may generate an analog signal that is processed by the analog block 4974 and/or digital clock 4975, which may in turn generate a control signal that is used to stimulate the motorized stage module 4942 via the peripheral board 4943. Alternatively or additionally, the analog block 4974 may process analog signals from the photodetectors 4972 such that they may be converted to digital signals by the digital block 4975 for subsequent digital signal processing (e.g., FFTs, phase wrapping analysis, etc.).

Figure 6:
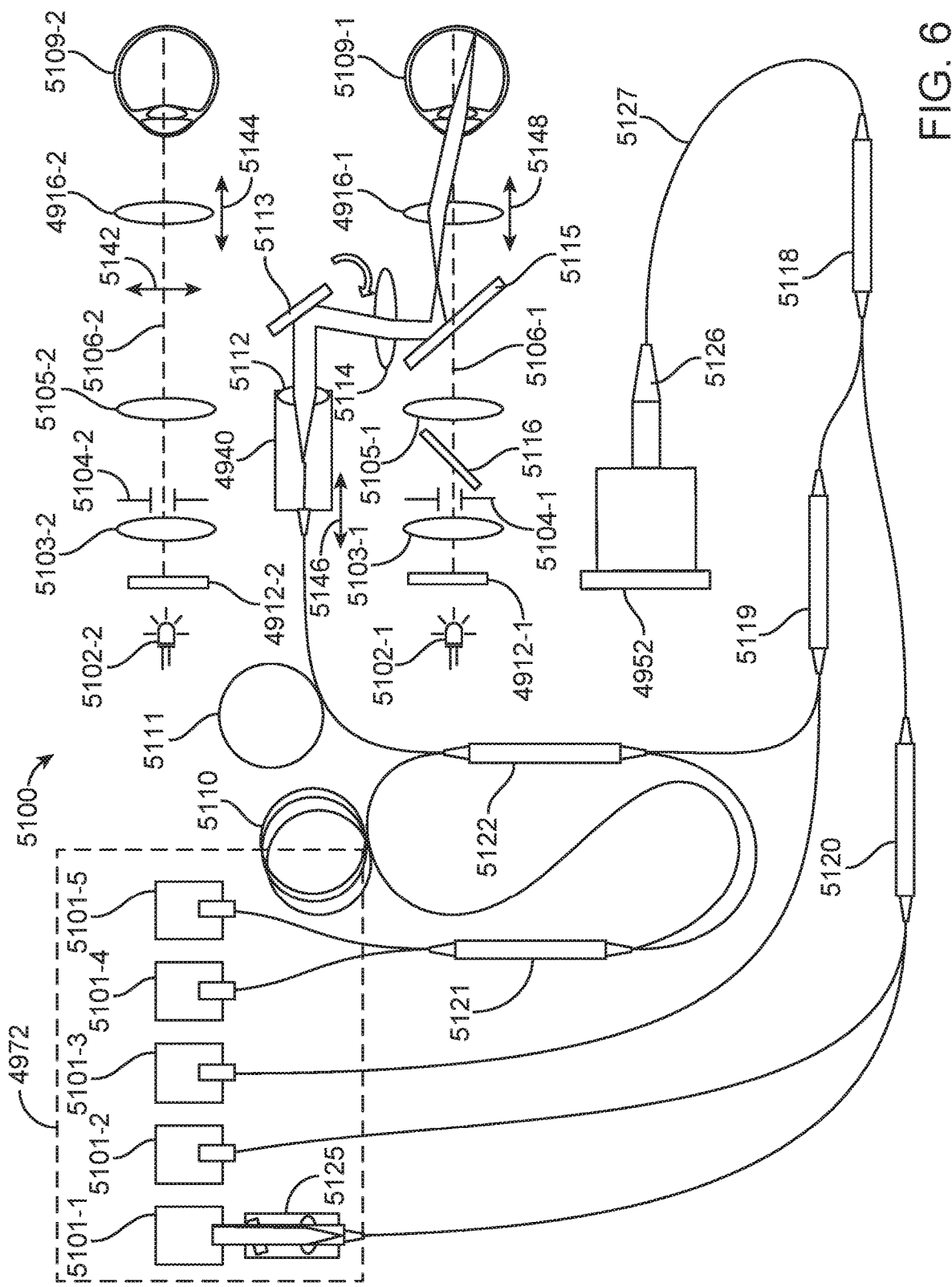
FIG. 6 shows a schematic of an optical configuration that may be implemented with the OCT binocular, in accordance with some embodiments.

FIG. 6 shows a schematic of an optical configuration 5100 that may be implemented with the OCT binocular 4900, in accordance with some embodiments. The optical configuration 5100 comprises one or more VCSELs 4952 that are fiber coupled via an optical coupler 5126. As discussed above, the one or more VCSELs 4952 may be swept over a range of wavelengths when fired. For embodiments with a plurality of VCSELs 4952, the wavelengths may partially overlap a wavelength sweep range of another VCSEL 4952 in the plurality so as to increase in overall sweep range of the VCSELs 4952. In some instances, this overall sweep range is centered around approximately 850 nm. The laser light from the one or more VCSELs 4952 is propagated through the fiber coupler 5126 to a fiber optic line 5127, where another optical coupler 5118 splits a portion of the optical energy from the one or more VCSELs 4952 along two different paths.

In the first path, approximately 95% of the optical energy is optically transferred to another optical coupler 5119 with approximately 5% of the optical energy being optically transferred to an optical coupler 5120. In the second path, the optical energy is split yet again via an optical coupler 5120. In this regard, approximately 75% of the optical energy from the optical coupler 5120 is transferred to a phase correction detector 5101-1 through an interferometer such as a Fabry Perot interferometer comprising an etalon. The etalon and detector may comprise components of an optical clock 5125. The optical clock 5125 may comprise a single etalon, for example. The etalon may comprise substantially parallel flat surfaces and be tilted with respect to a propagation direction of the laser beam. The surfaces may comprise coated or uncoated surfaces. The material may comprise any suitable light transmissive material with a suitable thickness. For example, the etalon may comprise a thickness within a range from about 0.25 mm to about 5 mm, for example within a range from about 0.5 mm to about 4 mm. The reflectance of the etalon surfaces can be within a range from about 3% to about 10%. The etalon can be tilted with respect to the laser beam propagation direction, for example tilted at an angle within a range from about 5 degrees to about 12 degrees. The finesse of the etalon can be within a range from about 0.5 to about 2.0, for example, for example within a range from about 0.5 to 1.0. The etalon may comprise any suitable material such as an optical glass. The thickness, index of refraction, reflectance and tilt angle of the etalon can be configured to provide a substantially sinusoidal optical signal at the clock box detector. The finesse within the range from about 0.5 to 2.0 can provide substantially sinusoidal detector signals that are well suited for phase compensation as described herein, although embodiments with higher finesse values can be effectively utilized.

In some embodiments, the clockbox may comprise a plurality of etalons. The approach can be helpful in embodiments wherein the one or more VCSELs comprises a plurality of VCSELs, and the plurality of etalons provides additional phase and clock signal information. For example, the clockbox may comprise a first etalon and a second etalon arranged so that light is transmitted sequentially through the first etalon and then the second etalon, e.g. a series configuration, which can provide frequency mixing of the clock box signals and decrease the number of detectors and associated circuitry used to measure phase of the swept source. Alternatively, the plurality of etalons can be arranged in a parallel configuration with a plurality of etalons coupled to a plurality of detectors.

The phase correction detector 5101-1 may use the light signals from the optical clock 5125 to correct the phase of light reflected from a user's eyes 5109-1 by matching the phases of the one or VCSELs 4952 via phase wrapping of the light from the one or more VCSELs 4952 as described herein. The remaining 25% of the optical energy from the optical coupler 5120 may be optically transferred to a detector 5101-2 for optical safety. For instance, the detector 5101-2 may be used to determine how much optical energy is being transferred to the user's eye 5109-1 or 5109-2, depending on the orientation of the device. If the binocular OCT device 4900 determines that the detector 5101-2 is receiving too much optical energy that may damage the user's eyes, then the binocular OCT device 4900 may operate as a "kill switch" that shuts down the VCSELs 4952. Alternatively or additionally, the binocular OCT device 4900 may monitor the detector 5101-2 to increase or decrease the optical energy from the VCSELs 4952 as deemed necessary for laser safety and/or signal processing. The OCT device may comprise a second safety detector 5101-3 to provide a redundant measurement for improved eye safety.

The optical energy transferred to the optical coupler 5119 (e.g., approximately 95% of the optical energy from the one or more VCSELs 4952) is also split along two paths with approximately 99% of the remaining optical energy being optically transferred along a fiber to an optical coupling element 5122 and with approximately 1% of the remaining optical energy also being optically transferred to a detector 5101-3 for laser safety of the binocular OCT device 4900. The portion of the optical energy transferred to the to the optical coupler 5122 may be split by the optical coupler 5122 between two optical path loops 5110 and 5111 of the Mach-Zender interferometer, approximately 50% each, for example. The optical path loop 5110 may comprise a reference arm of the interferometer provide a reference optical signal for the retinal thickness measurement of the user's eye 5109-1 (e.g., the measurement signal reflected from the user's retina through the optical path loop 5111).

The portion of the optical energy transferred through the optical loop 5111 is transferred to the user's left eye 5109-1 along the measurement arm of the Mach-Zender interferometer. For instance, the optical energy being transferred to the user's eye 5109-1 may pass through the OPD correction module 4940 to perform any optical path distance corrections appropriate interferometer of the binocular OCT device 4900. This light may then be scanned across the user's eye 5109-1 via a scanning mirror 5113 of the scanner module 4990 to measure the retinal thickness of the user's eye 5109-1 while the user's eye 5109-1 is fixated on a fixation target 4912-1 (e.g., along a fixation path 5106-1).

The fixation target 4912-1 can be back illuminated with LED 5102-1, and light may be propagated along the optical path 5106-1 through optical elements 5103-1 and 5105-1 and the dichroic mirror 5115, comprising a hot mirror. In some instances, the target of fixation may also include an illumination stop 5104 so as to provide relief to the user's eye 5109-1 while fixating on the target.

The light impinging the user's retina of the eye 5109-1 may be reflected back along the path established by the OPD correction module 4940, the scanning mirror 5113, the focusing element 5114, the dichroic mirror 5115, and the optical element 4916-1, through the optical loop 5111, and back to the optical coupler 5122. In this instance, the optical coupler 5122 may optically transfer the reflected optical energy to an optical coupler 5121 which may couple the reflected optical energy with the optical energy that was split into the optical loop 5110. The optical coupler 5121 may then optically transfer that optical energy to the balanced detector's 5101-4 and 5101-5 such that a retinal thickness measurement can be performed. In doing so, the optical coupler 5121 may split that optical energy to approximately 50% to each of the detectors 5101-1 and 5101-4, such that the interference signals arrive out of phase on the balanced detectors.

The light may be focused through a plurality of optical elements 5112 and 5114, being directed to the user's eye 5109-1 via a dichroic mirror 5115 and focused on the user's retina via the optical element 4916-1. The light from the scanning mirror 5113 and the light reflected from the user's eye 5109 are both shown as reflecting off the dichroic mirror 5115, which may comprise hot mirror 4913 configured to generally reflect infrared light and transmit visible light.

As can be seen in this example, the user's right eye 5109-2 does not receive any optical energy from the one or more VCSELs 4952 with the orientation shown. Rather, the user's right eye 5109-2 is used for binocular fixation with the target 4912-2, which can be back illuminated with another LED 5102-2. The target 4912-2 can be of similar size and shape to target 4912-1 and be presented to the eye with similar optics, so as to provide binuclear fixation. In this regard, the user's right eye 5109-2 may also fixate on the target 4912-2 along an optical path 5106-2 through the optical elements 4916-2, 5105-2, 5103-2, and the illumination stop 5104, which comprises similar optical power, separation distances and dimensions to the optics along optical path 5106-1.

The binocular OCT system 4900 can be configured to move optical components to a customized configuration for the user being measured. Lens 4916-1 can be adjusted along optical path 5106-1 in accordance with the refraction, e.g. eyeglass prescription of the eye being measured. Lens 4916-1 can be moved under computer, user or other control to adjust lens 4916-1 to bring the fixation target 4912-1 into focus and to focus the measurement beam of the OCT interferometer on the user's retina. For example, the lens can be translated as shown with arrow 5144. Lens 4916-2 can be moved under computer, user or other control to adjust lens 4916-1 to bring the fixation target 4912-2 into focus on the user's retina. For example, the lens can be translated as shown with arrow 5148. The OPD correction module 4950 can be translated axially toward and away from mirror 5113 as shown with arrows. The OPD correction module 5146 can be moved under computer control to appropriately position the optical path difference between the measurement arm and the reference arm for the user's eye being measured. The interpupillary distance can be adjusted by translating the optical path 5106-2 toward and away from optical path 5106-1.

The free space optics module 4910-2 may comprise one or more components along optical path 5106-2, such as the LED 5102-2, the fixation target 4912-2, lens 5103-2, aperture 5104-2, lens 5105-2, or lens 4916-2. The free space optics module 4910-2 can be translated laterally toward and away from the optical components located along optical path 5106-1 to adjust the inter pupillary distance as shown with arrow 5142. The free space retinal thickness optics module 4910-1 may comprise one or more components located along optical path 5106-1, such as the LED 5102-1, the fixation target 4912-1, the aperture 5104-1, the mirror 5116, the lens 5105-1, the mirror 5115, or lens 4916-1. The OPD correction module 5146 may comprise the optical fiber of the measurement arm of the interferometer, and lens 5112 to substantially collimate light from the optical fiber and to focus light from the retina into the optical fiber.

Figure 7:
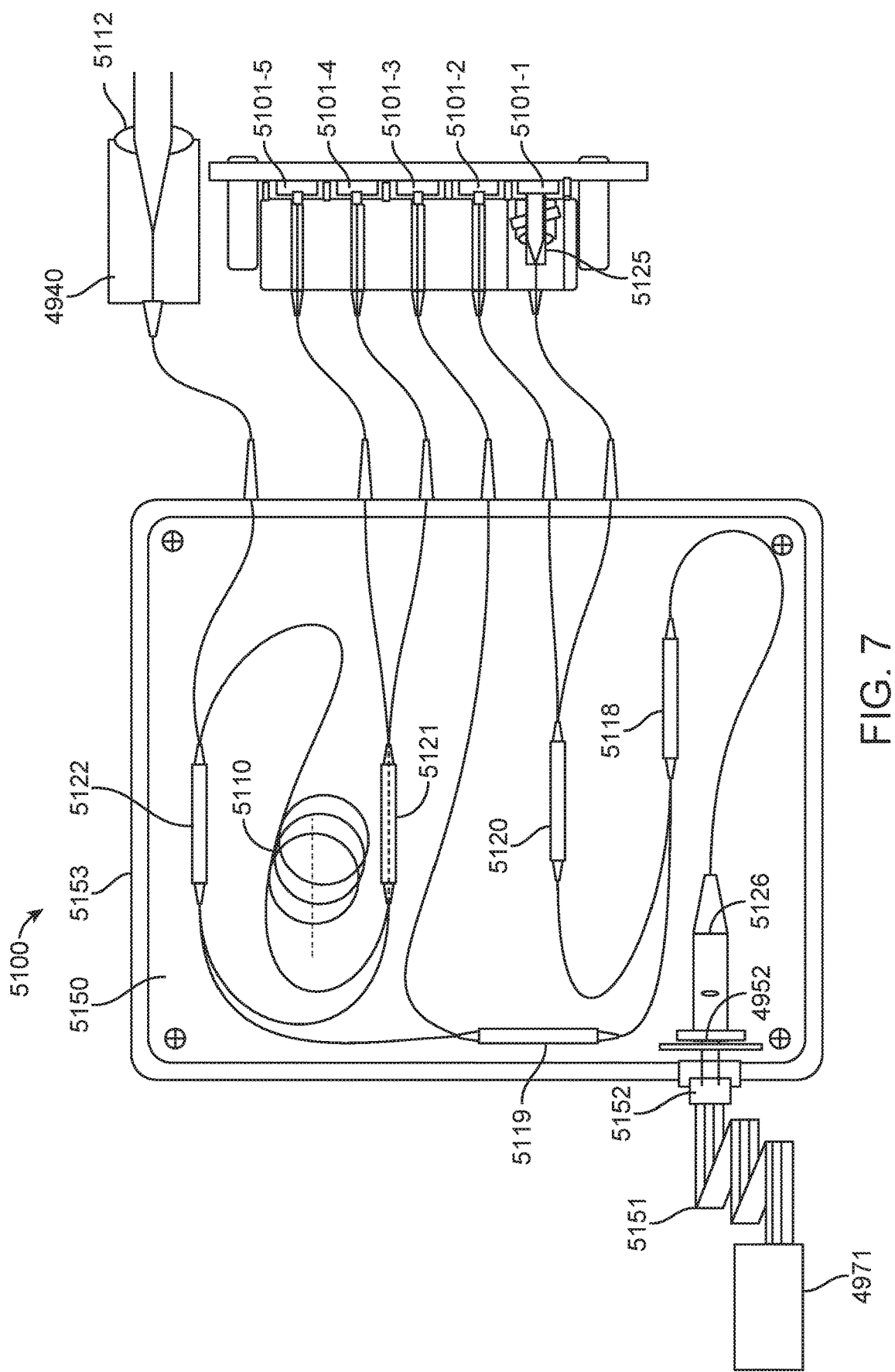
FIG. 7 shows a block diagram of the optical configuration configured on an optical layout board, in accordance with some embodiments.

FIG. 7 shows a block diagram of the optical configuration 5100 configured on an optical layout board 5150, in accordance with some embodiments. For example, the binocular OCT device 4900 may be configured with a plurality of layers extending approximately along planes, each of which layers may be configured to perform a particular function. In this instance, the optical layout board 5150 provides a support for the optical configuration 5100, which can be used to decrease vibrations of the optical components. The optical board 5150 may comprise a plurality of components enclosed within a housing of a fiber optics module as described herein. The plurality of components enclosed within the housing 5153 and supported on the board, may comprise one or more of coupler 5118, coupler 5119, coupler 5120, coupler 5121, coupler 5122, reference arm comprising optical fiber 5110, and any combination thereof. The one or more VCSELs 4952 may be enclosed within the housing. The plurality of optical fibers extending from coupler 5120 can extend through the housing to the appropriate detector, for example to couple to clock box detector 5101-1 and safety detector 5101-2. The optical fiber extending from coupler 5119 can be coupled to a second safety detector 5101-3 and extend though housing 5153. A second optical fiber extending from coupler 5119 can be coupled to the interferometer to measure the sample with optical coupler 5122. The optical fiber portion of the sample measurement arm extending from coupler 5122 and extend to through the housing 5153 to the optical path difference correction module 4940, for example.

The printed circuit board may provide a support layer extending along an electronics plane in which some processing devices (e.g., the main electronic board 4970 including the driving electronics 4971 of FIG. 50) could couple to the optical layout board 5150 through a cable 5151 that connects to a connector 5152 configured with the optical layout board 5150 in order to drive one or more VCSELs 4952.

Figure 8:
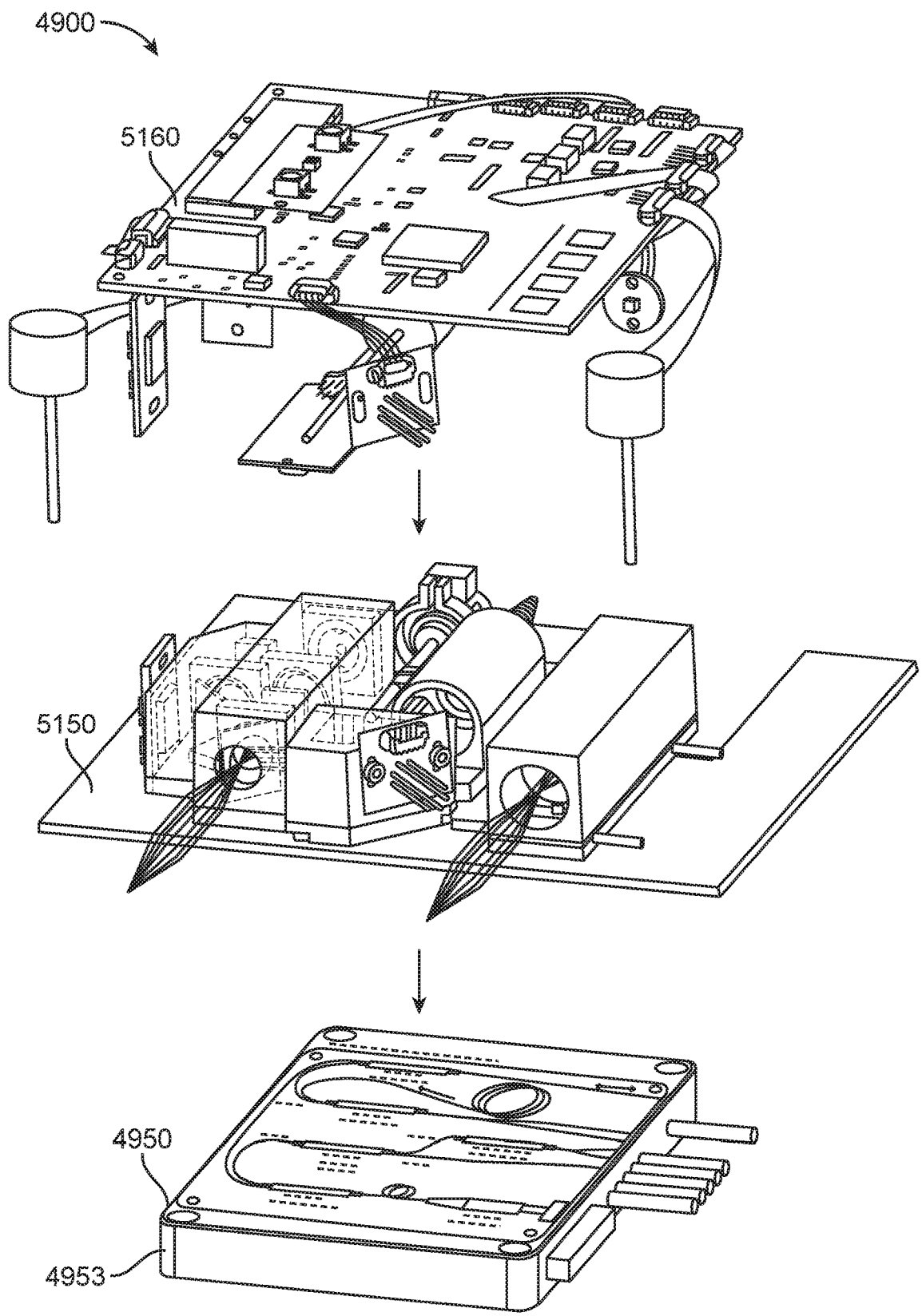
FIG. 8 shows a perspective view of a modular binocular OCT, in accordance with some embodiments.

FIG. 8 shows a perspective view of a modular embodiment of the binocular OCT 4900, in accordance with some embodiments. For instance, the main electronic board 4970 of the binocular OCT 4900 may be implemented as a printed circuit board (PCB) 5160 that is mounted to a housing 4903 enclosing optical components on the optical layout board 5150. The PCB 5160 may provide the power and electronics to control the optical configuration 5100 of the optical layout board 5150. The PCB 5160 may also include or be communicatively coupled to peripheral boards 4932-1, 4932-2, 4943, 4914-1, and 4914-2. The binocular OCT device 4900 may also comprise free space optics modules that are mounted on the optical layout board 5150 and communicatively couple to the main electronic board 4970. The free space optics modules mounted on the optics board may comprise one or more of module 4910-1, module 4910-2, or OPD correction module 4940 as described herein. The free space module 4910-2 can be configured to move in relation to optical layout board 5150 to adjust the inter pupillary distance. The OPD correction module can be configured to move relative to optical layout board 5150.

The interferometer module 4950 may comprise the couplers of the optical fibers as descried herein and the one or more VCSELs 4952. The main electronic board 4970 or one of the peripheral boards may comprise the electronics that drive the VCSELs 4952. The one or more VCSELs 4952 being optically coupled to the optical fibers on the optical layout board 5150, propagate laser light to the optical fibers on the optical layout board 5150. The laser light reflected from the user's eye can be propagated to the PCB 5160 where the photodetector 4972 detects the reflected laser light and converts the light to an electronic analog signal for processing by the analog block 4974.

In some embodiments, the optical layout board 5150 provides damping to the binocular OCT 4900. For instance, if the binocular OCT 4900 were to be dropped, a damping mechanism configured with the optical layout board 5150 may compensate for any oscillatory effects on impact of the binocular OCT 4900 and protect the components thereof (e.g., the optical layout board 5150, the PCB 5160, interferometer module 4950, and the components of each). The mounting plate 5150 may comprise similar damping mechanisms.

Figure 9:
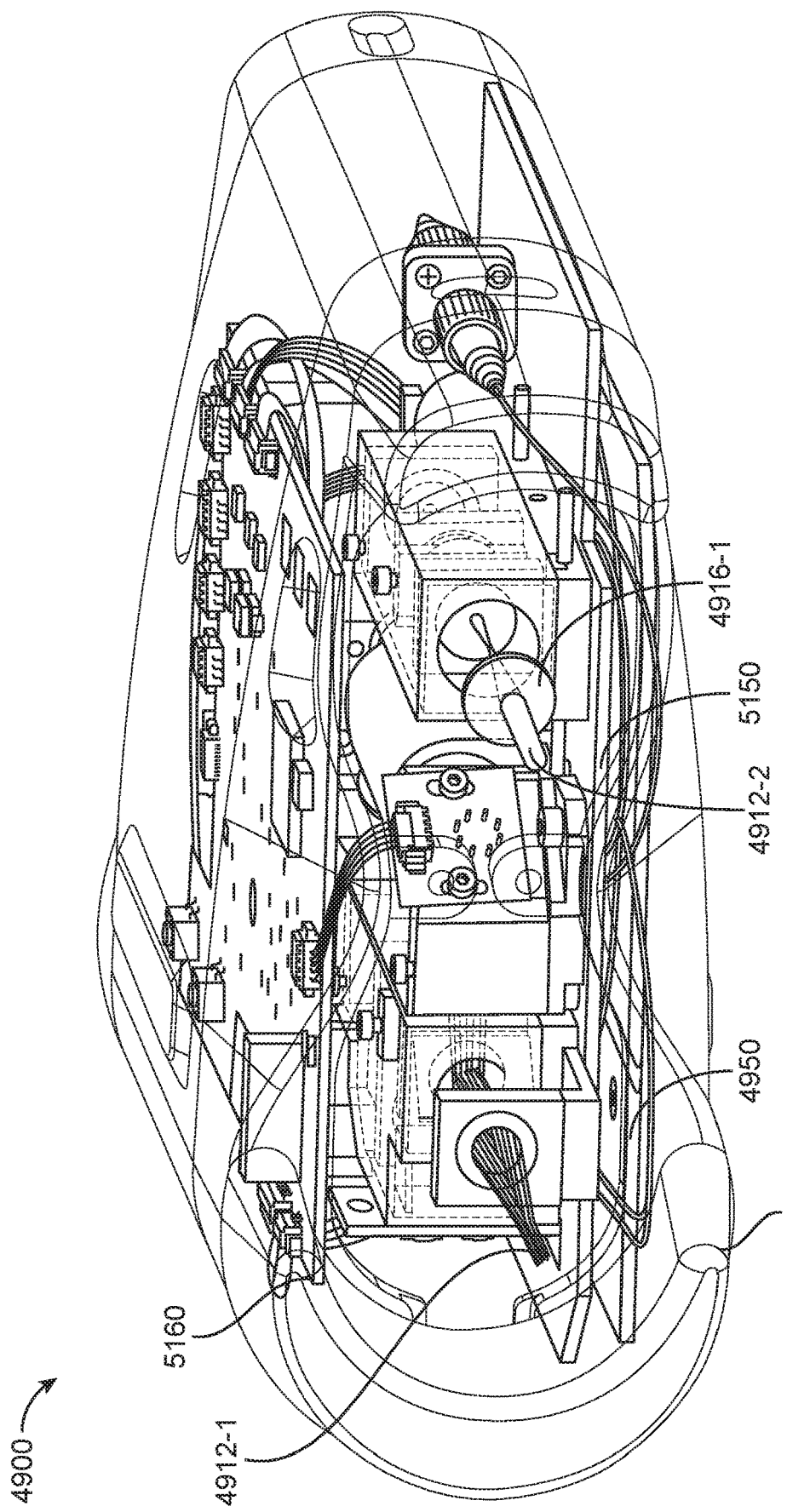
FIG. 9 shows a perspective/cut-away view of the binocular OCT device, in accordance with some embodiments.

FIG. 9 shows a perspective/cut-away view of the binocular OCT 4900, in accordance with some embodiments. In this view, the optical layout board 5150, the PCB 5160, and the interferometer module 4950 are mechanically coupled together in a compact form configured within the housing 4903 of the binocular OCT 4900. As can be seen in this view, the fixation targets 4912-1 and 4912-2 (e.g., LED light) are visible to the user through the lenses 4916-1 and 4916-2, respectively, when the user places the binocular OCT 4900 proximate to the user's eyes. Laser light from the VCSELs 4952 propagate along a portion of the same optical path as the fixation target 4912-1. Thus, when the user gazes on the fixation targets 4912-1 and 4912-2, the laser light from the one or more VCSELs 4952 are operable to propagate through the user's eye and reflect back to the optical layout board 5150 for subsequent processing to determine the user's retinal thickness.

Figure 10:
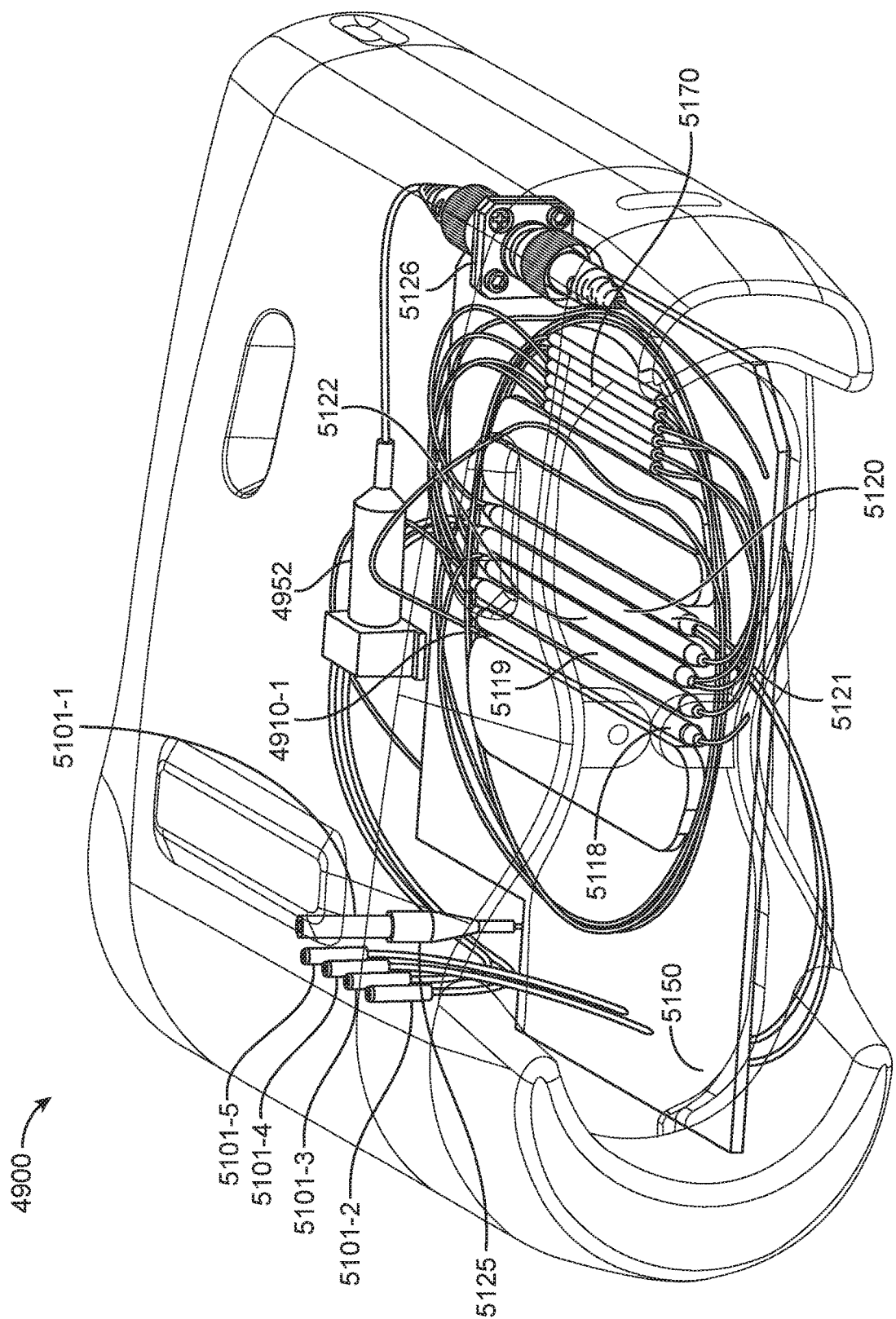
FIG. 10 shows another perspective/cut-away view of the binocular OCT device, in accordance with some embodiments.

FIG. 10 shows another perspective/cut-away view of the binocular OCT 4900, in accordance with some embodiments. In this view, only the optical layout board 5150 is illustrated to show the configuration of the VCSELs 4952, the fiber coupler 5126, the detector's 5105-1-5105-5, the Fabry Perot optical clock 5125, and the optical couplers 5118-5122. The optical layout board 5150 may also comprise splicers 5170.

Figure 11:
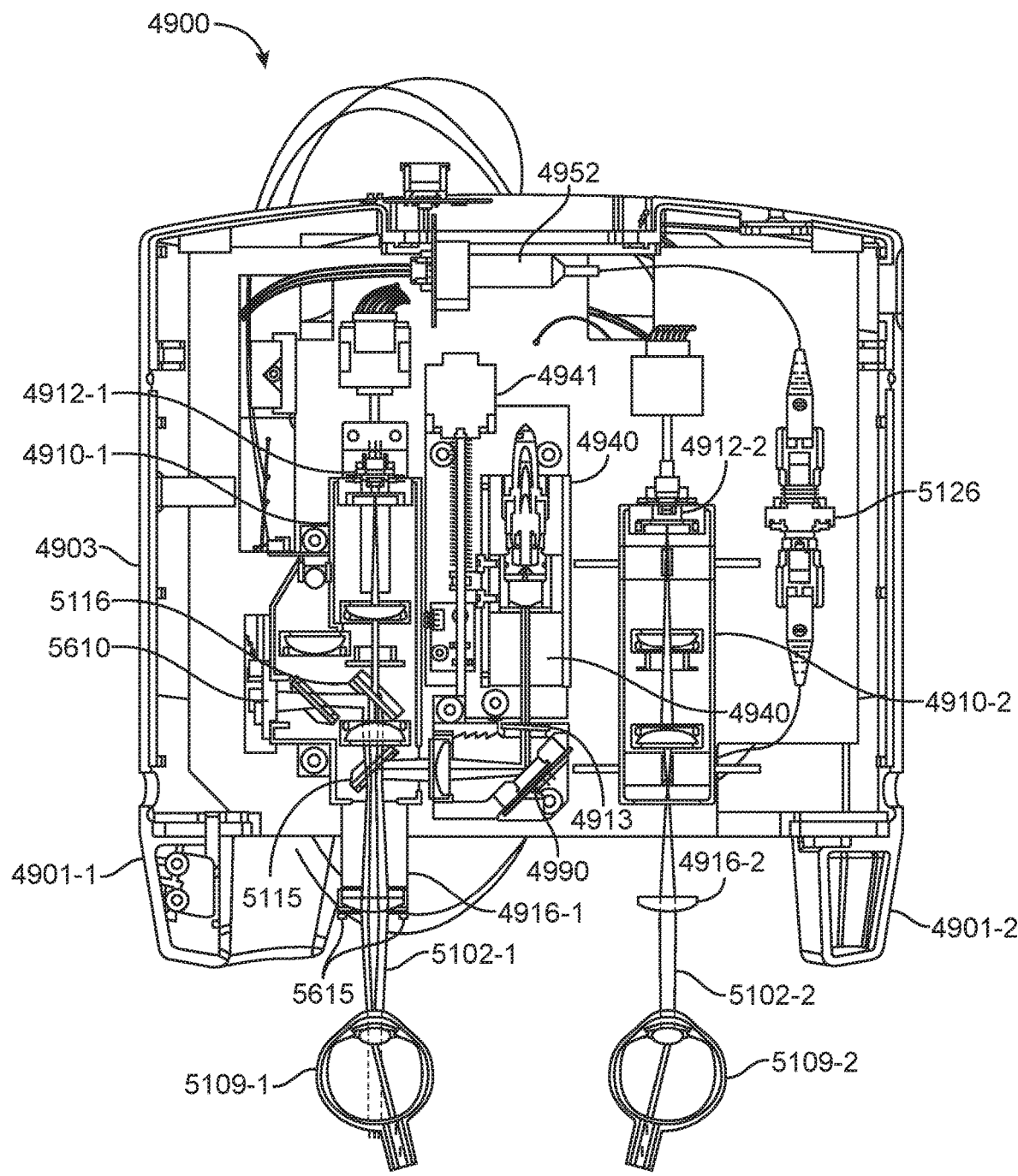
FIG. 11 shows an overhead/cut-away view of the binocular OCT device comprising an eye position sensor, in accordance with some embodiments.
Figure 12:
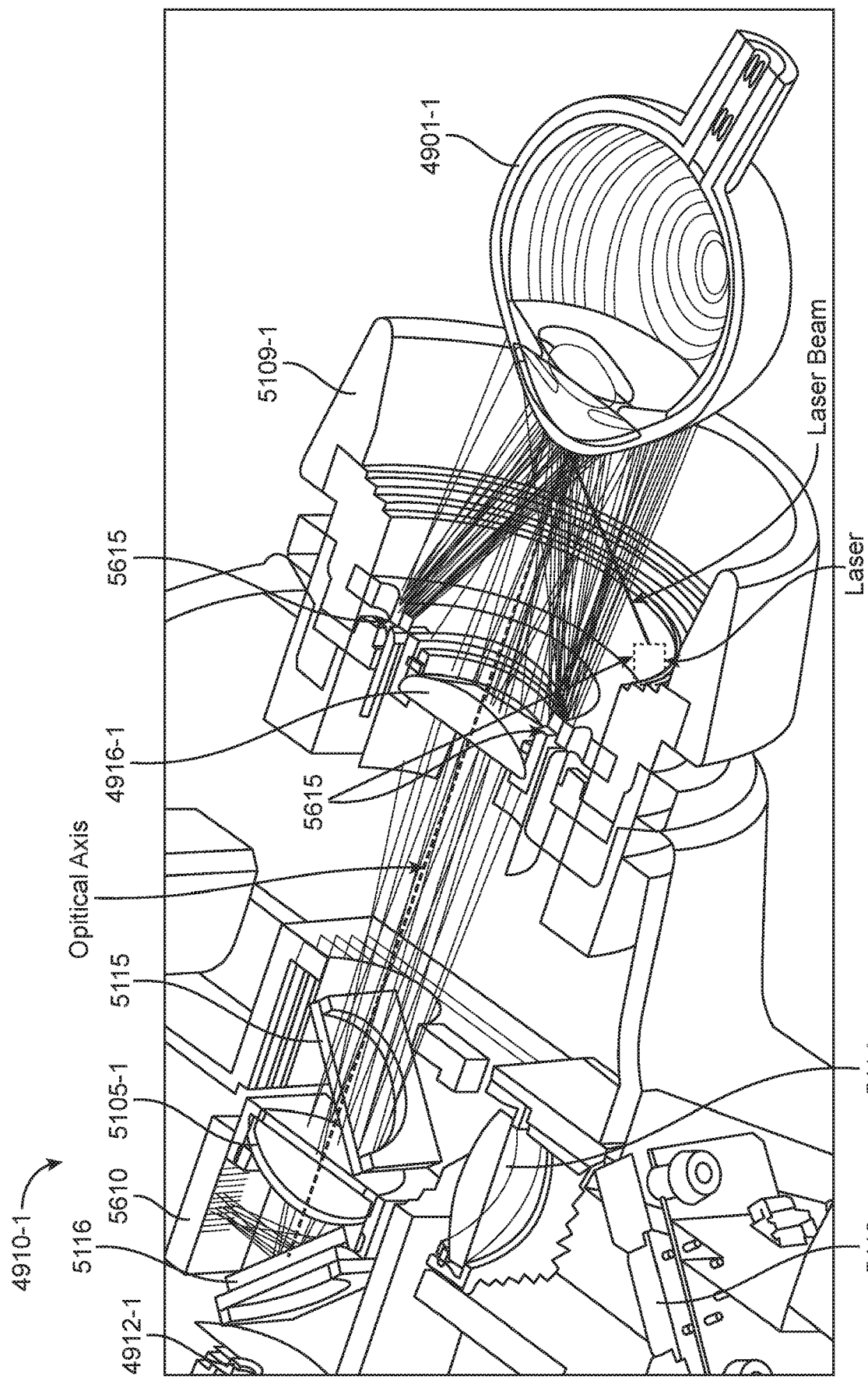
FIG. 12 shows a perspective/cut-away view of the light sources used to generate a Purkinje image of the eye and the positions sensor, in accordance with some embodiments.

FIGS. 11 and 12 show the binocular OCT system 4900 comprising an eye position sensor, in accordance with some embodiments. FIG. 56 shows an overhead/cut-away view of the binocular OCT 4900 comprising an eye position sensor 5610, in accordance with some embodiments. FIG. 12 shows a perspective/cut-away view of the plurality of light sources 5615 used to generate a Purkinje image of the eye and the positions sensor. The eye position sensor 5610 may comprise one or more of an array sensor, a linear array sensor, one dimensional array sensor, a two-dimensional array sensor, a complementary metal oxide (CMOS) two-dimensional array sensor array sensor, a quadrant detector or a position sensitive detector. The eye position sensor 5610 can be combined with a lens to form an image of the eye on the sensor, such as a Purkinje image from a reflection of light from the cornea of the eye. The eye position sensor can be incorporated into any of the embodiments disclosed herein, such as the binocular OCT system described with reference to FIGS. 4 to 10.

In the view shown, the optical configuration 5100 is mounted on the optical layout board 5150 above the fiber-optic couplings (e.g., the fiber loops 5110 and 5111 of FIG. 6) and the optical couplers 5118-5122, and other fiber components as described herein. Thus, the one or more free space optical components as described herein may be optically coupled to the fiber components thereunder.

As shown, the free space optics modules 4910-1 and 4910-2 are generally aligned with the user's eyes 5109-1 and 5109-2, respectively. The distance between the free space optics modules 4910-1 and 4910-2 may be adjusted according to the user's IPD. In some embodiments, this adjustment is maintained for the user while the binocular OCT 4900 is in the user's possession. For example, the user may be a patient using the binocular OCT 4900 for home use over a certain period of time. So as to ensure that a correct retinal thickness is measured while in the user's possession, the binocular OCT 4900 may prevent the user from adjusting the IPD. Similarly, the binocular OCT 4900 may also prevent the user from adjusting the OPD via the OPD correction module 4940.

As can be seen in this view, the fixation targets 4912-1 and 4912-2 (e.g., LED light targets) pass through various optical elements of their respective free space optics modules 4910-1 and 4910-2. The OPD correction module 4940 receives the laser light from the one or more VCSELs 4952 and directs light toward the scanning mirror 4990 as described herein. Light from the scanning mirror 4990 passes through a lens and is reflected by a dichroic mirror 5115 to the user's eye 5109-1 through the lens 4916-1.

As shown FIG. 12, the plurality of light sources 5615 comprising a first light source and a second light source is used to generate a Purkinje image. Additional light sources may be used to generate the Purkinje image, for example four light sources can be located along approximately orthogonal axes. The plurality of light sources can be configured in many ways, and may comprise one or more of LEDs, waveguides, apertures or optical fibers, and can be arranged in a pattern such as a triangle, rectangle, Placido disk, or the like, so as to form a virtual image of the pattern when reflected from the cornea of the eye. The light from the plurality of light sources is directed toward the eye and reflected from the tear film on the anterior surface of the cornea toward lens 4916-1. The light rays reflected from the cornea are transmitted through beam splitter 5115 and the lens 5105-1 to form an image of the eye on eye position sensor 5610. A mirror 5116 can be located along optical path 5106-1 to reflect light from the plurality of light sources toward the eye position sensor 5610, and the mirror 5116 can be configured to transmit visible light such as green light from the fixation target.

The plurality of light sources 5615 of the eye position sensor 5610 can be configured in many ways. In some embodiments, the plurality of light sources comprises a laser that creates a reflection such as a Purkinje reflection. The laser can be positioned to the side of the optical axis, and the laser beam oriented to cross the optical axis at an angle. The cavity of the laser can be inclined with respect to the optical axis to incline the laser beam, or lenses, prisms or mirrors used to incline the laser beam with respect to the optical axis, and combinations thereof. Because the laser is angled with respect to the optical axis, it will move across the cornea with variations in Z distance. When the laser reflection from the cornea is centered on a first Purkinje image of a fixation light and a known pixel or group of pixels associated with the center of the optical axis, alignment is achieved. Work in relation to the present disclosure suggests that this approach can provide improved alignment along the optical axis of the OCT device, for example improved alignment along the Z axis. In some embodiments, the laser beam source is configured to cross the optical axis with a greater angle of inclination than the other light sources, so as to increase the displacement of the laser beam more than the other light sources with displacement of the eye along the Z axis.

In some embodiments, the inclined laser beam is combined with the plurality of light sources. In such embodiments, the locations of the Purkinje image reflections can be used to determine the lateral position of the eye with respect to the optical axis, e.g. the X, Y position, and the position of the laser beam in the Purkinje image used to determine the position of the eye along the optical axis, e.g. the Z position of the eye, for example.

Alternatively, the plurality of light sources may comprise a single light source. For example, the inclined laser beam can be used to determine the position of the eye without the other reflections in the Purkinje image, for example when the reflection of the laser beam appears at the correct location of the image.

The optical elements coupled to the position sensor 5610 may comprise one or more components of the optical path of the measurement interferometer and the fixation target. Light from the one or more VCSELs can be reflected off scanning mirror 5113, transmitted through lens 5114, reflected from dichroic mirror 5115 toward the lens 4916-1 and directed toward the eye as described herein. The light from the visual fixation target 4912-1 can be directed through lens 5105-1, transmitted through mirror 5115 and lens 4916-1 toward the eye to provide an image on the patient's retina for visual fixation. A beam splitter 5116, such as a dichroic beam splitter, can be located between lens 5105-1 and fixation target 4912-1 in order to reflect light from the plurality of light sources 5615 toward eye position sensor 5610 and transmit visible light from the fixation target.

While the wavelengths of the light sources can be configured in many ways, in some embodiments, the plurality of light sources to generate the Purkinje image comprises a wavelength within a range from about 700 to 800 nm, the fixation target comprises a wavelength within a range from about 500 to 700 nm, and the OCT measurement beam comprises a plurality of wavelengths within a range from about 800 to 900 nm. The mirror 5115 may comprise a hot mirror or dichroic beam splitter configured to reflect light above 800 nm and transmit light below 800 nm. The beam splitter 5116 may comprise a dichroic mirror configured to reflect light above 700 nm and transmit light below 700 nm. In some embodiments, the light from the one or more VCSELs comprises a wavelength within a range from 800 nm to 900 nm, the plurality of light sources 5615 to generate the Purkinje image comprises a wavelength within a range from about 700 nm to 800 nm, and the visual fixation target comprises a wavelength within a range from about 400 nm to about 700 nm, e.g. within a range from about 500 nm to 700 nm.

Figure 13:
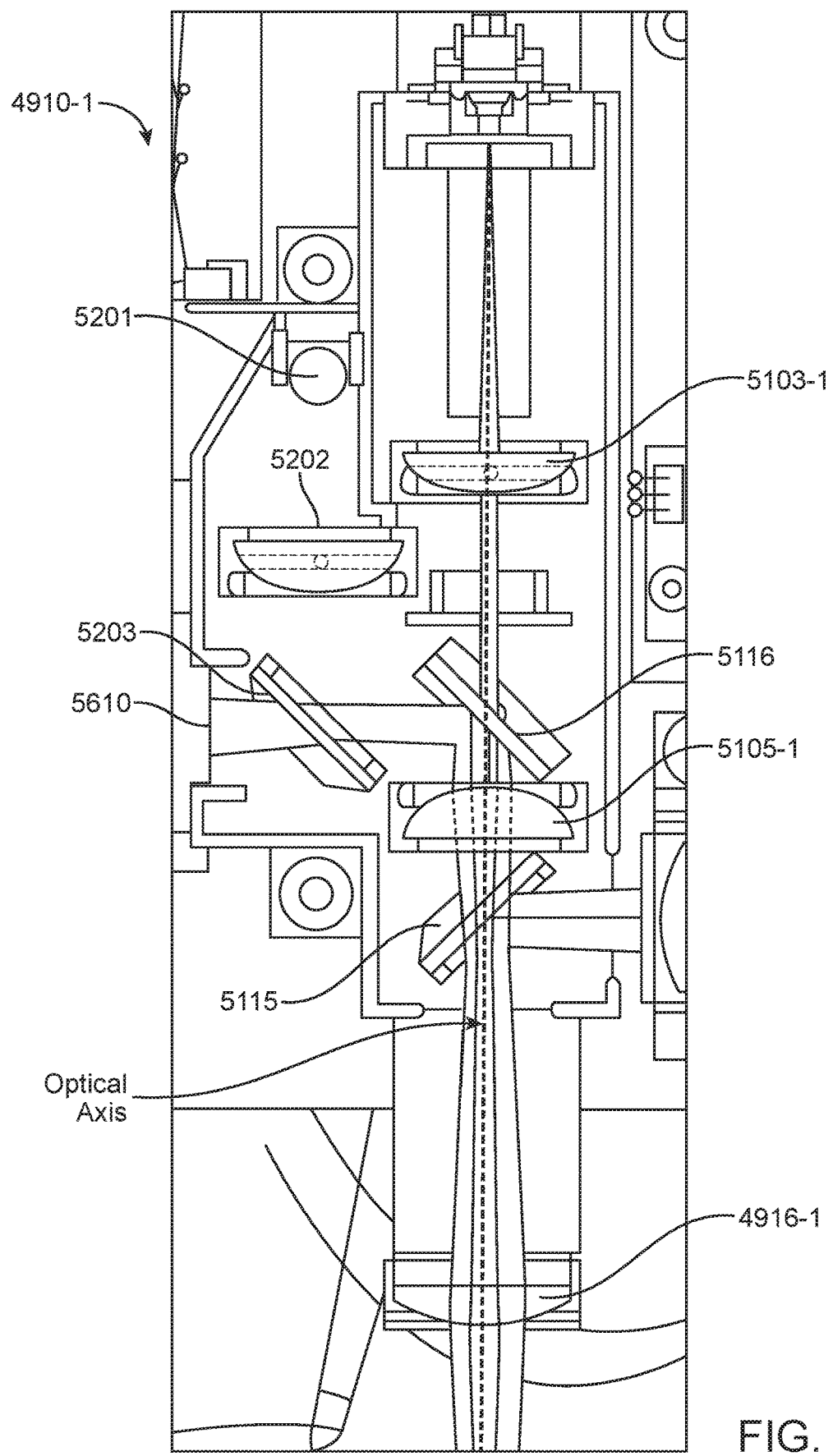
FIG. 13 shows an overhead view of the free space optics comprising a position sensor, in accordance with some embodiments.

FIG. 13 shows an overhead view of the free space optics 4910-1, in accordance with some embodiments. As the laser light enters the free space optics 4910-1, it is reflected off the dichroic mirror 5115 towards the user's eye 5109-1 (not shown) through the optical element 4916-1. The light impinges the user's eye 5109-1 and reflects off the retina thereof back towards the optical element 4916-1. The reflected laser light and is reflected from the dichroic mirror 5115 toward the OPD correction module. The light from the plurality of light sources is reflected from dichroic mirror 5116 toward eye position sensor 5610. The eye position sensor 5610 is operatively coupled to the processor as described herein to positions of the eye as described herein. In alternative embodiments, eye position sensor 5610 can be located at position 5201, and light transmitted through lens 5202 to form the image of the eye on the eye position sensor, such as the Purkinje image as described herein.

The components of binocular OCT device 4900 described with reference to FIGS. 4-13 can be combined to provide a compact OCT device, as will be apparent to one of ordinary skill in the art.

The binocular OCT device 4900 may comprise the handheld OCT device 100 of FIGS. 2, 3A and 3B, and may comprise communication circuitry and be configured to operatively couple to one or more external devices such as mobile patient device 120 as described herein. This connection can be wired, e.g. with a USB connector, or wireless, e.g. with Bluetooth, as described herein. Mobile patient device 120 can be configured to process one or more of the signals from detectors 5101-1 to 5101-5 to generate an A-scan and retinal maps as described herein, for example.

Although FIGS. 4 to 13 make reference to a binocular OCT device 4900, one or more components of binocular OCT device 4900 can be used to construct a mono-ocular OCT device 100 as described herein. For example, free space optics module 4910-2 and the associated translation stage can be removed to adjust interpupillary distance ("IPD") may not be included, and the eyecup configured to cover the eye and block ambient light. In such embodiments, the user can invert the device to measure a second eye as described herein. Alternatively or in combination, an occluder can be provided to cover the non-measured eye with an opaque material to avoid distractions to the non-measured eye. A switch can be coupled to the occluder to provide a signal to the processor to determine which eye is measured, and the data recorded with reference to which eye is being measured as described herein.

Figure 14B:
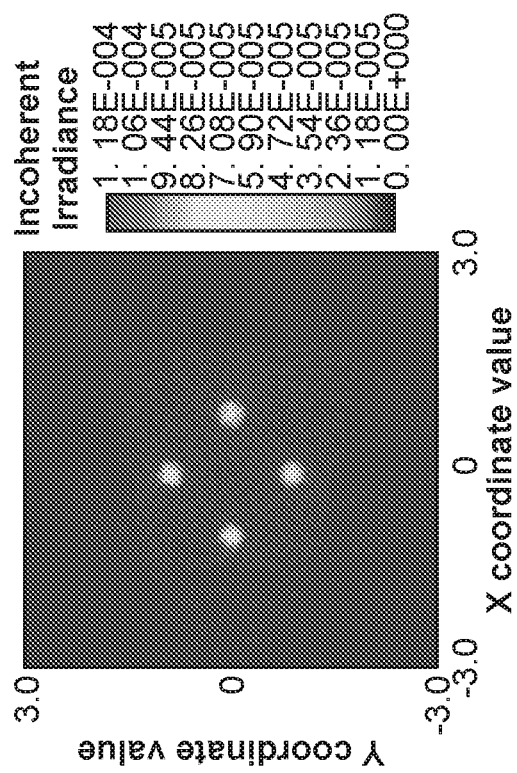
FIG. 14A, FIG. 14B, FIG. 14C, and FIG. 14D show images that can be captured with the eye position sensor to determine a position of the eye in relation to the optical axis, in accordance with some embodiments.
Figure 14A:
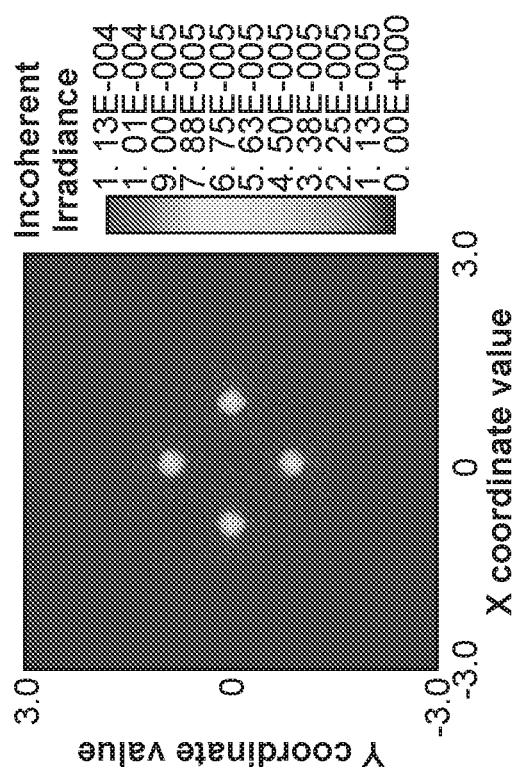
Figure 14C:
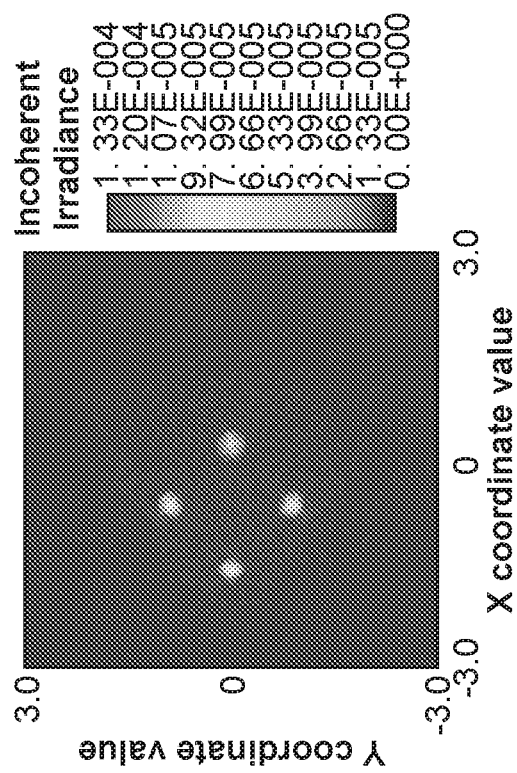
Figure 14D:
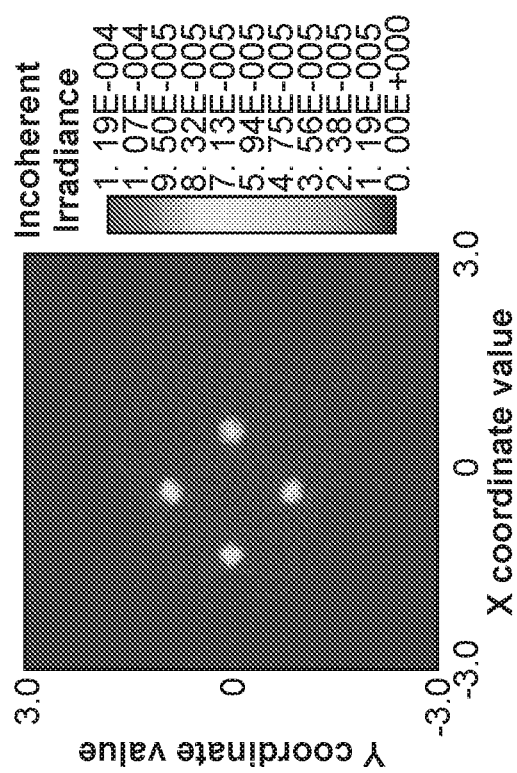

FIGS. 14A-14D show images that can be captured with eye position sensor 5610 to determine a position of the eye in relation to the optical axis 5106-1, in accordance with some embodiments. In each of the images, an image of the plurality of light sources reflected from the cornea is shown. Although an image of the light reflected from the cornea is shown, the eye position sensor may comprise other configurations such as a pupil position imaging configuration, for example. The position of each of four light sources is shown. For instance, FIG. 14A shows an image in which the pupil mismatch is 0 mm and on axis such that the eye is aligned with the free space optics 4910-1 when the user fixates on the fixation target. The position of the eye can be determined in response to the locations of the plurality of light sources imaged onto the eye position detector 5610. In general, an offset of the locations corresponds to translation of the eye in relation to the optical axis of the OCT system. FIGS. 14B, 14C, and 14D illustrate instances where the optical axis of the measurement side of the binocular OCT device 4900 is not perfectly aligned with the eye. More specifically, FIG. 14B shows an alignment error of the cornea of the eye of about 0.5 millimeters along the X-axis. FIG. 14C shows an alignment error of about 1.0 mm along the X-axis, and FIG. 14D shows an alignment error of 1.5 along the X-axis. Similar displacement errors can be calculated along the Y-axis. These displacement errors can be determined with the eye position sensor 5610 along the X-axis and Y-axis, for example the position of the eye with an X, Y coordinate reference in which these axes extend along a plane transverse to the optical axis of the OCT measurement system, such as binocular OCT measurement system.

Figure 15C:
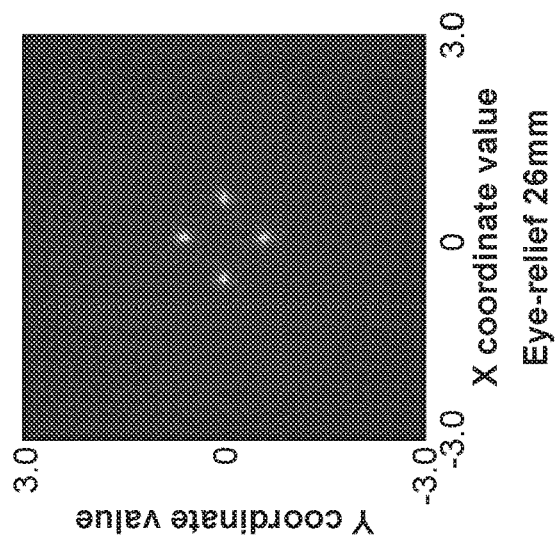
FIG. 15A, FIG. 15B, and FIG. 15C show positions of the plurality of light sources captured with eye position sensor at various eye relief distances between the lens closest to the eye and a user's eye, in accordance with some embodiments.
Figure 15B:
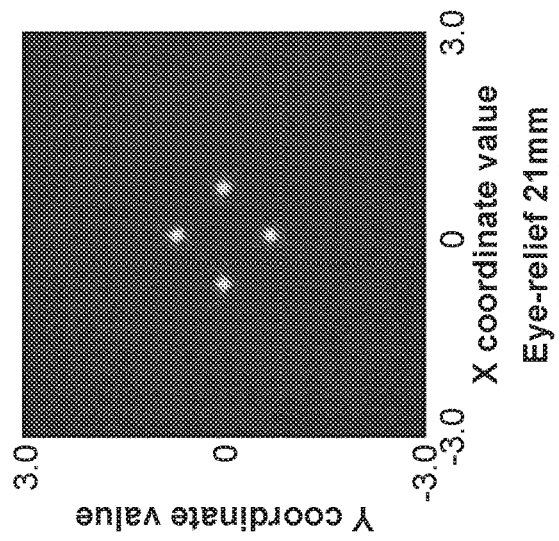
Figure 15A:
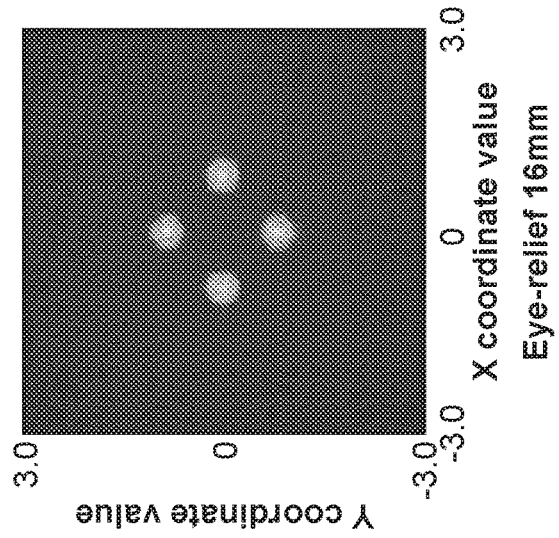

FIGS. 15A-15C show positions of the plurality of light sources captured with eye position sensor 5610 at various eye relief distances between the lens closest to the eye and a user's eye 5109-1, in accordance with some embodiments. In general, the spacing of the image of the plurality of light sources decreases with an increasing relief distance. More specifically, FIG. 15A shows a Purkinje image of light reflected from the plurality of sources at a distance of approximately 16 mm between the user's eye 5109 and the OCT measurement system. FIG. 15B shows an image from position sensor 5610 at a distance of approximately 21 mm. FIG. 15C shows an image of the plurality of light sources from the position sensor at a distance approximately 26 mm between the user's eye 5109 and the OCT measurement system. The spacings between the plurality of light sources decreases with increasing relief distances.

The processor as described herein can be coupled to eye position sensor 5610 to determine the eye relieve distance in X, Y and Z axes. The processor can be coupled to the orientation sensor to determine which eye is measured, and appropriately map the position sensor data to the coordinate reference system of the eye. For example, the X and Y positions of the eye from the sensor 5610 can be inverted when the OCT system comprises an inverted configuration, and the measured positions of the eye appropriately transformed to the user's reference frame. The images captured with the sensor may comprise a combination of X, Y, and Z offsets from an intended position, e.g. 0 alignment error along the X, Y and Z axis.

When the laser reflection from the cornea is centered on a first Purkinje image of a fixation light and a known pixel or group of pixels associated with the center of the optical axis, alignment is achieved, as described herein. In some embodiments, the inclined laser beam is combined with the plurality of light sources. In such embodiments, the locations of the Purkinje image reflections can be used to determine the lateral position of the eye with respect to the optical axis, e.g. the X, Y position, and the position of the laser beam in the Purkinje image used to determine the position of the eye along the optical axis, e.g. the Z position of the eye, for example.

Referring again to FIGS. 15A to 15C, when plurality of light sources comprises the inclined laser beam, laser beam can be imaged onto the detector and appear in the images. When the cornea is positioned at the nominal position, e.g. with an eye relief of 21 mm as shown in FIG. 15B, the reflected laser beam will appear at the center of the four reflections. When the eye is positioned closer to the OCT device, e.g. as shown in FIG. 15A, the reflected laser beam will appear on a first side of the center of the reflected dots from the other light sources. When the eye is positioned farther from the OCT device, e.g. as shown in FIG. 15C, the reflected laser beam will appear on a second side of the center of the reflected dots opposite the first side. The position of the reflected laser beam can be used to position the eye along the optical axis, e.g. the Z-axis, in combination with the positions of the reflected lights from the other light sources.

One or more of the measured eye positions can be used to provide instructions to the user. For example, the user may receive auditory instructions from a mobile device operatively coupled to the OCT measurement system to move the eye left, right, up or down, until the eye is located within a suitable window for OCT retinal thickness measurements as described herein. For example, the system can be configured to acquire OCT measurements once the eye has moved to within about 0.5 mm of the optical axis of the OCT measurement system. One or more of the fixation targets can be configured to provide a visual cue to the user. For example, one or more of the fixation targets can be configured to change color when the measured eye is brought into sufficient alignment. For example, the fixation target can change color from yellow when not sufficiently aligned to green when sufficiently aligned. In some embodiments, both fixation targets can change color when the OCT system comes into sufficient alignment with the eye. Each of the LEDs that illuminate the fixation target as described herein may comprise two or more emission wavelengths, for example yellow and green wavelengths.

Figure 16A:
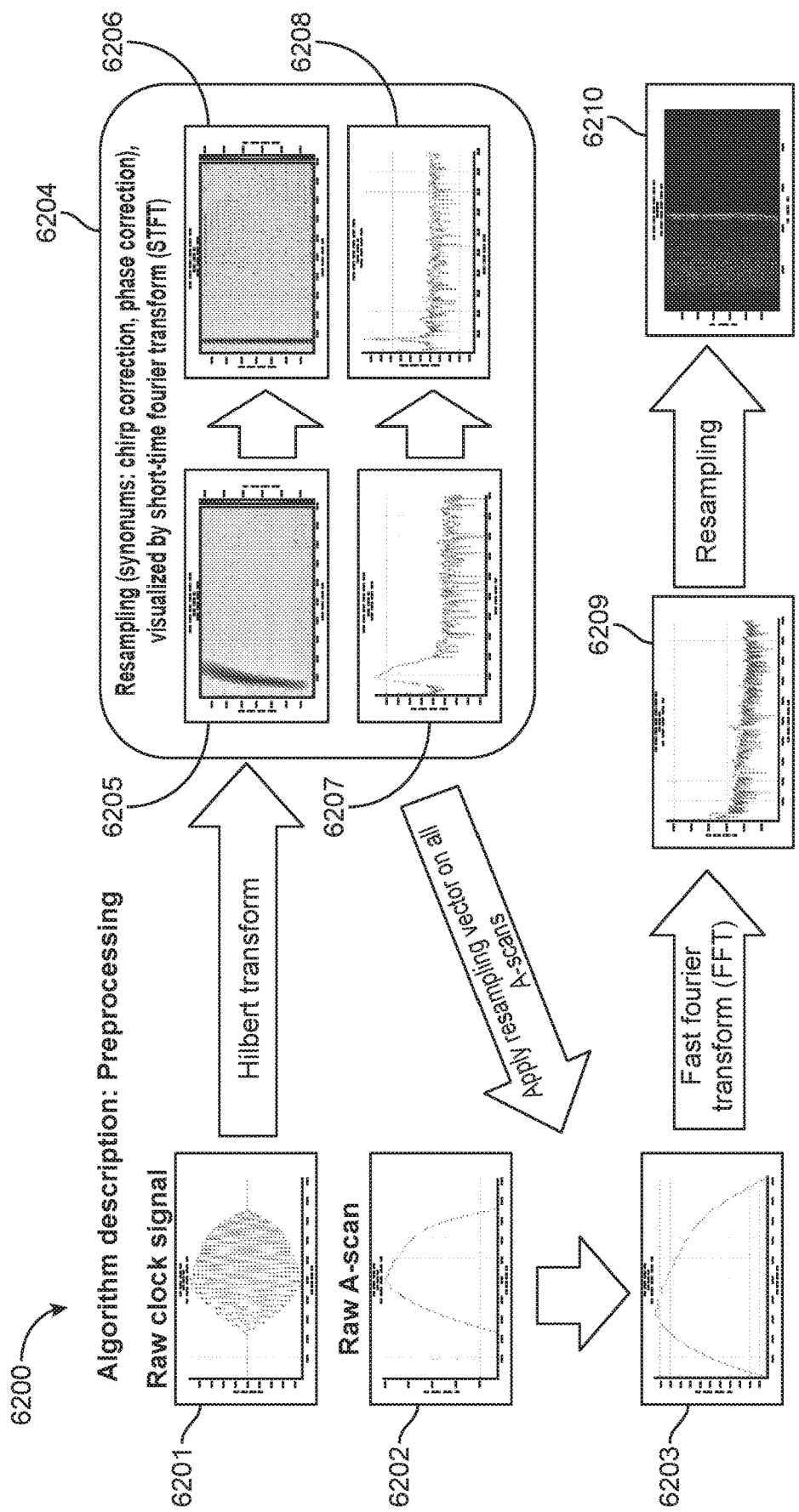
FIG. 16A shows a flow diagram of processing such as preprocessing that may be performed by the OCT system as described herein such as binocular OCT, in accordance with some embodiments.

FIG. 16A shows a flow diagram 6200 of processing such as preprocessing that may be performed by the OCT system as described herein such as binocular OCT 4900, in accordance with some embodiments. A raw clock signal 6201 is received from the detector of the phase compensation module during an A-scan sweep of the swept source as describe herein. The raw clock signal may comprise analog values from the detector after the sampled portion of the swept source light beam is passed through an interferometer such as an etalon as described herein. A raw A-scan sample 6202 is received from the balanced detector of the OCT measurement system as described herein. In some embodiments, the clock signal is synchronously captured with the A-scan signal, in order to accurately resample the A-scan and correct for variations in the rate of wavelength sweeping of the swept source as described herein. The raw clock signal can be transformed with a Hilbert transform, and the resulting phase information can linearized and used to generate a resampling vector 6204. The resampling to generate the resampling vector may comprise one or more of chirp correction, or phase correction.

Short-time Fourier transform (STFT) can be applied to the raw clock signal and visualized in a time-frequency diagram. An image 6205 illustrates non-linear phase of the chirp on the raw clock signal. An image 6206 shows similar information after resampling the raw clock signal with the resampling vector. This operations provided with respect to image 6205 and image 6206 are illustrative to show the effectiveness of chirp correction. Image 6207 shows the result of an FFT applied to the raw clock signal to illustrate peak broadening. Peak broadening can be due to non-linear phase of the chirp signal from the optical clock. Image 6208 shows the result an FFT after resampling the clock signal similar to decrease phase variations of the clock signal, similarly to image 6206, and the peak broadening is significantly reduced. In some embodiments, the resampling is applied to the raw A-scan 6202, and the additional steps described with reference to images 6502, 6206, 6207 and 6208 are not performed, and these images are provided to illustrate the utility of resampling.

The resampling vector is applied to the A-scan data to generate a resampled A-scan 6203. The resampled A-scan is subject to a transform such as a fast Fourier transform to generate intensity values of an individual A-scan 6209. The above process can be repeated to generate a plurality of A-scans. The plurality of A-scans can be resampled to generate a resampled A-scan output 6210 comprising a plurality of A-scans. The resampled output can be used to determine the retinal thickness as described herein.

Figure 16B:
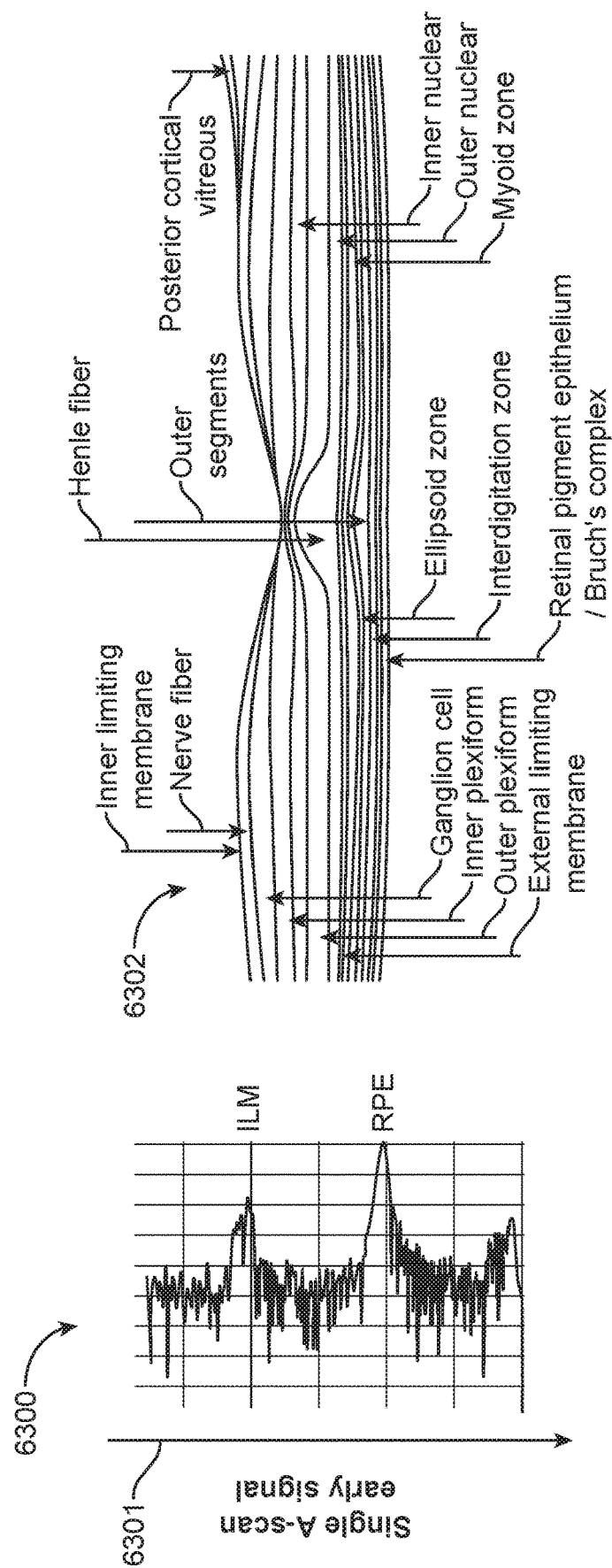
FIG. 16B shows various plots obtained by the preprocessing of flow diagram of FIG. 16A, in accordance with some embodiments.

FIG. 16B shows various plots obtained by the preprocessing of flow diagram 6200 of FIG. 16A, in accordance with some embodiments. A single A-scan 6301 comprises reflections corresponding to layers of the retina 6302 as indicated by A-scan signal 6301. The retina 6302 comprises several layers and structures including the inner limiting membrane ("ILM"), the nerve fiber layer, the ganglion cell layer, the inner plexiform layer, the outer plexiform layer, the external limiting membrane, the Henle fiber, outer segments, the ellipsoid zone, the interdigitation zone, the retinal pigment epithelium ("RPE"), Bruch's complex, the posterior cortical vitreous, the inner nuclear layer, the outer nuclear layer, and the myoid zone. As can be seen with reference to single A-scan 6301, the reflected signal from the retina comprises a first peak corresponding to the ILM, and a second peak corresponding to the RPE. The retinal thickness can be determined based on the separation distance between the ILM and the RPE. Several A-scans 6303 can be resampled and/or combined to generate combined and/or oversampled waveform data 6304 comprising reflectances of the retina at depths. For example, from 100 to 1000 A-scans can be obtained and resampled and/or oversampled, e.g. 700 samples, to generate the thickness of the retina at a region of the retina corresponding to locations of the measurement beam during the A-scans. The resampled and/or combined data 6304 can be used to determine the location of the RPE and ILM based on the corresponding peaks, and the distance between the two reflectance peaks used to determine the thickness of the retina.

Figure 17:
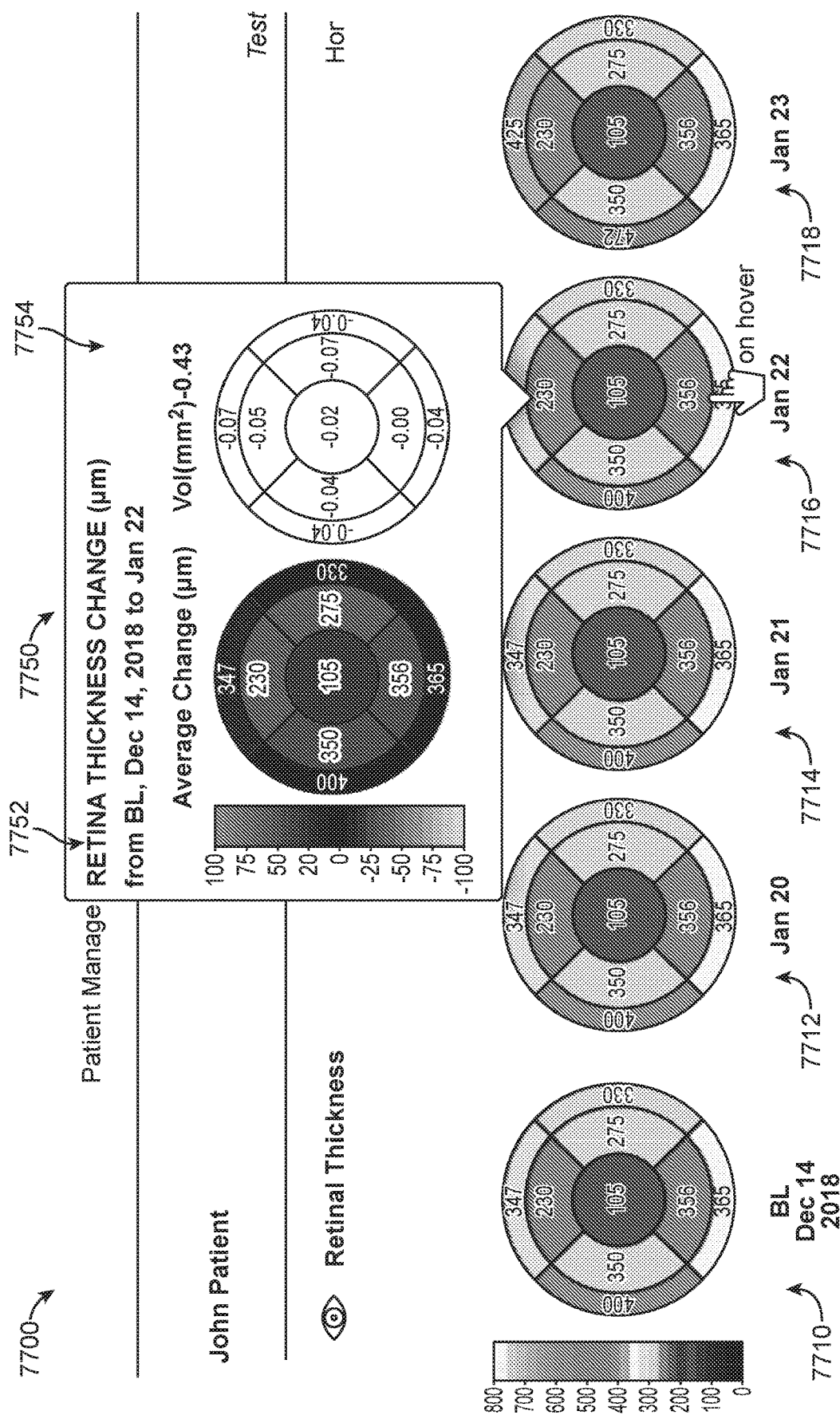
FIG. 17 shows a plurality of output maps of retinal thickness, in accordance with some embodiments.

FIG. 17 shows a plurality of output maps 7700 of retinal thickness in accordance with some embodiments. The plurality of images may be shown on a display as described herein. The plurality of output maps may comprise a first output map 7710 from a first OCT measurement on a first day, a second output map 7712 from a second OCT measurement on a second day, a third output map 7714 from a third OCT measurement from a third day, a fourth output map 7716 from a fourth OCT measurement from a fourth day and a fifth output measurement 7718 from a fifth day.

A difference map 7750 shows a difference between an earlier measurement and a selected measurement. The user interface may comprise instructions to receive user input for a user to select a map. In response to the user selection of a map on from specific day, e.g. with a cursor, the processor is configured with instructions to generate a difference map between a baseline map and the selected map.

Each of the plurality of output maps and difference maps comprises a plurality of sectors. The plurality of sectors may comprise a central sector bounded a plurality of annular sectors. The plurality of annular sectors may comprise an inner annular sector and an outer annular sector. Each of the annular sector may comprise four quadrants, such as a left quadrant, a right quadrant, an upper quadrant and a lower quadrant. The thickness of the retina can be displayed in each of the plurality of sectors with a numeric value shown in each sector, and colored in accordance with the retinal thickness for each sector. The color coding can be continuous within each sector, or graded in response to the actual retinal thickness measurements.

The difference maps 7750 can be configured in many ways, and may comprise a map 7752 showing change thickness shown with a numerical value for each of the plurality of segments. The change in thickness can be color coded in accordance with the change in thickness, and the for each sector of the difference map. The difference map may comprise a difference map showing changes in the volume of the retina for a particular sector, which can be calculated based on the cross-sectional area of the sector and the change in thickness.

Additional data can be provided with each of the difference maps, such as a patient identifier. Also, the alignment of the eye relative to the OCT measurement system during the OCT scan of the retina as described herein. For example, the average alignment and one or more of the X, Y and Z coordinate references as described herein is shown with the map, with appropriate transformation to the coordinates of the map shown on the display. The maps can be presented in many ways, and may comprise numeric values, or colors, such as colors corresponding to values such as thickness. In some embodiments, the maps comprise indicators of data quality such as numeric values, or colors, corresponding to values such as data quality, which can be helpful to assess the reliability of the data used to generate the map. Alternatively, or in combination, the maps can be adjusted in response the measured position of the eye as described herein, so as to center the map about a location corresponding to zero alignment error, for example.

Although FIGS. 4 to 13 refer to a binocular OCT device, one or more of these components can be incorporated into a compact OCT device 100 as described herein, which can be monocular or binocular. The components of binocular OCT device 4900 described with reference to FIGS. 4-13 can be combined to provide a compact monocular OCT device 100, as will be apparent to one of ordinary skill in the art. In some embodiments, the compact OCT device is configured to be mounted on a stand. In some embodiments, the compact OCT device 100 comprises internal translation stages to automatically align the eye of the patient with the OCT beam as described herein.

The monocular OCT device 100 may comprise the handheld OCT device 100 of FIGS. 2, 3A and 3B, and may comprise communication circuitry and be configured to operatively couple to one or more external devices such as mobile patient device 120 as described herein. This connection can be wired, e.g. with a USB connector, or wireless, e.g. with Bluetooth, as described herein. Mobile patient device 120 can be configured to process one or more of the signals from detectors of the monocular OCT device 100, such as signals from detectors 5101-1 to 5101-5, to generate an A-scan and retinal maps as described herein, for example.

FIGS. 18A to 18D show a perspective cut-away view of a monocular OCT device 100. In some embodiments, the OCT device 100 includes a head 202, a base 204, and a neck 206 joining the head to the base. According to some embodiments, the head 202 includes a single eyecup 4901 and facilitates measuring a single eye at a time. A protruding portion 216 of the eyecup can be provided to align an eye of a user to the device 100 and alternatively be used to detect whether the eye being tested is the right eye or a left eye of a user as described herein. Other shapes of the eyecup 4901 are contemplated herein, for example, the eyecup 4901 may be symmetric and one or more sensors, such as infrared sensors, can be used to detect the nose or other facial features of the patient in order to determine which eye is being scanned. The head includes an optics support 1802 that provides a moveable support for the optics contained within the OCT device 100 as described herein.

While the eyecup 4901 can be configured in many ways, in some embodiments, the eyecup 4901 comprise a patient support that the patient can rest on to support the head and eye of the patient during measurements. In some embodiments, the translation stage and optics are configured to move while the patient support such as eyecup 4901 remains substantially fixed, for example with support from the neck 206 and base 204. Although an eyecup 4901 is shown, the patient support may comprise additional or alternative structures such as one or more of a chinrest or a headrest, for example.

The lens 4916 may be part of a free space RT optics 4910 that is configured to provide a fixation target and measure a retinal thickness of the user's eye. The lens 4916 may be adjustable to match the user's refraction, as described herein.

The head 202 includes various components, such as the components illustrated and described in relation to FIGS. 4 and 5 herein. For instance, the OCT device 100 includes free space RT optics 4910, which may comprise an RE correction module 4911 as described herein. The free space RT optics 4910 may include a fixation target 4912 and a hot mirror as described herein. An optics support 1802 may comprise a motorized stage 1803 configured to move the optics components in one or more of X, Y, or Z directions. The optics support may be driven by motors, linear actuators, sliders, or any suitable structure that can move the optics support.

In some embodiments, a lens displacement motor 1804 is configured to advance or retract the lens in a Z direction to adjust for RE correction and/or OPD distance. Other motors may be provided to adjust the lens vertex, an X-motor 1806 for translation along the X axis, a Y-motor 1808 for translation along the Y axis, and a Z-motor 1810 for translation along the Z axis for alignment of the optics with the eye of the user. In some embodiments, the alignment is done automatically by the OCT device 100. Additional motorized components may adjust the optics for automatic focus adjustment.

The OCT device 100 may include a scanner module 4990 that scans the laser light from one or more VCSELs in a pattern, as described herein. The scanner module 4990 may include a peripheral board 4915, sealing window, free space 2d scanner, and relay optics as described herein. The OCT device 100 may further include an OPD correction module 4940 which may include a peripheral board 4915, motorized stage and OPD motor 1812, and fiber collimator 4941 as described herein. The OCT device may additionally include a Fabry Perot clock box 4962, as described herein. The OCT device 100 may include other components, such as those described in relation to embodiments herein, which may include without limitation, a scanner module 4990, Re-correction module 4911, and a fixation target 4912.

Figure 18A:
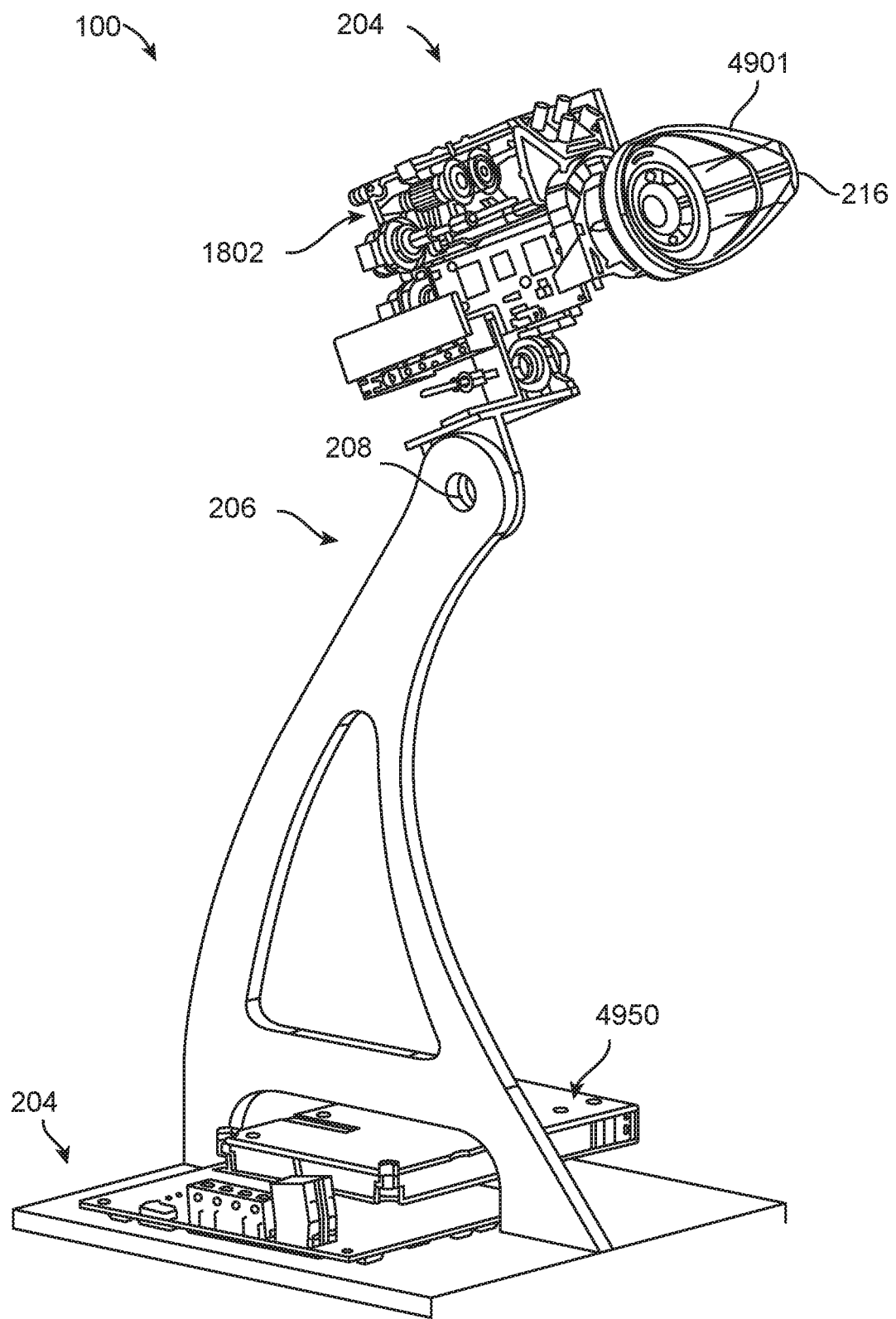
FIG. 18A shows a perspective/cut-away view of a monocular OCT device, in accordance with some embodiments.
Figure 18B:
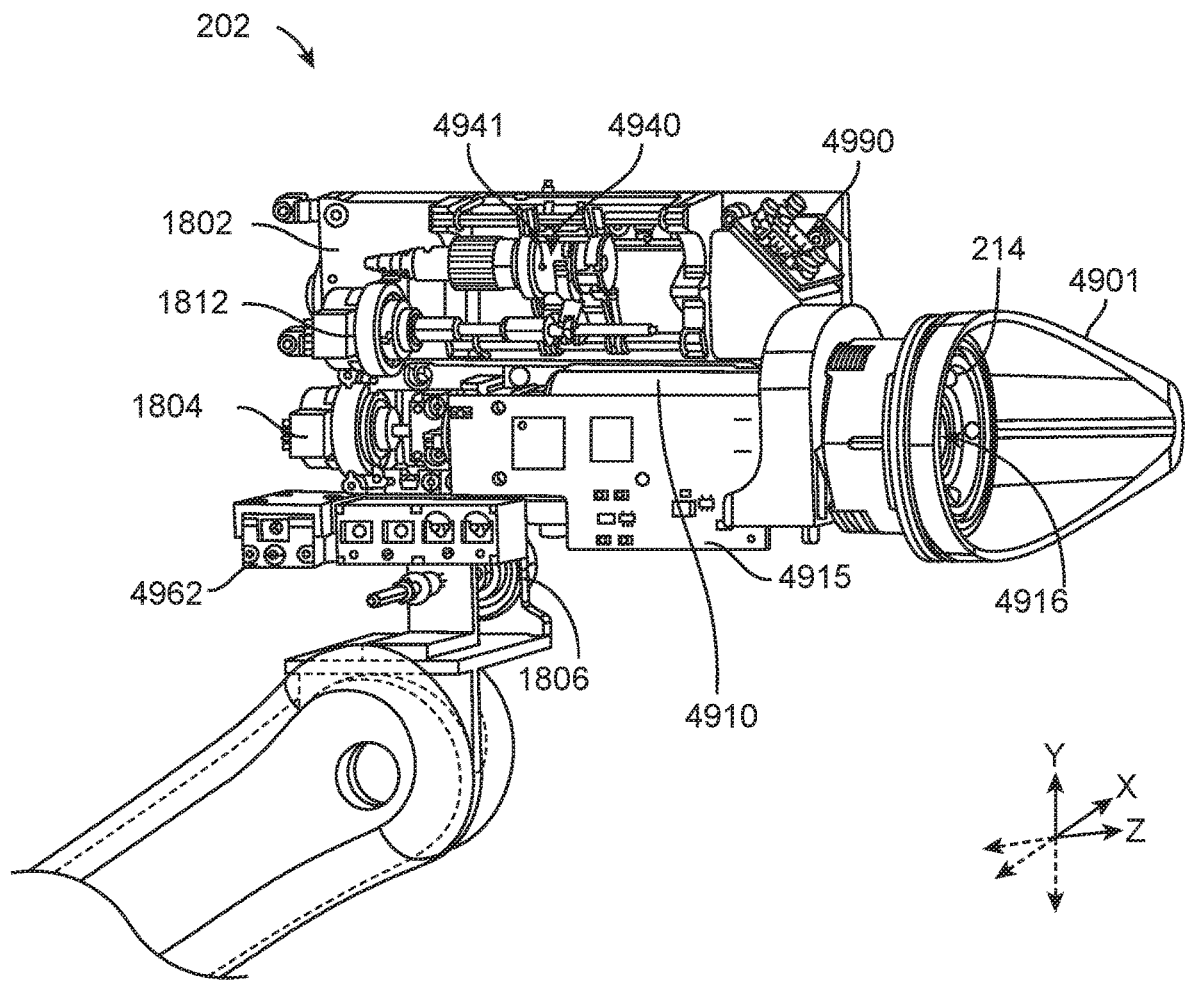
FIG. 18B shows a perspective/cut-away view of a head portion of the monocular OCT device as in FIG. 18A.
Figure 18C:
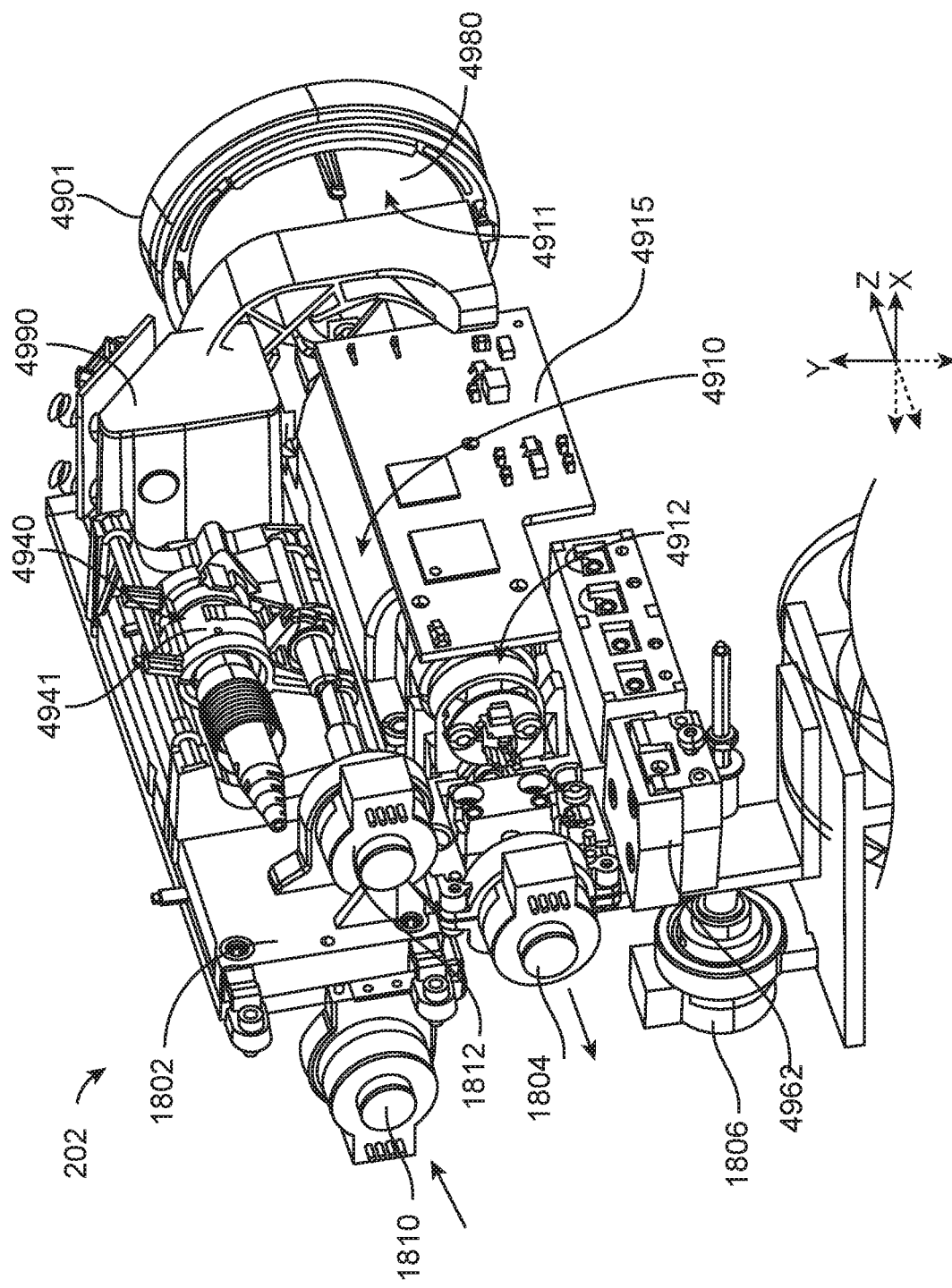
FIG. 18C shows a perspective/cut-away view of a head portion of a monocular OCT device as in FIGS. 18A to 18B.
Figure 18D:
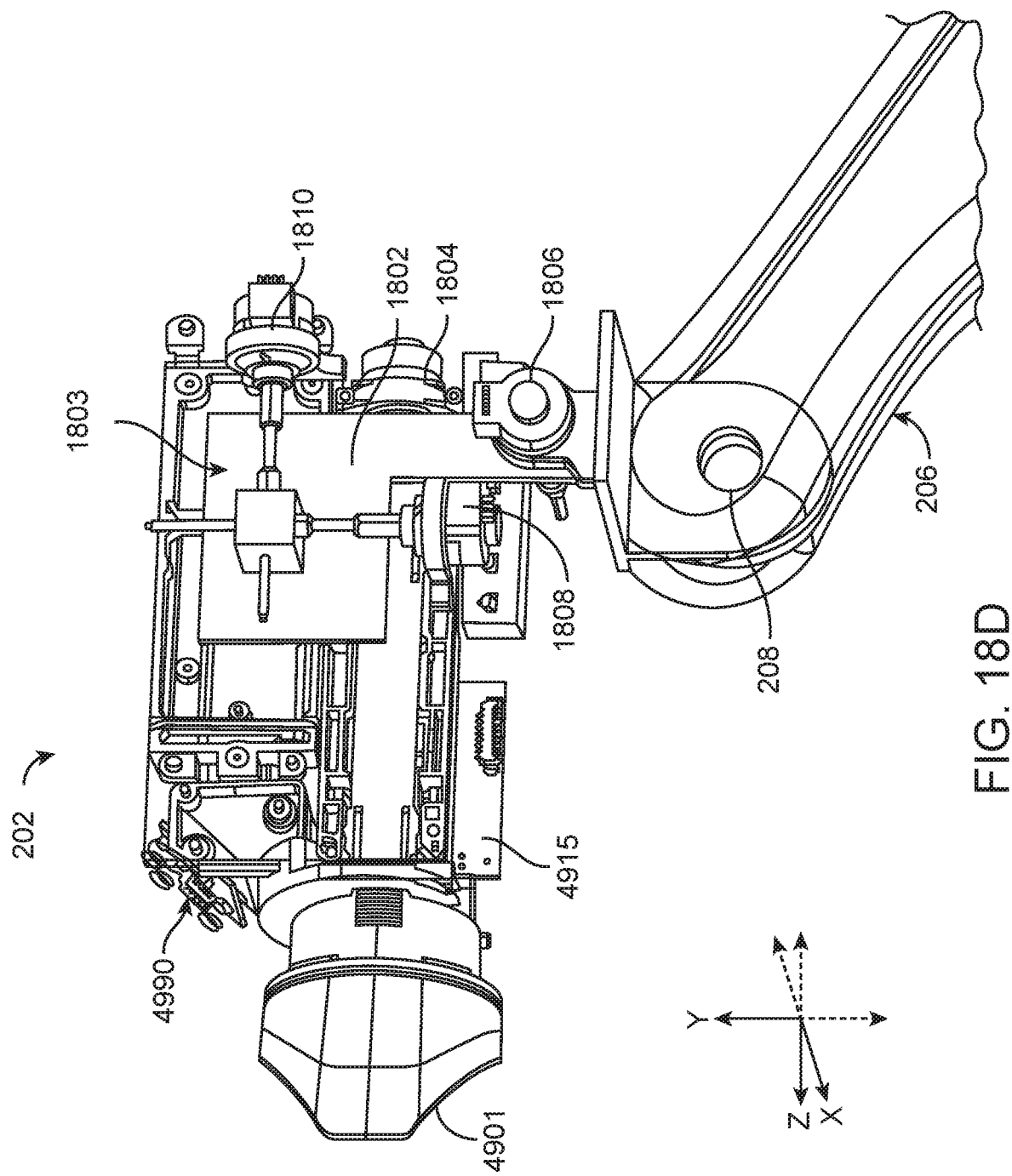
FIG. 18D shows a perspective/cut-away view of a head portion of a monocular OCT device as in FIGS. 18A to 18C.
Figure 18E:
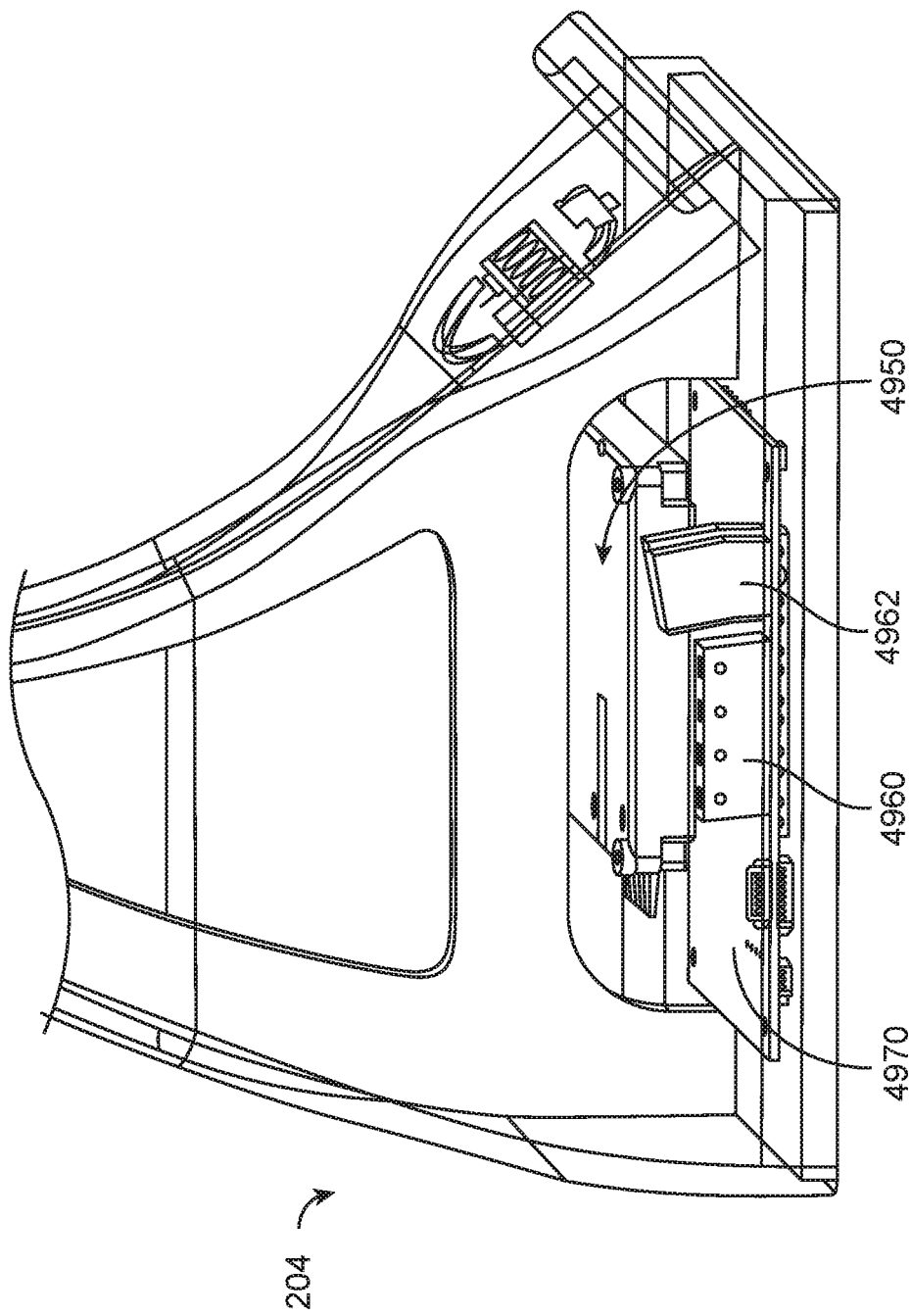
FIG. 18E shows a perspective/cut-away view of a base portion of an OCT device as in FIGS. 18A to 18D.

FIG. 18E shows a base 204 of an OCT device 100, which may include a main electronical board 4970. In some embodiments, the main electronical board 4970 is positioned in the head, while in other embodiments, it is positioned in the neck, the base, or is provided in multiple pieces which may be located in any combination of the head, neck, and/or base.

The base 204 may further include a fiber connector 4960 and a Fabry Perot clock box 4962 as described herein. In some embodiments, the base 204 includes a fibered interferometer module 4950, which may include one or more fiber VCSELs 4952, one or more Fiber Mach-Zender interferometer, and fiber distribution circuitry. As further described herein, laser light from the VCSELs is optically transferred to the fiber distribution module 4953, where a portion of the laser light is optically transferred to a fiber connector 4960 for analysis in the main electronical board 4970. Another portion of the laser light from the VCSELs is optically transferred to an OPD correction module 4940 and ultimately to the free space RT optics 4910 for delivery to a user's eye in order to measure the user's eye.

The scanner and associated optics can be configured, as described herein, to scan any suitably sized region of the retina. In some embodiments, the scanner and associated optics are configured for auto focus. In some embodiments, the scanner and associated optics are configured for auto alignment. In some embodiments, the lens and/or the OPD correction module 4940 are configured for linear displacement in the Z-direction.

In some embodiments, an autofocus (AF) system is provided to provide automatic focusing for the patient. In some embodiments, an auto capture (AC) system is provided to automatically capture scans of the user's eye when the device is appropriately aligned with the user's eye. According to some embodiments, the OCT system 100 is configured to adjust and align to the user's eye, adjust the refractive error, and optical path difference of the OCT device 100. In some embodiments, the RE and position of the OCT optics are adjusted. In other embodiments, the RE and OPD are adjusted.

In use, XY alignment images may be displayed to a user. The XY alignment images may comprise one or more Purkinje images displayed on the cornea of a user's eye and the position of the OCT optics are moved in one or more of X, Y, and Z directions. In some embodiments, the lens displacement motor is configured to adjust the position of the lens in the Z-direction to the correct vertex distance (e.g., the distance between the OCT lens to the cornea). In some embodiments, the processor is configured to perform the distance adjustments, and in some cases, automatically, by aligning the OCT optics of the monocular OCT device 100 to correctly display a focused image for the user, correcting for RE by iterating the RE signal strength.

The light source to measure the refractive error and compensation can be configured in many ways. In some embodiments, the light source comprises the one or more VCSELs as described herein. The VCSELs can be pulsed at appropriate times with appropriate energy to conform with light safety. The light source to measure the RE may comprise a non-coherent light source. For example, the VCSEL can be driven below the lasing threshold and used as a super luminescent diode to provide a non-coherent source of light. Alternatively, a separate light source can be coupled to the optical fiber comprising the measurement leg of the interferometer, and light non-coherent light emitted from the end of the optical fiber.

The base 204 of the OCT device 100 may include components configured to receive information, transmit information, power the device, and/or collect information associated with use of the OCT device 100. In some embodiments, the base includes a fibered interferometer module 4950 along with associated electronics as described herein. The base may include a power supply that provides power to the OCT device 100, such as through alternating current power or direct current power. The base provides a stable platform to support the neck and the head in a stable way to resist toppling. In some embodiments, the base may include one or more weighted structures to influence the center of gravity of the OCT device 100 to improve stability than an OCT device without weighted structures.

Referring again to FIGS. 18B, 18C, and 18D, which show perspective/cut-away views of embodiments of the OCT device as in FIG. 18A.

In some embodiments, the OCT device 100 includes a head 202 having an adjustable lens 4916 that is optically coupled to an OCT measurement system and a fixation target 4912 as described herein. The free space RT optics 4910 comprises a fixation target 4912 that allows a user to fixate with one eye, as described herein.

The free space RT optics 4910 may also comprise a RE correction module 4911 as described herein, that comprises the lens 4916. The lens can be moved to preprogrammed positions corresponding to the refractive error of the user's eye. A peripheral board 4915 can provide electronic control over a motorized stage 1803 to correct for the refractive error of the user's eye viewing the fixation target 4912 of the OCT device 100, as described herein.

In some embodiments, the OCT device 100 comprises a fibered interferometer module 4950 that comprises a single VCSEL or a plurality of VCSELs 4952 as described herein. The one or more VCSELs within the fibered interferometer module 4950 are optically coupled to a fiber distribution module and further coupled to the fiber Mach-Zender interferometer 4951, as described herein. The one or more VCSELs may be driven and operated as described herein.

The scanner module 4990 and associated optics can be configured to scan any suitably sized region of the retina, as described herein.

According to some embodiments, an OCT device 100 can be provided to a patient without being specifically configured for the patient prior to being provided to the patient. For instance, an OCT device 100 may be purchased, delivered, loaned, rented, or sold to a user without programming the OCT device 100 for a particular user. This facilitates providing OCT devices 100 to new users without any prior knowledge about the user setup of the OCT device 100 before the user takes possession. The OCT device 100 may be set up for remote access, data transfer, or configuration through any communication methodology as described herein.

According to some embodiments, the OCT device 100 uses one or more of an auto capture (AC) and autofocus (AF) system. According to some embodiments, only the refractive error and position of a portion of the OCT optics are adjusted. According to some embodiments, both the refractive error and the OPD are adjusted.

In some embodiments, the OCT device 100 automatically adjusts to the eyes of a user, by adjusting to a single eye at a time and measuring a single eye. For example, XY alignment is performed by utilizing Purkinje images that are reflected off the cornea of the user, as described herein. A user may fixate their gaze on a fixation target, and the free space RT optics 4910 can be moved left, right, up, down, in, and/or out, such as by moving the optics support by actuators, motors, or the like, in order to align the free space RT optics 4910 with the eye of the user.

According to some embodiments, one or more LEDs 214 provide illumination to facilitate XY alignment of the free space RT optics 4910 with the eye of the user. In some embodiments, the scanning beam pivots near the pupil plane and is imaged into the eye. The optics image the one or more scanning mirrors to a location near the pupil plane and the beam pivots at the imaged location. Although reference is made to scanning mirrors, in some embodiments the scanning is provided by a single mirror which pivots about two axis, for example with a gimbal configuration.

In some embodiments, the OCT device 100 comprises a translation stage 1803 to align the components mounted on the optics support with the eye. The translation stage 1803 may comprise a three-axis translation stage configured to move the optics support along each of three axes, such as an XYZ translation stage. The translation stage 1803 may provide translation along a first axis, such as an X axis, which is coupled to an X axis actuator, such as an X motor 1806. The translation stage may provide translation along a second axis, such as an Y axis, which is coupled to a Y axis actuator, such as a Y motor 1808. The translation stage may provide translation along a third axis, such as an Z axis, which is coupled to an Z axis actuator, such as a Z motor 1810. As described herein, the X and Y axes generally correspond to translational movement along a plane transverse to the OCT measurement beam path into the eye, and the Z axis corresponds to movement along the OCT measurement beam path.

In some embodiments, the OCT device comprises additional actuators supported with the translation stage to provide movement of additional optical elements with reference to the three-axis translation stage. For example, a fourth actuator such as the lens displacement motor 1804 can be configured to move the lens 4916. A fifth actuator can be coupled to the OPD correction 4940. The fifth actuator may comprise an OPD motor 1812. The fifth actuator can be configured to move the OPD assembly 4940 to adjust the optical path difference between the measurement arm and the reference arm of the interferometer. The OPD assembly may comprise an end of the optical fiber from the measurement arm of the interferometer and a collimation lens, both of which are configured to move to adjust the optical path length of the measurement arm of the interferometer.

In some embodiments, the OCT device 100 corrects for refractive error. The OCT device 100 transmits an OCT beam (such as from an optical fiber) through the cornea to the retina and a detector measures the intensity of the reflected light as described herein. The translation of the optics support may cause the free space RT optics 4910 to translate in the direction toward the patient, e.g. in the Z direction. In some embodiments, when the free space RT optics 4910 (which includes the lens 4916) translates toward the user with movement of the translation stage, the lens 4916 translates in an opposite direction relative to the optics support with actuation of the lens displacement motor, thereby maintaining a substantially constant vertex distance between the lens and the cornea of the user. This displacement in opposite directions is shown with arrows in FIG. 18C. The substantially constant vertex distance may comprise a distance that remains constant to within about +/−1.5 mm.

This movement of the front lens, e.g. lens 4916, lens 4916-1 with the fourth actuator, such as the lens displacement motor, also changes the distance between the fixation target and the lens so as to adjust the vergence of the fixation target so as to compensate for the refractive error of the eye. For example, when the translation stage moves the fixation target, e.g. fixation target 4912-1, toward the eye, the front lens is moved toward the fixation target to provide a vergence of the target that corrects for myopia while also setting the vergence of the OCT beam to correspond to the refractive correction. This coordinated movement of the RE correction module 4911-1 and the translation of the translation stage with the Z actuator allows the vertex distance to be maintained at a substantially constant distance while the refractive error is adjusted.

In some embodiments, this coordinated movement of the OCT translation stage and front lens allows the OCT device 100 to set the strongest focus without relying on the OCT coherence signal. The lens 4916 may translate across the range of available refractive error, such as by moving the free space RT optics 4910 while maintaining the lens 4916 at a substantially constant distance from the cornea of the user. By moving the free space RT optics 4910 toward the patient and moving the lens 4916 with a corresponding speed and/or distance, the refractive error can be corrected by determining the position of the free space RT optics 4910 at which the strongest intensity of light signal is received back from the eye. In some instances, correcting for the refractive error, as described, does not affect the OPD adjustment. The process of moving the free space RT optics 4910 and measuring the reflected light intensity can be iterated to determine the strongest intensity signal of the light beam from the OCT light source. In some embodiments, the correction for the OPD can be made once the correction for refractive error has been established with translation of the OPD correction 4940. However, in some embodiments, the OCT measurement light beam comprises a sufficient coherence length to provide a substantial interference signal without the OPD correction. Alternatively or in combination, in some embodiments the reflected light interference signal intensity is adjusted by iteration, for example so as to be centered within the coherence length of the device.

According to some embodiments, once the RE has been calibrated, this information may be stored in a memory, or on a remote device, for later recall. For example, the position of the free space RT optics 4910 may be stored in a memory and associated with a user for a subsequent scan of the eye of the user. Additional data, such as user identification, identification of which eye corresponds to the RE calibration, date, time, and other information may be stored relating to the RE correction for a particular eye of a particular user. In some cases, the RE calibration need only be performed once. In other cases, the RE calibration is performed a number of times that is less than the number of scans of the eye of a user. For example, the RE calibration may be performed once for every two eye scans, or every three eye scans, or every four eye scans, or every five or more eye scans.

According to some optional embodiments, the OPD is adjusted as described herein, for example with OPD correction 4940 and translation of the OPD actuator, such as the OPD motor 1812. In some embodiments, the OPD is adjusted after the RE compensation has been performed. In some embodiments the OPD is adjusted by activating the interferometer and providing a swept source OCT and determining the fidelity (e.g. the strength of the signal) in response to translation of the OPD correction. In some cases, if the initial signal to noise ratio is above a threshold, then the OPD setting is appropriate for the scanned eye. In some cases, where the initial signal to noise ratio is below a threshold, the OPD motor may be activated and the OPD correction module 4940 may be translated in the Z-direction to a location where the signal to noise ratio is above the threshold. In some cases, the OPD correction module 4940 may be translated a distance, such as 1 mm, or in 1 mm increments until the signal to noise ratio is above a threshold. According to some embodiments, the signal to noise ratio is determined at each Z location of the OPD correction module 4940 and a peak signal to noise ratio is determined. In some embodiments, the OPD correction module 4940 is located to correspond with the peak signal to noise ratio.

According to some embodiments, the OPD correction 4940 is not present, such that the end of the optical fiber from coupler 5122 and collimation lens 5112 (as shown in FIG. 6) remain fixed relative to the optics support. In such embodiments, the system processor can be configured with instructions to improve the OCT interference signal by translating the optics support with the with the translation stage. Work in relation to the present disclosure suggests that the translation of the optics support can be used to implement OPD correction, and that movement of optics support will result in only a nominal change in the refractive compensation and the size of the measurement beam on the retina of the patient. In those embodiments where OPD correction 4940 is unavailable, the OCT device 100 may first adjust the refractive compensation with the substantially constant vertex distance. Once the refractive compensation is determined, the OCT device 100 may translate the optics support with the translation stage to adjust the length of the measurement arm of the OCT system, in order to provide an improved signal to noise ratio of the interference signal. According to some embodiments, once the system is aligned with the eye, the refractive error compensation determined, and the OPD adjusted with movement of the translation stage, the OCT device 100 will be ready to acquire retinal OCT interference data and determine retinal thickness data.

Alternatively, the OPD actuator can be adjusted to acquire the strongest interference signal, while the fixation target is adjusted to compensate for refractive error.

According to some embodiments, the OCT device 100 can actively track user movement, such as by tracking the XY position of the eye of a user over time with the position sensor. In some embodiments, the OCT device 100 may auto adjust to compensate for a position of the user's eye through active tracking and XY control of the free space RT optics 4910, for example with XY movement of the translation stage. Alternatively or in combination, the OCT device 100 can monitor alignment of the user's eye with the position sensor, and if during a scan, alignment data falls outside an acceptable parameter, then the test can be repeated. For example, alignment data may comprise an alignment distance, an alignment time, an alignment percentage, an alignment angle, or some other data associated with the dimensions of alignment during the time of the scan. If one or more of these values is outside a predetermined range, the user can be prompted to repeat the scan until the one or more values are within the predetermined range.

Figure 19:
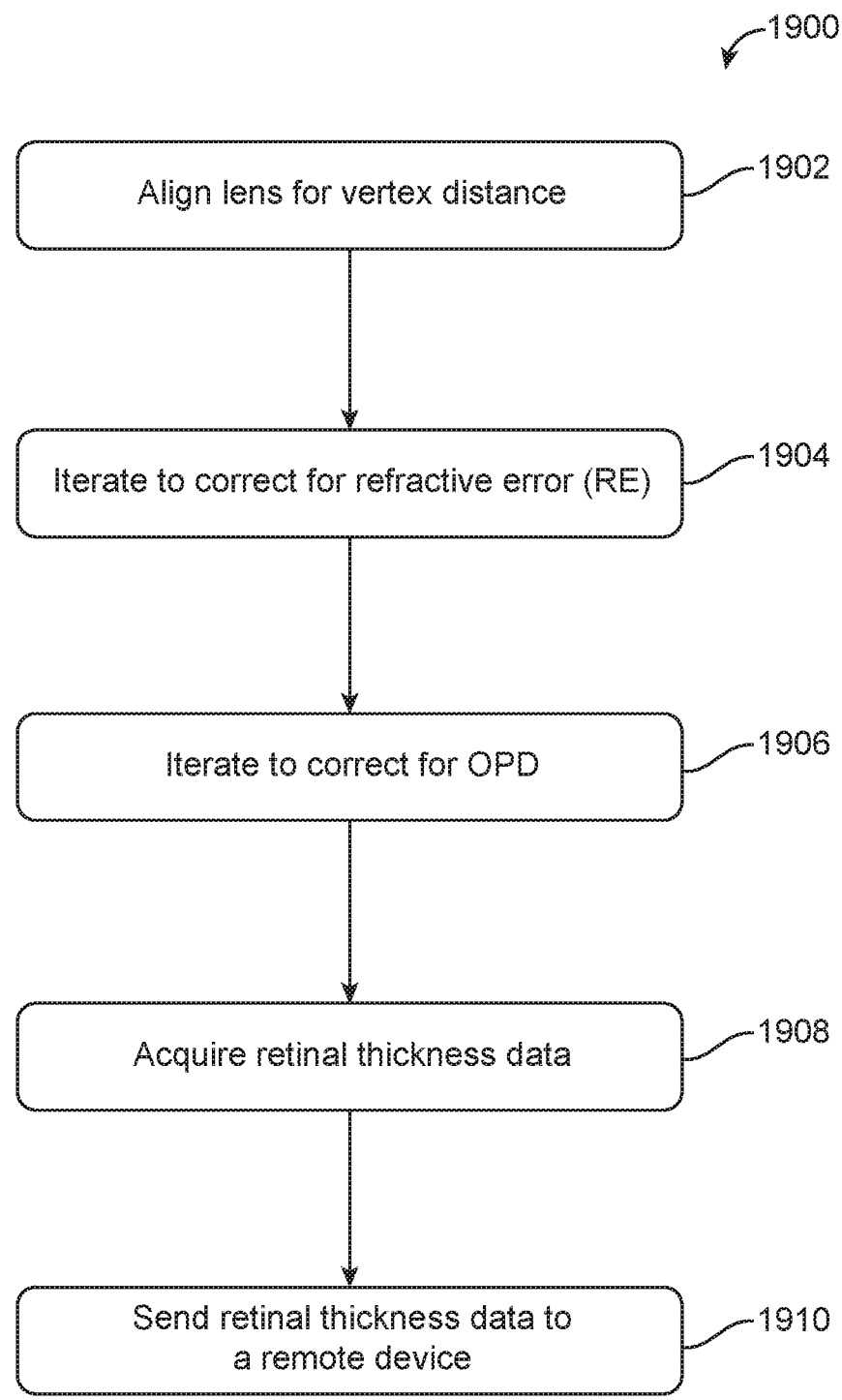
FIG. 19 shows a sample flow diagram for measuring retinal thickness with an OCT device, in accordance with some embodiments.

FIG. 19 shows process steps 1900 for scanning an eye with an OCT device according to some embodiments. At step 1902, a front lens is aligned to set the vertex distance to a targeted vertex distance with a position sensor as described herein. According to some embodiments, a fixation target is presented for a user to gaze at while the position of the eye is measured to determine the vertex distance. The device may transmit a pattern comprising one or more lights or other suitable patterns, such as a grid, onto a cornea of a user to generate a Purkinje image. The device may move the optics support in one or more of X, Y, or Z directions to align the eye with the OCT optics in response to the Purkinje image. In some embodiments, the OCT optics image the one or more scanning mirrors to a location near the pupil plane, and the location of the image and corresponding pivot within the eye translates with the OCT optics on the translation stage.

At step 1904, the device corrects for refractive error, for example with adjustment of the distance between the front lens and the fixation target as described herein. According to some embodiments, a beam from the OCT light source is transmitted into the eye of a user, and a detector will measure the intensity of the beam reflected from the retina of the user. In some embodiments, the beam intensity is measured without capturing an interference signal from the measurement arm and the reference arm of the interferometer. The actuators of the translation stage coupled to the optics support move the free space optics toward or away from the eye of the patient, and a lens displacement motor moves the front lens in a opposite direction to substantially maintain the vertex distance, such that the combined displacement of the free space optics and the lens displacement motor cause the front lens to remain at a substantially constant distance from the eye of the patient. The system may determine an intensity of the light reflected from the retina in response to movement of the free space optics and the lens, so as to determine the refractive compensation of the eye. The system may determine a peak reflectance signal in response to the movement of the free space optics and the lens. The system may iterate to determine the peak reflectance signal. The reflectance signal may be based upon luminance of the OCT beam being reflected to the detector. In some embodiments, the end of the optical fiber and corresponding collimation lens comprise a confocal configuration, such that the best focus of the light beam on the retina corresponds to the peak reflectance signal.

At step 1906, the device corrects for OPD, for example with movement of the end of the optical fiber of the measurement arm of the interferometer as described herein. According to some embodiments, the OPD is adjusted and the fidelity (e.g. signal to noise ratio of the interference signal) of the OCT data is determined. The OPD adjustment is iterated and a maximum fidelity (e.g., highest signal to noise ration) of the OCT data is determined. According to some embodiments, the end of the optical fiber of the measurement arm of the OCT system is translated away from the eye of a user in the Z-direction to increase the fidelity of the OCT data. In some embodiments, maintaining the vertex distance of the front lens substantially fixed and moving the optics support toward the eye to decrease the separation distance between the front lens and the fixation target in order to compensate for myopia decreases the optical path length of the measurement arm of the interferometer, e.g. the distance between the end of the measurement arm optical fiber and the retina. However, because myopes tend to have an increased axial length of the eye. Moving the end of the optical fiber from the measurement arm away from the retina increases the interference signal, in some embodiments. In some embodiments, this movement of the end of the measurement optical fiber can be provided by moving the optics support and the components supported thereon (e.g. the front lens, the fixation target, the end of the optical fiber and corresponding collimation lens) with the translation stage to increase the measurement path length. Alternatively, the OPD correction can be used to move the end of the optical fiber and collimation lens with the OPD adjustment driven with a fifth actuator as described herein.

At step 1908, the device acquires retinal thickness data, for example with an interference signal from a swept source OCT system as described herein. The RT data may be acquired automatically in response to the alignment of the eye in response to position sensor data as described herein. The RT data may be acquired automatically after the refractive compensation has been determined, for example. The RT data may be acquired automatically after the OPD correction has been determined. The RT data may be acquired automatically after both the RE and OPD correction have been determined. The RT data may be acquired by manual actuation, such as by the pressing of a button. The RT data may be acquired in response to a signal from a remote device, or voice activation for example.

At step 1910, the device sends the retinal thickness data to a remote device, for example as described herein.

Figure 20A:
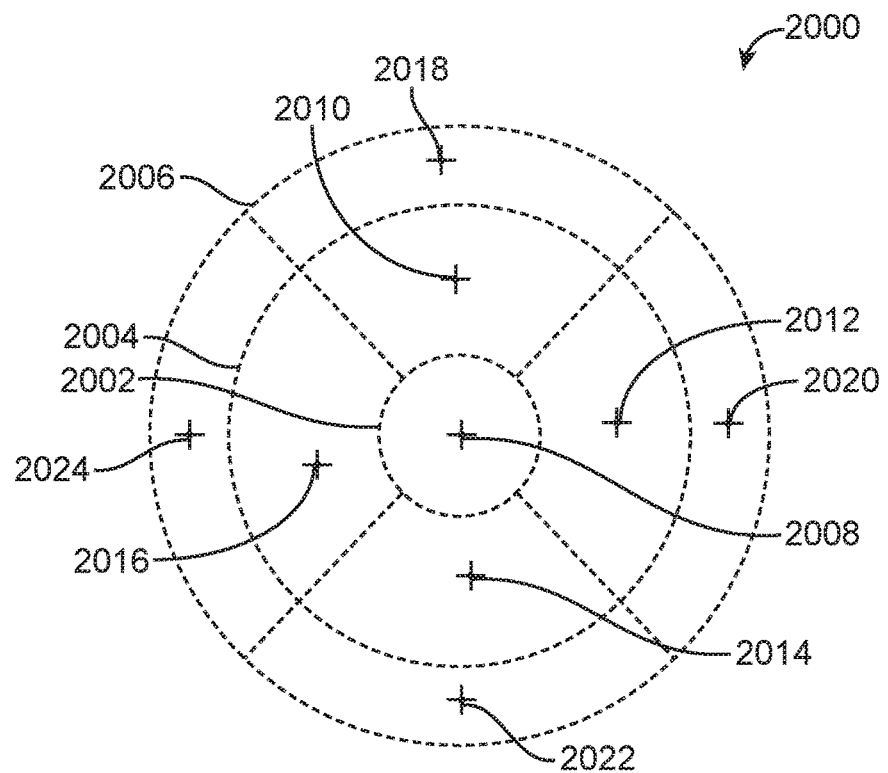
FIG. 20A shows a selectively moveable fixation target, in accordance with some embodiments.

FIG. 20A shows a plurality of positions of a moving fixation target 2000 and corresponding retinal locations, in accordance with some embodiments. In some embodiments, the positions of the moving fixation target are used to extend an effective scanning range of the OCT. By presenting the fixation target at a plurality of locations and scanning an area of the retina for each of the plurality of target locations, the retinal OCT data from each of the corresponding areas can be combined to increase the total area of the retina scanned, and this total scanned area used to generate retinal thickness maps and images, for example. Alternatively, the plurality of positions of the fixation target can be used to generate a retinal thickness map without a scanning mirror. In such embodiments, each of the plurality of positions of the fixation target corresponds to a region of the retinal thickness map. The retinal thickness data is obtained for each of these positions and used to generate the retinal thickness map. In some embodiments, the eye position sensor data is used to adjust the corresponding location of the retinal thickness data on the retinal thickness map.

In some embodiments, after changing the location of the fixation target, the processor is configured with instructions to re-align in X and Y dimensions before acquiring the OCT retinal data for that fixation location. For example, if the location of the center of the pupil changes with a new fixation target location, the processor can be configured to translate the OCT device to approximately center the OCT beam within the pupil, so as to decrease clipping of the OCT measurement beam with the pupil.

The fixation target 2000 may be provided with an OCT device, as described herein. According to some embodiments, the fixation target is moved within the OCT device in order to promote the user moving the eye being tested to measure different portions of the retina and to increase the area of the scan. According to some embodiments, the fixation target is created on a display within the OCT device and the fixation target is moveable on the display. The fixation target may be any suitable target, such as those described herein, and may include a point, a crosshair, an image, a symbol, an emoji, or any other type of target for a user to fix their gaze upon.

The corresponding of retinal locations for the fixation target are shown in dashed lines. The boundaries of the retinal locations may include a center ring 2002, a first ring 2004, and a second ring 2006. Other arrangements are possible and are contemplated herein, such as boundaries corresponding with a square or rectangular area.

According to some embodiments, a first location of the moveable fixation target 2000 comprises a central location 2008 corresponding bounded by ring 2002. While the fixation target is located at the central location 2008, an eye of a user will fixate upon the fixation target and the OCT device can scan the retina and generate OCT measurement data for that location and the corresponding region 2002. In some instances, when a user fixates on the center ring 2002, the OCT system will scan the center of the retina and generate OCT measurement data associated with the central location 2008.

The fixation target may move to other discrete locations, such as a plurality of locations corresponding to each of location 2010, location 2012, location 2014 and location 2016. In some embodiments, these locations correspond to regions of the retinal shown on the retinal thickness map. The OCT measurement data for each of these locations can be obtained. This data can be used to generate a retinal thickness map, or to extend the area of the retina scanned, and combinations thereof.

The OCT system may predetermine one, two, five, twelve, twenty, or more discrete positions in which to display the fixation target in order to collect RT data of the eye of a user. In some embodiments, the RT data is collected, compiled, and used to generate an RT map of a user's eye. The RT map may comprise any level of granularity as desired. For example, a greater number of scans and an RT map with more detail may be generated for a new user, while a fewer number of scans and an RT map with less granularity may be provided as an updated RT map to an existing user.

In some embodiments, the OCT device scans one or more areas of the retina and generates OCT measurement data that provides data about some areas of the retina, but not all areas of the retina. In these embodiments, the OCT device may utilize some of the fixation target locations corresponding with the areas of interest of the retina. As an example, where the OCT device presents a fixation target that causes the eye to rotate to the right, the OCT device can scan an area of the retina corresponding with right side of the retina. In some embodiments, the OCT device, or remote computing resources, may generate the RT map or retinal image based on the OCT measurement data.

According to some embodiments, the optics may be translated to maintain the beam in the center of the pupil. For example, as the eye rotates, the pupil effectively translates and can be measured with the eye position sensor. In other words, the eye rotates about a center of rotation that is behind the pupil. Therefore, as the eye rotates, the pupil approximates a translational movement. The OCT beam may be translated accordingly with the translation stage so that the OCT beam remains centered within the pupil to decrease clipping of the measurement beam, in some embodiments.

According to some embodiments, the fixation target moves slowly through the predetermined positions and a continuous scan of the retina is captured as the eye follows the fixation target. In some embodiments, the OCT measurement data corresponds to the RT map on a one to one basis. That is, each OCT scan of the retina (e.g. with a swept source beam) at the one or more fixation target locations may correspond to a zone of the RT map. In some embodiments, the number of scans of the retina may be more or fewer than the number of zones on the RT map.

Figure 20B:
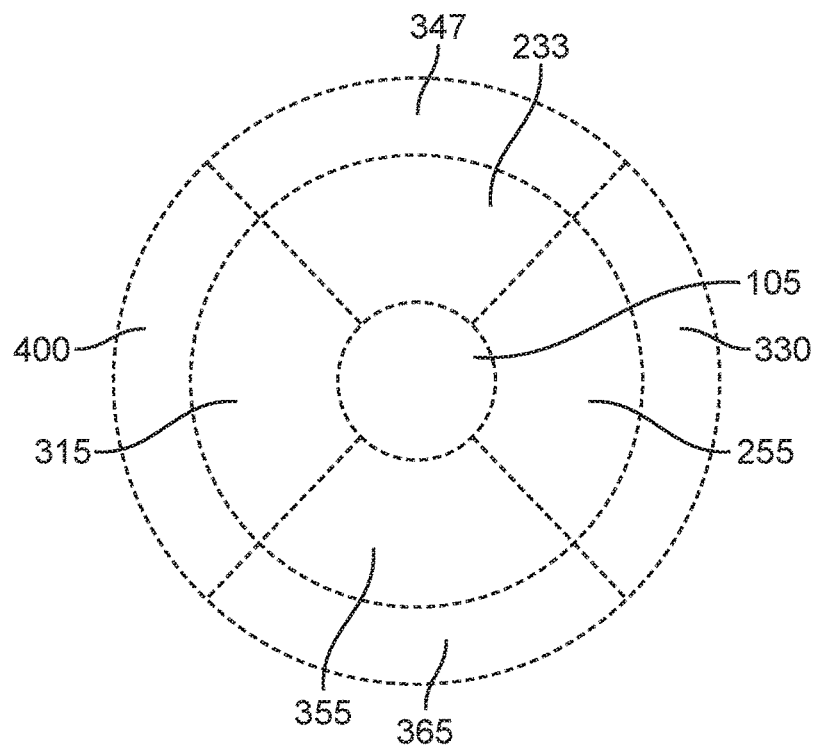
FIG. 20B shows a retinal thickness ("RT") map, in accordance with some embodiments.

FIG. 20B illustrates an RT map in which a plurality of retinal scans produces RT data for various regions of the retina. A plurality of thickness values is shown on the RT map, and each thickness entry may correspond to a single position of the fixation target corresponding to an area of the retina. According to some embodiments, the plurality of thickness values may each correspond to a predetermined position of the fixation target. In some embodiments, the plurality of thickness values is generated based upon a combination of multiple scans of the retina. For example, the thickness values may be the result of an average, or a weighted average of multiple scans of an area of the retina.

Figure 21:
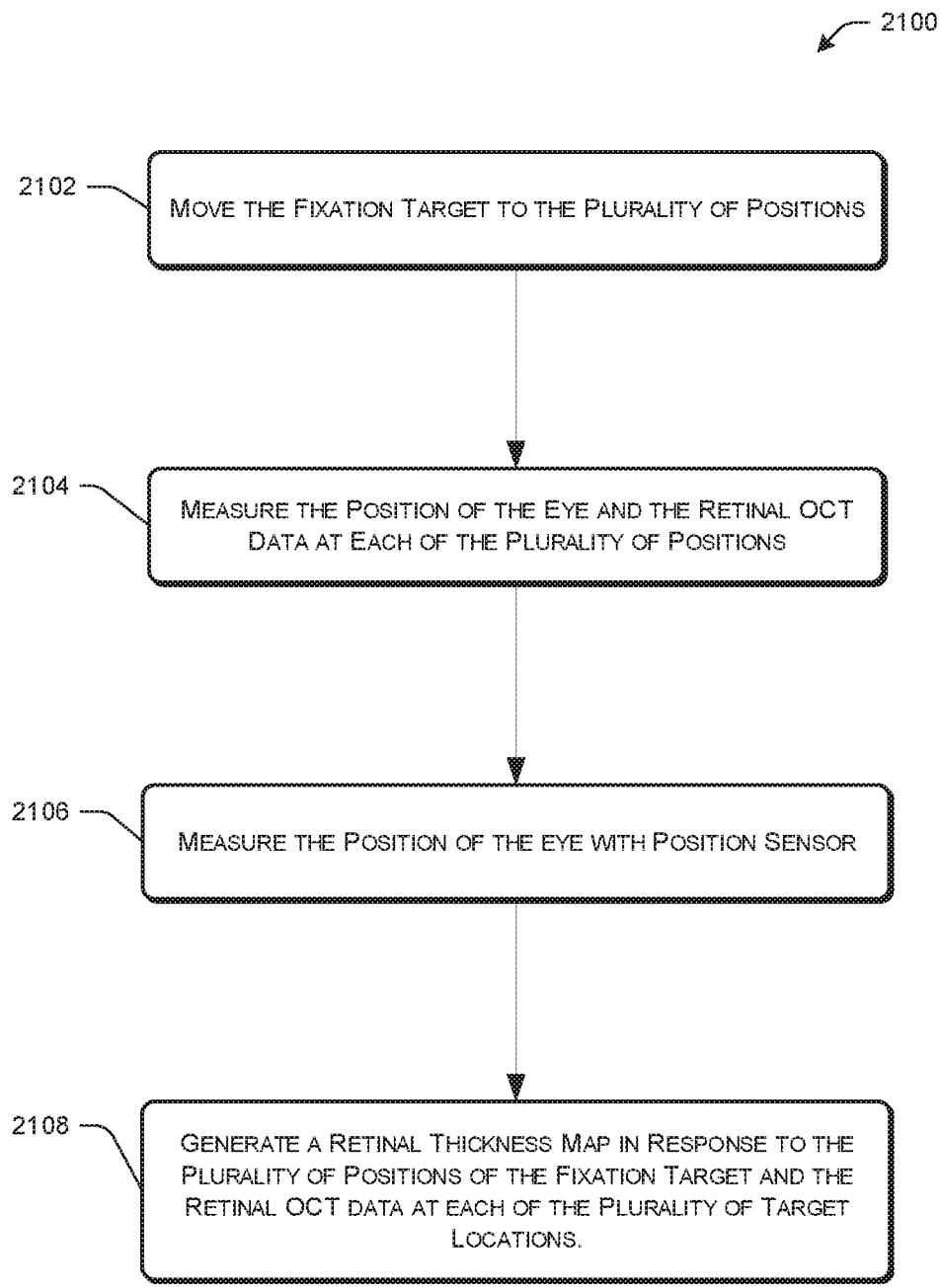
FIG. 21 shows a sample flow diagram for generating a retinal thickness map, in accordance with some embodiments.

FIG. 21 shows a method 2100 of measuring a retina of an eye, in accordance with some embodiments. The method 2100 comprises the following steps:

2102, move the fixation target to the plurality of positions 2104 measure the position of the eye and the retinal OCT data at each of the plurality of positions.

2106 measure the position of the eye with position sensor. The position sensor may comprise a plurality of light sources arranged to generate a Purkinje image and an image sensor to capture the Purkinje image.

2108, generate a retinal thickness map in response to the plurality of positions of the fixation target and the retinal OCT data at each of the plurality of target locations.

Although FIG. 21 shows method 2100 in accordance with some embodiments, one of ordinary skill in the art will recognize many adaptations and variations. For example, the steps can be performed in any suitable order, some of the steps omitted, some of the steps repeated, and some of the steps may comprise sub-steps.

In some embodiments, the OCT measurement beam remains substantially fixed relative to the position sensor at each of the plurality of positions of the fixation target.

In some embodiments the retinal thickness map comprises a plurality of regions corresponding to the plurality of positions of the fixation target.

In some embodiments, the retinal thickness map comprises from 5 to 20 regions and the plurality of locations of the fixation target comprises from 5 to 20 regions.

In some embodiments the OCT system does not comprise a scanner to move the OCT measurement beam to a plurality of locations of the retina.

In some embodiments, the OCT system further comprises a scanner to scan the OCT beam to a plurality of retinal positions for each of the plurality of positions of the fixation target. For example, the scanner can be configured to scan an area of the retina with the plurality of retinal positions for each of the plurality of fixation target positions, and the area of the retina scanned with each of the plurality of fixation target positions is less than an area of the one or more of retinal thickness map or the retinal image.

In some embodiments, the OCT measurement beam is transmitted the scanning mirror mounted on a piezo driven motor in order to compensate for the optical path distance. For example, the hot mirror configured to reflect the OCT measurement beam and transmit the fixation target can be configured to translate in order to adjust the optical path difference while the position of the XYZ translation stage remains substantially fixed. In some embodiments, the translation of the mirror will reflect the OCT measurement beam to adjust the OPD while the path of the transmitted light remains substantially unaltered, such as the path of the light from the fixation target and optionally light transmitted through the mirror to the position sensor.

In some embodiments, the OCT beam is routed through a micromirror/microlens assembly, in which both direction and OPD can be adjusted. In some embodiments, the beam radius is also varied. The micro-optics assembly may be mounted on a set of linear drives, including piezo drives with submicron resolution. Such drives are commercially available from DTI motors as described on the Internet at dtimotors.com.

Such a system may rely on a decreased driving force, so that a driving force of 1 N is be sufficient, in accordance with some embodiments.

In some embodiments the driving force is within a range from 0.5 Newtons (N) to 2.5 N, and a resolution does not to exceed 0.5 microns. In some embodiments, the response time is 1 mm per 0.1 sec or faster. This lens assembly can be controlled with a processor such as a microcontroller or an FPGA, so as to increase the signal to noise ratio as described herein. In some embodiments, the lens assembly is configured to dither the OCT measurement beam on the retina.

As used herein, the terms "patient" and "user" are used interchangeably.

As used herein, the terms "OCT device" and "OCT system" are used interchangeably.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination. The term "and/or" is used similarly.

The present disclosure includes the following numbered clauses.

Clause 1. An optical coherence tomography (OCT) system to measure a retina of an eye, comprising: an OCT interferometer comprising a light source to generate a measurement beam, a plurality of optical elements, and a detector; a fixation target; and a processor operatively coupled to the plurality of optical elements and the fixation target to compensate for the refractive error of the eye in response to an intensity of the light beam reflected from the retina.

Clause 2. An optical coherence tomography (OCT) system to measure a retina of an eye, the OCT system comprising: an OCT interferometer comprising, a detector, a light source comprising one or more of light sources configured to generate one or more light beams, and a plurality of optical elements coupled to the light source to direct the one or more light beams to the retina and generate an interference signal at the detector; a fixation target; a three-axis translation stage to translate the plurality of optical elements and the fixation target relative to the eye to position of the OCT interferometer and compensate for a refractive error of the eye; and a processor operatively coupled to the three-axis translation stage to position the plurality of optical elements and the fixation target to compensate for the refractive error of the eye in response to an intensity of the one or more light beams reflected from the retina.

Clause 3. The OCT system of clause 2, wherein the peak intensity comprises a peak intensity of light reflected from the retina measured with the detector and optionally wherein the peak intensity comprises a peak measured with the detector without measuring interference between a measurement arm and a reference arm of the OCT interferometer.

Clause 4. The OCT system of clause 2, wherein the plurality of optical elements comprises a lens supported with the three axis translation stage, the lens coupled to the three axis translation stage with movement along a fourth axis relative the three axis translation stage to correct the refractive error.

Clause 5. The OCT system of clause 4, wherein the processor is configured with instructions to translate the lens along the fourth axis to substantially fix a vertex distance from the lens to a cornea of the eye in response to movement of the fixation target along one or more axes of the three axis translation stage.

Clause 6. The OCT system of clause 5, wherein the OCT interferometer comprises a reference arm and a measurement arm, the measurement arm comprising an optical fiber comprising an end oriented toward a lens along an optical path of the measurement arm, wherein the end and the lens are configured to translate on the three axis translation stage.

Clause 7. The OCT system of clause 6, wherein the end and the lens are operatively coupled to the processor to move the end and the lens in response to an optical path difference, and wherein the end and the lens are coupled to the three axis translation stage to move along a fifth axis to correct the optical path difference between the measurement arm and the reference arm.

Clause 8. The OCT system of clause 2, wherein the processor configured with instructions to: translate a lens to a plurality of positions relative to the fixation target associated with a plurality of refractive errors; determine the intensity at each of the plurality of positions; determine a position of the lens corresponding to a peak intensity; and place the lens at the position to corresponding to the peak intensity.

Clause 9. The OCT system of clause 8, wherein the lens is movable relative to a fixation target and at least a portion of the OCT interferometer to compensate for the refractive error of the eye and wherein the OCT interferometer further comprises a non-transitory computer readable medium configured to store data associated with refractive error compensation of a left eye and a refractive compensation of a right eye.

Clause 10. The OCT system of clause 9, wherein the instructions cause the processor to adjust the lens in response to the stored refractive error data of the right eye and the stored refractive error data of the left eye.

Clause 11. The OCT system of clause 2, further comprising a sensor to measure a position of the eye, the sensor coupled to the processor configured with instructions to move the three axis translation stage to align the OCT interferometer with the eye.

Clause 12. The OCT system of clause 2, wherein the sensor comprises a camera to image an anterior portion of the eye and determine a position of the eye in relation to an axis extending between an adjustable lens and the fixation target, and wherein the processor is operably coupled to the camera to determine the position of the eye in response to a signal from the camera and the image and optionally wherein the image comprises one or more of an image of a pupil of the eye, a Purkinje image of light reflected from a cornea of the eye, or an image of a laser beam reflected from the eye.

Clause 13. The OCT system of clause 11, wherein the processor is configured with instructions to adjust a measurement region on a retina of the eye in response to the position of the eye.

Clause 14. The OCT system of clause 11, wherein the processor is configured to adjust an output map of retinal thickness in response to the position of the eye.

Clause 15. The OCT system of clause 2, wherein the OCT interferometer comprises one or more of a time domain OCT interferometer, a swept source OCT interferometer, spectral domain OCT interferometer or a multiple reflectance OCT interferometer.

Clause 16. The OCT system of clause 2, wherein the one or more light sources comprises a plurality of light sources, the plurality of light sources comprising a plurality of VCSELs and wherein the circuitry is configured to sequentially activate each of the plurality of VCSELs in order to extend a spectral range.

Clause 17. The OCT system of clause 2, wherein the one or more light beams comprises a variable wavelength and wherein the circuitry is configured to vary the wavelength with a drive current from the circuitry.

Clause 18. The OCT system of clause 2, further comprising a movable collimator to compensate for an optical path difference (OPD), and optionally wherein the movable collimator comprises an end of an optical fiber and a lens, the end of the optical fiber comprising an end of an optical fiber of a measurement arm of an OCT interferometer, the lens positioned with respect to the optical fiber to substantially collimate a light beam from the optical fiber.

Clause 19. An OCT system comprising: a printed circuit board comprising a processor and a plurality of electrical components coupled to the processor; a support comprising a plurality of optics modules mounted on the support, the plurality of optics modules comprising a scanner, a fixation target, and one or more lenses coupled to the scanner and the fixation target; a plurality of actuators coupled to the support and configured to translate the support along three axes; an interferometer module comprising a plurality of optical fibers, a plurality of optical fiber couplers, an optical fiber reference arm and an optical fiber portion of a measurement arm; and an external housing enclosing the printed circuit board, the support and the interferometer module.

Clause 20. The OCT system of clause 19, wherein the external housing is coupled to a patient support comprising on or more of an eyepiece, a headrest or chin rest, and the support is configured to move relative to the external housing and the patient support in response to the actuators to move the components supported thereon into alignment with the eye.

Clause 21. The OCT system of clause 19, wherein the support comprises a plate with the plurality of optics modules mounted thereon.

Clause 22. The OCT system of clause 19, wherein the OCT system comprises a base and the interferometer module is located within the base.

Clause 23. The OCT system of clause 19, wherein the plurality of optical fibers comprises a source optical fiber coupled to a swept source laser and optionally wherein the swept source laser is located inside the housing.

Clause 24. The OCT system of clause 19, wherein the plurality of optical fibers comprises a pair of optical fibers extending from a first and second arm coupler located within the housing to a pair of balanced detectors located outside the housing and wherein the first and second arm coupler couples the reference arm to the optical fiber portion of the measurement arm and optionally wherein the pair of balanced detectors is operatively coupled to the processor on the printed circuit board.

Clause 25. The OCT system of clause 19, wherein the optical fiber portion of the measurement arm extends from an optical coupler coupled to the optical fiber reference arm within the housing to an end outside the housing, the end coupled to a lens to direct a measurement light beam toward an eye of the user.

Clause 26. The OCT system of clause 19, wherein the plurality of optical fibers comprises a phase monitor optical fiber coupled to a swept source laser, the phase monitor optical fiber extending from a coupler located within the housing to an end located outside the housing, the end optically coupled to an etalon and a phase detector to measure a phase of light emitted from the swept source laser and optionally wherein the phase detector is operatively coupled to the processor on the printed circuit board.

Clause 27. The OCT system of clause 19, wherein the plurality of optical fibers comprises a pair of optical power monitor fibers, the pair of optical monitor fibers extending from a coupler located within the housing to a pair of optical monitor detectors, the pair of optical monitor detectors configured to independently measure power of the swept source laser and optionally wherein the pair of optical monitor detectors is operatively coupled to the processor on the printed circuit board.

Clause 28. The OCT system of clause 19, further comprising a processor and a non-transitory computer-readable medium storing instructions, that, when executed by the processor, cause the processor to: determine a position of an eye; move the support by activating one or more of the plurality of actuators to align the fixation target with the eye; adjust the one or more lenses for a refractive error of the eye; adjust the one or more lenses for optical path distance; and acquire retinal data associated with the eye.

Clause 29. The OCT system of clause 28, wherein to adjusting one or more lenses for the refractive error comprises: translating the one or more lenses to a plurality of positions associated with a range of refractive errors; determining an intensity of a measurement beam reflected from the retina each of the plurality of positions; determining a peak intensity signal; and locating the one or more lenses so as to correspond with the peak intensity signal.

Clause 30. The OCT system of clause 28, wherein to adjust the one or more lenses for optical path distance comprises: adjust the optical path distance to a plurality of positions; determine a signal to noise ratio of an OCT interference signal at the plurality of positions; determine a peak signal to noise ratio of the OCT interference signal; and place the one or more lenses at a position corresponding with the peak signal to noise ratio.

Clause 31. An OCT system to measure an eye of a user, the OCT system comprising: a fixation target visible to the eye; an OCT interferometer configured to measure thickness of a retina of the eye; a plurality of light sources arranged to reflect from a cornea of the eye and generate a Purkinje image comprising reflections of the plurality of light sources from the cornea; a sensor to measure a position of the Purkinje image reflected from the cornea; a processor operatively coupled to the sensor to determine a position of the eye in response to the Purkinje image; and a three-axis translation stage configured to move, under control of the processor, at least a portion of the OCT interferometer into alignment with the eye.

Clause 32. The OCT system of clause 31, wherein the processor is configured with instructions to move the at least the portion of the OCT interferometer in one or more of an X direction or a Y direction into alignment with the eye.

Clause 33. The OCT system of clause 31, wherein the sensor comprises a camera comprising a sensor array to capture the Purkinje image and the processor is configured with instructions to determine the position of the eye in response to the reflections of the plurality of light sources and optionally wherein the camera comprises a CMOS sensor array.

Clause 34. The OCT system of clause 31, wherein sensor comprises one or more of a quadrant detector or a position sensitive detector to determine the position of the eye in response to the reflections of the plurality of light sources.

Clause 35. The OCT system of clause 31, further comprising a scanner coupled to the processor to scan a measurement beam the OCT interferometer over an area of a retina of the eye to generate a map of retinal thickness and record a position of the eye in response to the Purkinje image.

Clause 36. The OCT system of clause 35, wherein the processor is configured to output the map of retinal thickness and the position of the eye.

Clause 37. The OCT system of clause 35, wherein the processor is configured to adjust a position of the map of retinal thickness in response to the position of the eye.

Clause 38. The OCT system of clause 31, wherein the processor is configured to adjust a position of a scan pattern on the retina in response to the position of the eye.

Clause 39. The OCT system of clause 31, wherein the processor is configured with instructions to determine XY positions of the eye in relation to the OCT measurement beam in response to locations of the reflections in the Purkinje image, the XY positions of the eye corresponding to locations transverse to the OCT measurement beam and optionally wherein each of the XY positions corresponds to a central location between reflections of the plurality of light sources of the Purkinje image and optionally wherein the central location corresponds to a midpoint between a first pair of reflections and a midpoint between a second pair of reflections of the Purkinje image.

Clause 40. The OCT system of clause 39, wherein the processor is configured with instructions to determine a Z position of the eye corresponding to a distance along the OCT measurement beam in response to distances between the reflections in the Purkinje image.

Clause 41. The OCT system of clause 31, wherein the processor is configured with instructions to automatically scan the retina in response to a position of the eye with an amount of error of no more than about 0.75 mm.

Clause 42. The OCT system of clause 31, wherein illumination of the fixation target overlaps and illumination of the plurality of light sources overlap with scanning of the retina with the OCT measurement beam.

Clause 43. The OCT system of clause 31, wherein a scanned region of the retina comprises dimensions across within a range from about 1 mm to about 3 mm and wherein a number of A-scans comprises from about 5000 A-scans to about 40,000 A-scans over a time within a range from about 0.5 seconds to about 3 seconds and wherein the safety pause is within a range from about 2 to 10 seconds.

Clause 44. The OCT system of clause 31, wherein an optical path extends between the fixation target and the eye and the OCT interferometer measurement beam overlaps with the optical path and the plurality of light sources is distributed around the optical path.

Clause 45. The OCT system of clause 31, wherein the plurality of light sources comprises a laser to generate a laser beam, wherein a position of the reflected laser beam in the image corresponds to a position of the eye along an optical axis.

Clause 46. The OCT system of clause 31, wherein the plurality of light sources comprises a first plurality of light sources and a second light source, the first plurality of light sources configured to generate a pattern when reflected from the cornea, the second light source comprising a laser, wherein a position of the reflected laser beam in the image corresponds to a position of the eye along an optical axis.

Clause 47. The OCT system of clause 31, further comprising a first beam splitter configured to reflect the measurement beam from a scanning mirror and transmit light from the Purkinje image and the fixation target, a second beam splitter configured to reflect light from the Purkinje image to the sensor and transmit light from the fixation target.

Clause 48. The OCT system of clause 47, wherein the plurality of light sources to generate the Purkinje image comprises a wavelength within a range from about 700 to 800 nm, the fixation target comprises a wavelength within a range from about 500 to 700 nm, and the OCT measurement beam comprises a plurality of wavelengths within a range from about 800 to 900 nm.

Clause 49. The OCT system of clause 47, wherein the plurality of light sources to generate the Purkinje image comprises from 3 to 8 light sources and optionally wherein the plurality of light sources comprises from 3 to 8 light emitting diodes.

Clause 50. The OCT system of clause 47, wherein the plurality of light sources comprises a laser to generate a laser beam, wherein a position of the reflected laser beam in the image corresponds to a position of the eye along an optical axis.

Clause 51. A method of measuring a retina of an eye, comprising: aligning a lens to a target vertex distance from a cornea of the eye; iteratively moving the lens to a plurality of positions to determine a peak intensity position to correct for a refractive error of the eye; and acquiring retinal OCT data.

Clause 52. The method of clause 51, further comprising iteratively adjusting an optical path distance to determine a peak signal to noise ratio of an OCT interference signal when the lens has been placed in a position corresponding to the peak intensity.

Clause 53. The method of clause 51, wherein aligning the lens to the vertex distance comprises moving the lens in relation to the cornea of the eye in response to a measured position of the eye.

Clause 54. The method of clause 51, further comprising illuminating the cornea user with a plurality of lights to generate a Purkinje image.

Clause 55. The method of clause 54, further comprising moving the lens laterally with an XY translation to align an OCT measurement beam with a pupil of the eye in response to a position of the Purkinje image.

Clause 56. The method of clause 51, wherein correcting for refractive error comprises: moving the lens and an OCT optics across a range of refractive error correction positions; determining a peak intensity signal across the range of refractive error correction positions; positioning the lens and the OCT optics at a location corresponding with the peak intensity signal.

Clause 57. The method of clause 51, wherein acquiring retinal data is performed automatically.

Clause 58. The method of clause 51, further comprising actively tracking the XY position of an eye.

Clause 59. The method of clause 58, further comprising moving the lens to align with the eye.

Clause 60. An OCT system comprising: a support comprising a plurality of optics modules mounted on the support, the plurality of optics modules comprising a scanner, a fixation target, and one or more lenses coupled to the scanner and the fixation target; and a plurality of actuators coupled to the support and configured to translate the support along three axes, wherein a lens to correct refractive error is supported with the support and moveable along a fourth axis relative to the support.

Clause 61. The OCT system of clause 60, further comprising one or more processors and instructions that, when executed by the one or more processors cause the OCT system to: position the fixation target at a first location; capture first RT data while the fixation target is at the first location; position the fixation target at a second location; and capture second RT data while the fixation target is at the second location.

Clause 62. The OCT system of clause 61, wherein the instructions further cause the one or more processors to compile the first RT data and the second RT data and generate an RT map.

Clause 63. An OCT system to measure a retina of an eye, comprising: an interferometer to measure retinal data with an OCT measurement beam; a visual fixation target configured to move to a plurality positions relative to the beam; a position sensor to measure a position of the eye; and a processor operatively coupled to the interferometer, the fixation target and the position sensor, the processor configured with instructions to move the fixation target to the plurality of positions and measure the position of the eye and the retinal data at each of the plurality of positions.

Clause 64. The OCT system of clause 63, wherein the position sensor comprises a plurality of light sources arranged to generate a Purkinje image and an image sensor to capture the Purkinje image.

Clause 65. The OCT system of clause 63, wherein the OCT measurement beam remains substantially fixed relative to the position sensor at each of the plurality of positions of the fixation target.

Clause 66. The OCT system of clause 65, wherein the processor is configured with instructions to generate a retinal thickness map in response to the plurality of positions of the fixation target.

Clause 67. The OCT system of clause 66, wherein the retinal thickness map comprises a plurality of regions corresponding to the plurality of positions of the fixation target.

Clause 68. The OCT system of clause 67, wherein the retinal thickness map comprises from 5 to 20 regions and the plurality of locations of the fixation target comprises from 5 to 20 regions.

Clause 69. The OCT system of clause 68, wherein the OCT system does not comprise a scanner to move the OCT measurement beam to a plurality of locations of the retina.

Clause 70. The OCT system of clause 63, further comprising a scanner to scan the OCT beam to a plurality of retinal positions for each of the plurality of positions of the fixation target.

Clause 71. The OCT system of clause 70, wherein the processor is configured with instructions to combine retinal thickness data from each of the plurality of positions of the fixation target to generate one or more of a retinal thickness map or a retinal image.

Clause 72. The OCT system of clause 71, wherein the scanner is configured to scan an area of the retina with the plurality of retinal positions for each of the plurality of fixation target positions, and wherein the area of the retina scanned with each of the plurality of fixation target positions is less than an area of the one or more of retinal thickness map or the retinal image.

Clause 73. The OCT system of any one of the preceding clauses, wherein the OCT system comprises a monocular OCT system.

Clause 74. The OCT system or method of any one of the preceding clauses, wherein a scanner is configured to scan a measurement beam along the retina with a trajectory.

Clause 75. The OCT system or method of any one of the preceding clauses, wherein the one or more light sources is configured to sweep a wavelength emitted by the source over a range of wavelengths from about 20 nm to about 100 nm.

Clause 76. The OCT system or method of any one of the preceding clauses, wherein the one or more light sources comprises a MEMS tunable VCSEL configured to move a mirror to scan the wavelength.

Clause 77. The OCT system or method of any one of the preceding clauses, wherein the processor is configured with instructions to generate a 3D tomographic image of the retina.

Clause 78. The OCT system or method of any one of the preceding clauses, wherein a scanning mirror is configured to translate in order to adjust an optical path difference between a measurement arm and a reference arm of an OCT interferometer and optionally wherein an actuator coupled to the mirror is configured to drive the mirror with a force within a range from 0.5 to 2.5 N and a resolution not exceeding 0.5 microns.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An optical coherence tomography (OCT) system to measure a retina of an eye, the OCT system comprising:
   an OCT interferometer comprising, a detector, a light source comprising one or more of light sources configured to generate one or more light beams, and a plurality of optical elements coupled to the light source to direct the one or more light beams to the retina and generate an interference signal at the detector;
   a fixation target;
   a three-axis translation stage to translate the plurality of optical elements and the fixation target relative to the eye to position of the OCT interferometer and compensate for a refractive error of the eye; and
   a processor operatively coupled to the three-axis translation stage to position the plurality of optical elements and the fixation target to compensate for the refractive error of the eye in response to an intensity of the one or more light beams reflected from the retina;
   wherein the plurality of optical elements comprises a lens supported with a three axis translation stage, the lens coupled to the three axis translation stage with movement along a fourth axis relative the three axis translation stage to correct the refractive error.

2. The OCT system of claim 1, wherein a peak intensity comprises a peak intensity of light reflected from the retina measured with the detector.

3. The OCT system of claim 1 wherein the processor is configured with instructions to translate the lens along the fourth axis to substantially fix a vertex distance from the lens to a cornea of the eye in response to movement of the fixation target along one or more axes of the three axis translation stage.

4. The OCT system of claim 3, wherein the OCT interferometer comprises a reference arm and a measurement arm, the measurement arm comprising an optical fiber comprising an end oriented toward a lens along an optical path of the measurement arm, wherein the end and the lens are configured to translate on the three axis translation stage.

5. The OCT system of claim 4, wherein the end and the lens are operatively coupled to the processor to move the end and the lens in response to an optical path difference, and wherein the end and the lens are coupled to the three axis translation stage to move along a fifth axis to correct the optical path difference between the measurement arm and the reference arm.

6. The OCT system of claim 1, further comprising a sensor to measure a position of the eye, the sensor coupled to the processor configured with instructions to move the three axis translation stage to align the OCT interferometer with the eye.

7. The OCT system of claim 6, wherein the processor is configured with instructions to adjust a measurement region on the retina of the eye in response to the position of the eye.

8. The OCT system of claim 6, wherein the processor is configured to adjust an output map of retinal thickness in response to the position of the eye.

9. The OCT system of claim 1, further comprising a movable collimator to compensate for an optical path difference (OPD), and wherein the movable collimator comprises an end of an optical fiber and a lens, the end of the optical fiber comprising an end of an optical fiber of a measurement arm of the OCT interferometer, the lens positioned with respect to the optical fiber to substantially collimate the one or more light beams from the optical fiber.

10. An OCT system comprising:
    a printed circuit board comprising a processor and a plurality of electrical components coupled to the processor;
    a support comprising a plurality of optics modules mounted on the support, the plurality of optics modules comprising a scanner, a fixation target, and one or more lenses coupled to the scanner and the fixation target;
    a plurality of actuators coupled to the support and configured to translate the support along three axes;
    an interferometer module comprising a plurality of optical fibers, a plurality of optical fiber couplers, an optical fiber reference arm and an optical fiber portion of a measurement arm; and
    a housing enclosing the printed circuit board, the support and the interferometer module, wherein the optical fiber portion of the measurement arm extends from an optical coupler coupled to the optical fiber reference arm within the housing to an end outside the housing, the end coupled to a lens to direct a measurement light beam toward an eye of a user.

11. The OCT system of claim 10, wherein the plurality of optical fibers comprises a pair of optical fibers extending from a first and second arm coupler located within the housing to a pair of balanced detectors located outside the housing and wherein the first and second arm coupler couples the optical fiber reference arm to the optical fiber portion of the measurement arm.

12. The OCT system of claim 10, wherein the plurality of optical fibers comprises a phase monitor optical fiber coupled to a swept source laser, the phase monitor optical fiber extending from a coupler located within the housing to an end located outside the housing, the end optically coupled to an etalon and a phase detector to measure a phase of light emitted from the swept source laser.

13. The OCT system of claim 10, wherein the plurality of optical fibers comprises a pair of optical power monitor fibers, the pair of optical monitor fibers extending from a coupler located within the housing to a pair of optical monitor detectors, the pair of optical monitor detectors configured to independently measure power of the swept source laser.

14. The OCT system of claim 10, further comprising a non-transitory computer-readable medium storing instructions, that, when executed by the processor, cause the processor to:
    determine a position of the eye;
    move the support by activating one or more of the plurality of actuators to align the fixation target with the eye;

adjust the one or more lenses for a refractive error of the eye;
adjust the one or more lenses for optical path distance; and
acquire retinal data associated with the eye.

15. The OCT system of claim 14, wherein to adjust the one or more lenses for optical path distance comprises:
adjust the one or more lenses for optical path distance to a plurality of positions;
determine a signal to noise ratio of an OCT interference signal at the plurality of positions;
determine a peak signal to noise ratio of the OCT interference signal; and
place the one or more lenses at a position corresponding with the peak signal to noise ratio.

16. An OCT system comprising:
a support comprising a plurality of optics modules mounted on the support, the plurality of optics modules comprising a scanner, a fixation target, and one or more lenses coupled to the scanner and the fixation target;
a plurality of actuators coupled to the support and configured to translate the support along three axes, wherein a lens to correct refractive error is supported with the support and moveable along a fourth axis relative to the support; and
one or more processors and instructions that, when executed by the one or more processors cause the OCT system to:
position the fixation target at a first location;
capture first retinal thickness data (RT) data while the fixation target is at the first location;
position the fixation target at a second location; and
capture second RT data while the fixation target is at the second location.

17. The OCT system of claim 16, wherein the instructions further cause the one or more processors to compile the first RT data and the second RT data and generate an RT map.

* * * * *